(12) United States Patent
Harris et al.

(10) Patent No.: US 12,422,046 B2
(45) Date of Patent: Sep. 23, 2025

(54) DEVICES, SYSTEMS, METHODS, AND DESIGNS FOR MEDICAL CLEANING VALVES

(71) Applicant: Boston Scientific Scimed, Inc., Maple Grove, MN (US)

(72) Inventors: Colby Harris, Weston, MA (US); Barry Weitzner, Acton, MA (US); Carolina Villarreal, Hopedale, MA (US); Brian Luis, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 317 days.

(21) Appl. No.: 16/868,325

(22) Filed: May 6, 2020

(65) Prior Publication Data
US 2020/0352415 A1 Nov. 12, 2020

Related U.S. Application Data

(60) Provisional application No. 63/002,759, filed on Mar. 31, 2020, provisional application No. 62/923,197, (Continued)

(51) Int. Cl.
*F16K 11/07* (2006.01)
*A61B 1/00* (2006.01)
(Continued)

(52) U.S. Cl.
CPC ...... *F16K 11/0712* (2013.01); *A61B 1/00068* (2013.01); *A61B 1/00137* (2013.01);
(Continued)

(58) Field of Classification Search
CPC ..... A61B 1/00068; A61B 1/137; A61B 1/126; A61B 1/125; A61B 90/92; A61B 90/94;
(Continued)

(56) References Cited

U.S. PATENT DOCUMENTS 4,361,138 A 11/1982 Kinoshita
4,537,209 A 8/1985 Sasa
(Continued)

FOREIGN PATENT DOCUMENTS

EP 0069913 A2 1/1983
EP 2878252 A1 6/2015
(Continued)

OTHER PUBLICATIONS

International Search Report and Written Opinion for the International Patent Application No. PCT/US2020/031688, mailed Nov. 8, 2020, 12 pages.
(Continued)

*Primary Examiner* — Michael J Carey
*Assistant Examiner* — Megan Elizabeth Monahan
(74) *Attorney, Agent, or Firm* — Seager, Tufte & Wickhem, LLP

(57) ABSTRACT

A medical cleaning valve (or cleaning valve) may be configured to provide cleaning functionality to air and water channels of an endoscope. One or more embodiments described herein may include cleaning valves with features and/or components that facilitate differentiating them from procedural valves. In some embodiments, valves may be made from a limited number of parts and materials, to limit their cost. For example, multiple seals may be formed as a single component, such as via overmolding. In another example, wiper seals may be used to accommodate greater manufacturing tolerances. In yet another example, the valve may have a single elastomeric component, or spring cap, which may combine the functionality of a number of components (e.g., a boot, spring, spring housing, and stem cap).

20 Claims, 63 Drawing Sheets

Related U.S. Application Data filed on Oct. 18, 2019, provisional application No. 62/844,465, filed on May 7, 2019.

(51) Int. Cl.

| | | |
|---|---|---|
| *A61B 1/12* | (2006.01) | |
| *A61B 90/70* | (2016.01) | |
| *A61B 90/92* | (2016.01) | |
| *A61B 90/94* | (2016.01) | |
| *A61L 2/18* | (2006.01) | |
| *A61M 39/16* | (2006.01) | |
| *A61M 25/00* | (2006.01) | |
| *A61M 39/26* | (2006.01) | |

(52) U.S. Cl.
CPC .............. *A61B 1/126* (2013.01); *A61B 90/70* (2016.02); *A61B 90/92* (2016.02); *A61B 90/94* (2016.02); *A61L 2/18* (2013.01); *A61M 39/16* (2013.01); *F16K 11/0716* (2013.01); *A61B 1/125* (2013.01); *A61B 2090/701* (2016.02); *A61L 2202/24* (2013.01); *A61M 25/007* (2013.01); *A61M 2039/267* (2013.01); *A61M 2205/583* (2013.01); *A61M 2207/00* (2013.01)

(58) Field of Classification Search
CPC .............. A61B 90/70; A61B 2090/701; F16K 11/0712; F16K 11/0716; A61L 2/18; A61L 2202/24; A61M 39/16; A61M 25/007; A61M 2039/267; A61M 2205/583; A61M 2207/00
See application file for complete search history.

(56) References Cited

U.S. PATENT DOCUMENTS

| | | | |
|---|---|---|---|
| 4,694,821 A | 9/1987 | Kondo | |
| 5,027,791 A * | 7/1991 | Takahashi | A61B 1/126 600/158 |
| D391,881 S | 3/1998 | Youseph | |
| D453,830 S | 2/2002 | McDowell et al. | |
| 6,346,075 B1 | 2/2002 | Arai et al. | |
| D611,599 S | 3/2010 | Eisenkolb et al. | |
| D638,537 S | 5/2011 | Virr et al. | |
| 8,771,223 B2 | 7/2014 | Patton et al. | |
| D749,742 S | 2/2016 | Ishibashi et al. | |
| 9,314,269 B2 | 4/2016 | Webb et al. | |
| D779,636 S | 2/2017 | Gross | |
| D855,795 S | 8/2019 | Ritter, III et al. | |
| D861,161 S | 9/2019 | Schuessler | |
| D862,694 S | 10/2019 | Narnekar et al. | |
| D885,571 S | 5/2020 | Haddad et al. | |
| D923,196 S | 6/2021 | Fang et al. | |
| 11,291,761 B2 * | 4/2022 | Friedman | A61M 5/1409 |
| 11,499,650 B2 * | 11/2022 | Smith | F16K 31/52491 |
| 2006/0100485 A1 * | 5/2006 | Arai | A61B 1/00068 600/101 |
| 2012/0071713 A1 | 3/2012 | Kaye et al. | |
| 2013/0276338 A1 | 10/2013 | Amaral | |
| 2013/0303844 A1 | 11/2013 | Grudo et al. | |
| 2014/0207100 A1 | 7/2014 | Webb | |
| 2015/0144215 A1 | 5/2015 | Bellofatto et al. | |
| 2017/0143194 A1 | 5/2017 | Wolfe | |
| 2017/0347860 A1 | 12/2017 | Still et al. | |
| 2020/0016637 A1 * | 1/2020 | Still | A61B 1/125 |
| 2021/0204797 A1 * | 7/2021 | Hernandez | G02B 23/2476 |

FOREIGN PATENT DOCUMENTS

| | | |
|---|---|---|
| EP | 3073889 A1 | 10/2016 |
| JP | D1136651 S | 3/2002 |
| JP | 2006056508 A | 3/2006 |
| JP | 2018514448 A | 6/2018 |
| WO | 03030962 A2 | 4/2003 |
| WO | 2013142211 A1 | 9/2013 |
| WO | 2019226307 A1 | 11/2019 |
| WO | 2020014376 A1 | 1/2020 |

OTHER PUBLICATIONS

International Search Report and Written Opinion for the International Patent Application No. PCT/US2020/031687, mailed Feb. 9, 2020, 13 pages.

Communication Pursuant to Article 94(3) EPC dated Aug. 11, 2023 for application No. 20729370.5.

* cited by examiner

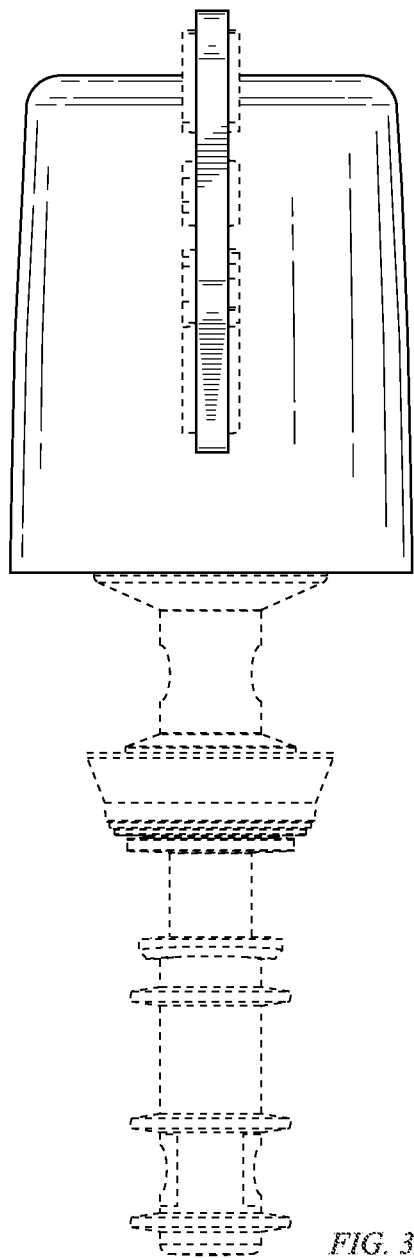
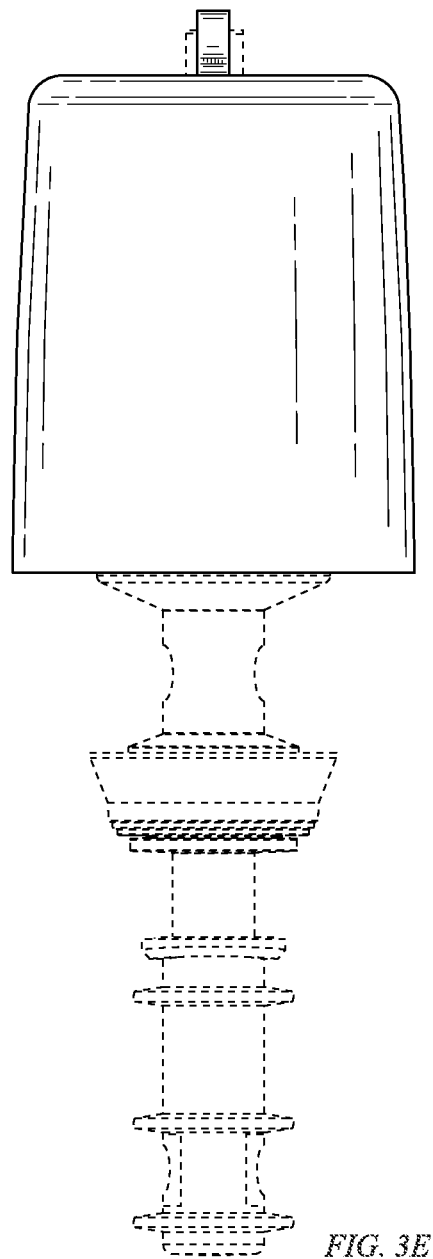
FIG. 3D
FIG. 3E

DEVICES, SYSTEMS, METHODS, AND DESIGNS FOR MEDICAL CLEANING VALVES

RELATED APPLICATIONS

This application claims the benefit of priority under 35 U.S.C. § 119 to U.S. Provisional Application No. 62/844,465, titled "Medical Cleaning Valve", filed on May 7, 2019, the entirety of which is incorporated herein by reference.

This application claims the benefit of priority under 35 U.S.C. § 119 to U.S. Provisional Patent Application No. 62/923,197, titled "Devices, Systems, Methods, and Designs for Medical Cleaning Valves", filed on Oct. 18, 2019, the entirety of which is incorporated herein by reference.

This application claims the benefit of priority under 35 U.S.C. § 119 to U.S. Provisional Patent Application No. 63/002,759, titled "Devices, Systems, and Methods for Medical Cleaning Valves", filed on Mar. 30, 2020, the entirety of which is incorporated herein by reference.

FIELD

The present disclosure relates generally to valves for medical devices. In particular, the present disclosure relates to cleaning valves for medical devices.

BACKGROUND

Endoscopes include functionality to deliver fluids to (including air and water) and suction at a site of a procedure. Tubing for delivering fluids and/or suction extends from a handle of the endoscope, through a shaft of the endoscope, and to a distal tip of the endoscope. During a procedure, body fluids, tissues, or other material can build up in the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. One option for accomplishing such pre-processing is a reusable cleaning valve. Such cleaning valves may include a number of components, including a valve stem (often made of metal), a number of seals, a spring, a spring housing, a boot, and/or a stem cap. The cleaning valve may be inserted into an air/water valve cylinder (i.e., valve well) of an endoscope after the scope is removed from a patient and the procedure valve is removed from the valve cylinder. An operator may then depress a button of the cleaning valve for a predetermined amount of time (e.g., 30 seconds) to flush the air and/or water channels of the endoscope prior to further reprocessing of the endoscope. A reusable cleaning valve must be subject to cleaning, itself, in between uses, which can add to reprocessing cost. It is an important aspect of a cleaning valve that it not be confused with a procedural valve and inadvertently used in place thereof during a procedure when the scope is inserted within a patient. It is with all of the above considerations in mind that the improvements of the present disclosure may be useful.

SUMMARY

In one aspect, the present disclosure relates to a valve for a medical device comprising an interface member for a cleaning valve. The interface member may include a proximal end with a proximal surface, a distal end, one or more indicators, a first connector portion, and a second connector portion. The one or more indicators may differentiate the interface member for the cleaning valve from another interface member for a procedural valve. The first connector portion may be configured to couple with a valve stem of the cleaning valve and the second connector portion may be configured to couple with a valve well for the cleaning valve. The one or more indicators may include a first indicator comprising first and second raised surfaces on the proximal surface of the interface member. In many embodiments, the first raised surface surrounds the second raised surface. In many such embodiments, the first raised surface includes an exclamation point and the second raised surface includes a geometric shape surrounding the exclamation point. In further such embodiments, the geometric shape surrounding the exclamation point includes a circle, a triangle, a square, a rhombus, or a hexagon. In various embodiments, the first and second raised surfaces have a different texture than the proximal surface. In various such embodiments, a texture of the first or second raised surface comprises a multitude of small protrusions including one or more of cones, rods, bumps, loops, and ridges. In some embodiments, the interface member comprises a tacky surface. In some such embodiments, the first and second raised surfaces include a tacky material. In one or more embodiments, the interface member includes a spring portion between the first connector portion and the second connector portion. In many embodiments, the interface member is configured to couple with the valve stem via an interference fit. In various embodiments, the proximal surface and the first or second raised surfaces comprise different colors. Several embodiments include a second indicator that extends laterally from the interface member between the proximal and distal ends of the interface member. In several such embodiments, the second indicator comprises a tag. In further such embodiments, the tag is integrally attached to the interface member. In some such embodiments, the second indicator includes a plurality of raised surfaces to communicate the interface member is for cleaning.

In another aspect, the present disclosure relates to a cleaning valve for a medical device comprising a valve stem, a plurality of seals, an interface member, and an indicator. The valve stem may include a proximal end, a distal end, one or more orifices, and a lumen in fluid communication with the one or more orifices. The plurality of seals may be positioned between the proximal and distal ends of the valve stem. At least one of the plurality of seals may be overmolded onto the valve stem. The interface member may be coupled to the proximal end of the valve stem. The indicator may differentiate the cleaning valve from a procedural valve. In some embodiments, the at least one seal comprises first, second, and third seals. In various embodiments, the at least one seal surrounds a first orifice of the one or more orifices. In various such embodiments, the first orifice comprises a radial hole in the valve stem. In one or more embodiments, the at least one seal plugs a second orifice of the one or more orifices. In one or more such embodiments, the distal end of the valve stem comprises the second orifice. In many embodiments, the indicator is removably disposed about the valve stem and prevents insertion of the valve stem into a valve well when disposed about the valve stem. In some embodiments, the indicator is removably inserted into an orifice of the valve stem and prevents insertion of the valve stem into a valve well when inserted into the orifice of the valve stem.

In yet another aspect, the present disclosure relates to a valve for a medical device comprising a valve stem, an interface member, and a first indicator. The interface member may include a proximal end having a proximal surface and a first connector portion and a second connector portion, the first connector portion coupleable to the valve stem. The first indicator may include one or more raised surfaces on the proximal surface of the interface member. In many embodiments, the one or more raised surfaces include numbers, symbols, geometric shapes, or combinations thereof. In some embodiments, the interface member comprises a spring portion. In some such embodiments, the spring portion of the interface member includes an annular wall having a first portion, a second portion distal to the first portion, and a third portion distal to the second portion. In further such embodiments, a thickness of the annular wall is smaller at the second portion than at both of the first and third portion. In additional such embodiments, in response to a force exerted on the proximal surface, the annular wall is expandable radially outward at the second portion. In various embodiments, the second connector portion is disposed at a distal end of the interface member such that the second connector portion is unattached from the valve stem. In various such embodiments, the second connector portion may be removably attachable to a valve well of an endoscope. In one or more embodiments, in an attached configuration, the valve stem and the interface member are movable between a first configuration and a second configuration such that the valve stem is movable in a valve well of an endoscope. Several embodiments include one or more seals disposed along the valve stem. In many embodiments, the first connector portion of the interface member is configured to couple with the valve stem via an interference fit. In some embodiments, the proximal surface and the one or more raised surfaces comprise different colors, textures, or materials, or combinations thereof. Various embodiments may include a second indicator that extends laterally from the interface member. In various such embodiments, the second indicator comprises a tag. In some such embodiments, the tag is integrally attached to the interface member. In other such embodiments, the tag is removably attachable to the interface member.

In yet another aspect, the present disclosure relates to a method of manufacture. The method may include forming a valve stem including a proximal end, a distal end, one or more orifices, and a lumen in fluid communication with the one or more orifices. The method may include overmolding one or more seals onto the valve stem. The method may include connecting an interface member to the proximal end of the valve stem. The method may include removably coupling an indicator to the valve stem that prevents insertion of the valve stem into a valve well when coupled to the valve stem. In various embodiments, the method includes plugging at least one orifice of the one or more orifices via overmolding the one or more seals onto the valve stem. In many embodiments, the method includes forming the interface member from a tacky material and forming the valve stem from a nontacky material. In several embodiments, the method includes forming a second indicator in a proximal end of the interface member.

In yet another aspect, the present disclosure relates to a medical valve that comprises an inner member and an outer member including an annular wall having an interior surface defining a chamber configured to receive the inner member. The annular wall may have a first portion, a second portion distal to the first portion, and a third portion distal to the second portion. A thickness of the annular wall may be smaller at the second portion than at both of the first portion and the third portion.

Alternatively, or in addition to the above features, any of the exemplary medical valves disclosed herein may have any of the following features. The outer member may be a single, unitary structure formed of a single material. The outer member may have a first configuration and a second configuration. In the second configuration, the outer member may have a shorter length along a longitudinal axis of the valve than in the first configuration. In the second configuration, the annular wall may bulge radially outward at the second portion of the annular wall. The outer member may be coupled to the inner member. The proximal end of the outer member may be coupled to a proximal end of the inner member, and a distal end of the outer member may be unattached from the inner member. The outer member may be releasably attachable to a valve cylinder of an endoscope. The inner member may be a valve stem. In an attached configuration, the medical valve may be movable between a first configuration and a second configuration such that the valve stem is movable in the valve cylinder. The inner member may be a single, unitary structure formed of a single material. The inner member may include a plurality of seals configured to form a slidable interference fit with a wall of an endoscope valve cylinder so that fluid is prevented from passing between each of the plurality of seals and the wall of the endoscope valve cylinder. The interior surface may taper from the first portion to the second portion and from the third portion to the second portion. The valve may consist of the inner member; the outer member; three distal seals; one proximal seal; and a one-way seal. The inner member may be a first single unitary structure formed of a single material. The outer member may be a second single, unitary structure formed of a single material. A radially outer surface of the inner member may include a first aperture and a second aperture. The inner member may include a lumen extending along a longitudinal axis of the valve. The lumen may be in fluid communication with the first aperture and the second aperture. The first aperture may be between the proximal seal and the one-way seal. The second aperture may be between a first of the three distal seals and a second of the three distal seals. The first aperture may be located at a proximal end of the lumen. The second aperture may be located at a distal end of the lumen. The one-way seal may be proximal of the three distal seals.

In yet another aspect, the present disclosure relates to a medical valve that comprises: an inner member; and an outer member defining a chamber receiving the inner member. A proximal portion of the outer member may be coupled to the inner member. A distal portion of the outer member may be releasably attachable to an endoscope valve cylinder. The outer member may be a single unitary structure formed of a single material. In response to an application of a force to an end of the outer member, the outer member may transition from a first configuration to a second configuration that is radially enlarged relative to the first configuration.

Alternatively, or in addition to the above features, any of the exemplary medical valves disclosed herein may have any of the following features. The inner member may be a valve stem. In an attached configuration, the medical valve may be movable between a first configuration and a second configuration such that the valve stem is movable in the valve cylinder. The outer member may include an annular wall having a first portion distal to the proximal portion, a second portion distal to the first portion, and a third portion distal to the second portion. The third portion may be proximal to the distal portion. A thickness of the second portion may be smaller than a thickness of both the first portion and the third portion. The inner member may be a single, unitary structure formed of a single material. The inner member may include a plurality of seals configured to form a slidable interference fit with a wall of an endoscope valve cylinder so that a fluid cannot pass between each of the plurality of seals and the wall of the endoscope valve cylinder. The outer member may be biased to the first configuration.

In yet another aspect, the present disclosure relates to a medical valve comprising: an inner member formed as a valve stem; a plurality of seals disposed along the valve stem; and an outer member including an annular wall having an interior surface defining a chamber configured to receive the inner member, The annular wall may have portions of varying thickness such that, as the outer member transitions from an uncompressed configuration to a compressed configuration, the annular wall is bendable at predetermined location. The outer member may be biased toward the uncompressed configuration.

Alternatively, or in addition to the above features, any of the exemplary medical valves disclosed herein may have any of the following features. The annular wall may have a first portion, a second portion distal to the first portion, and a third portion distal to the second portion. A distance between the interior surface and the exterior surface may be smaller at the second portion than at both of the first portion and the third portion.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3A-3H illustrate first perspective, front, back, right, left, top, bottom, and second perspective views, respectively, of an exemplary embodiment of a medical cleaning valve assembly according to the present disclosure described herein.

DETAILED DESCRIPTION

Figure 1A:
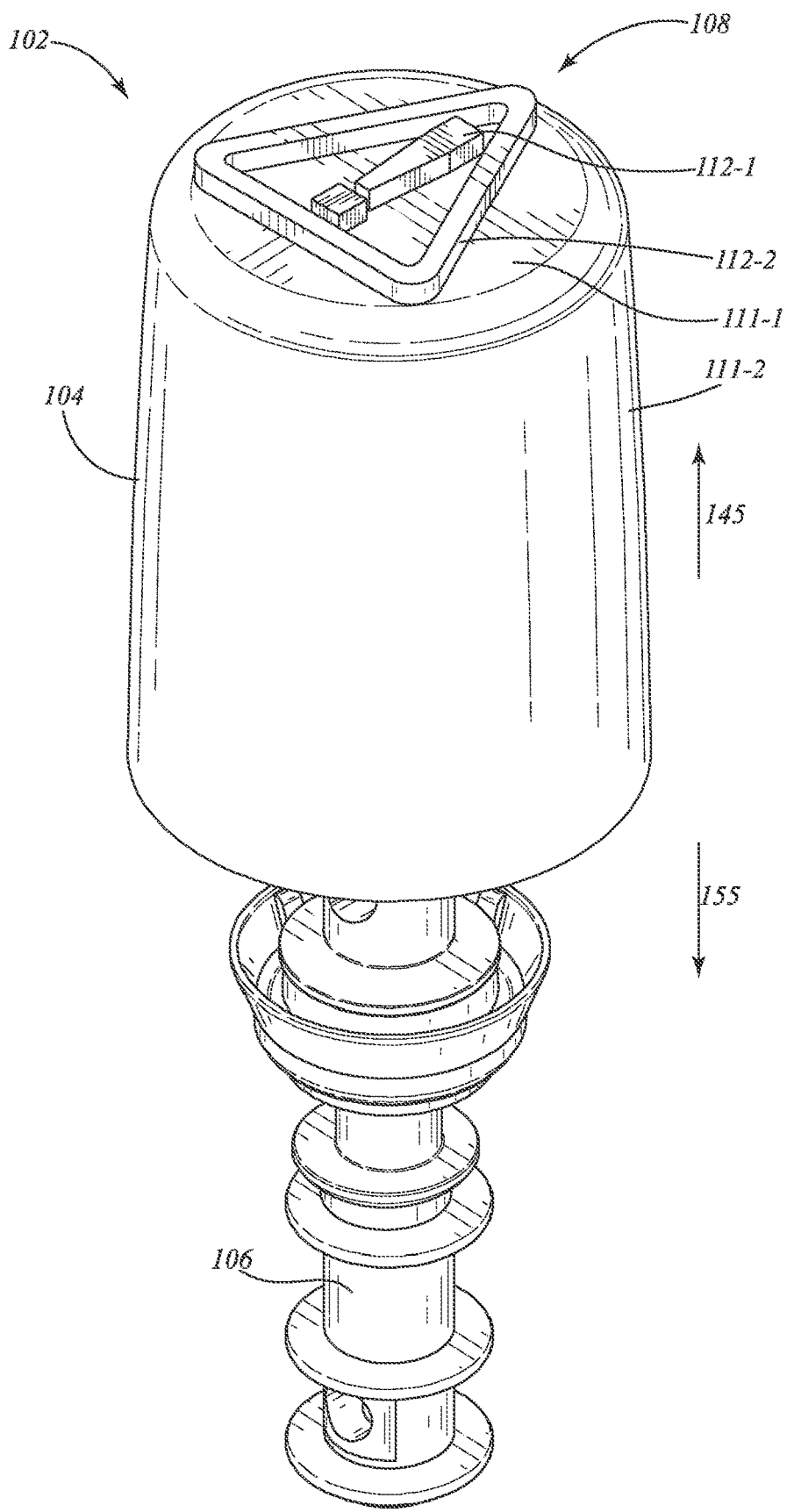
FIGS. 1A-1H illustrate first perspective, front, back, right, left, top, bottom, and second perspective views, respectively, of an exemplary embodiment of a medical cleaning valve assembly according to the present disclosure described herein.
Figure 1B:
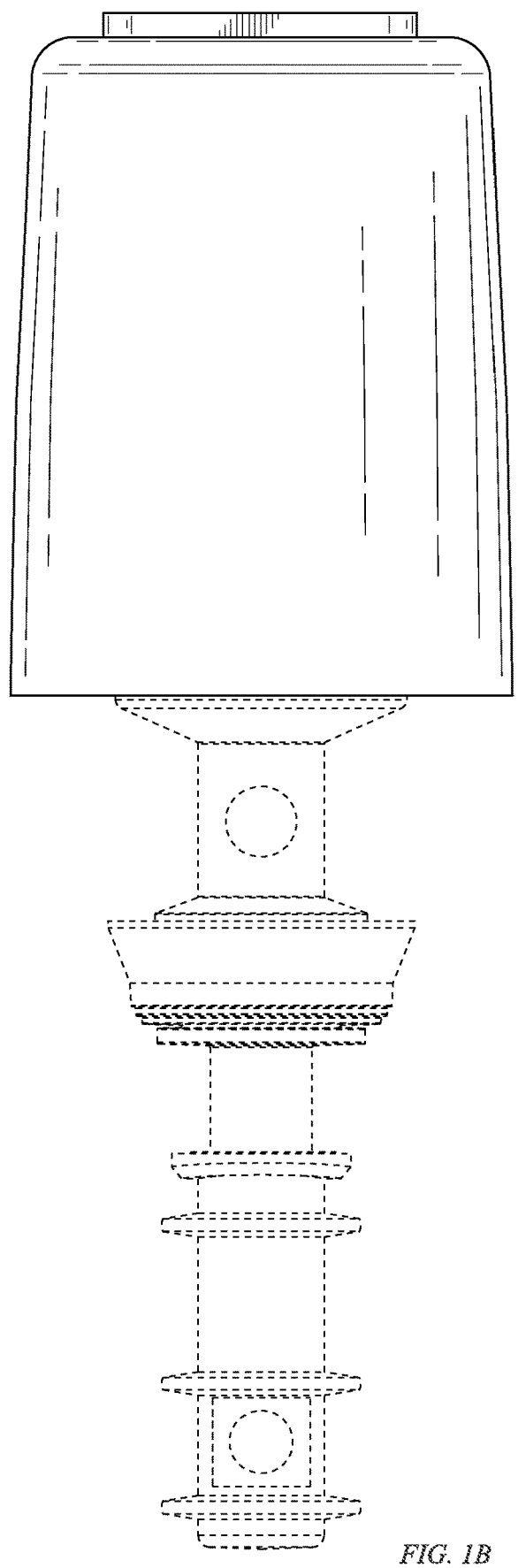
Figure 1C:
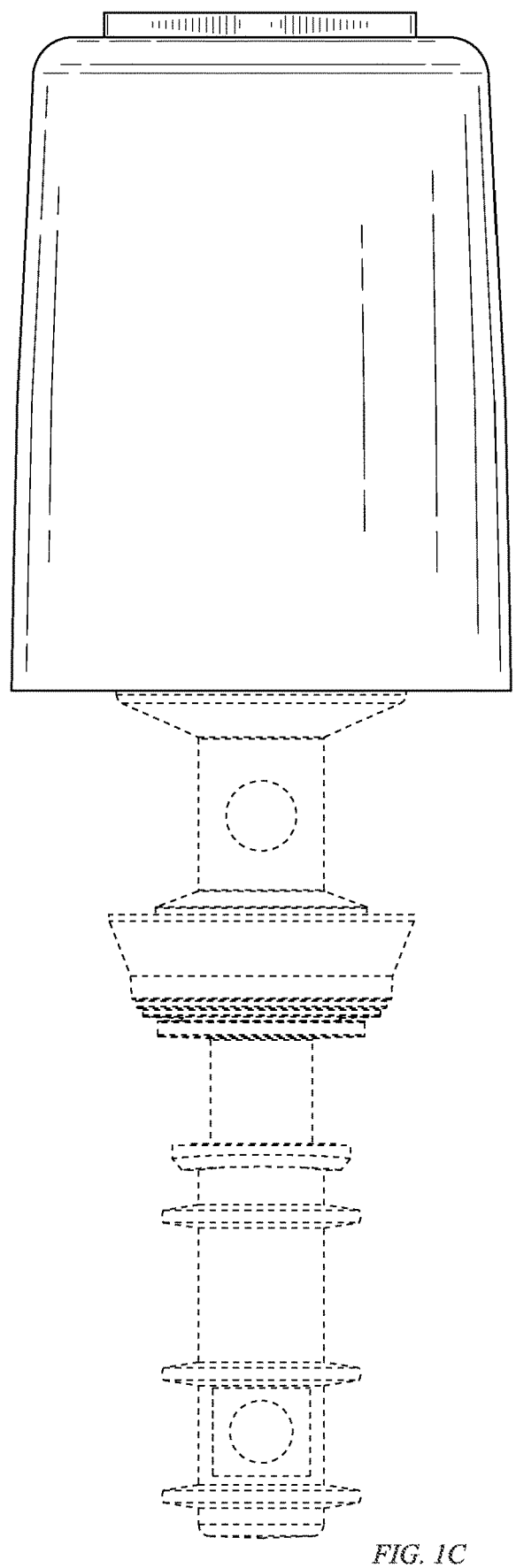
Figure 1D:
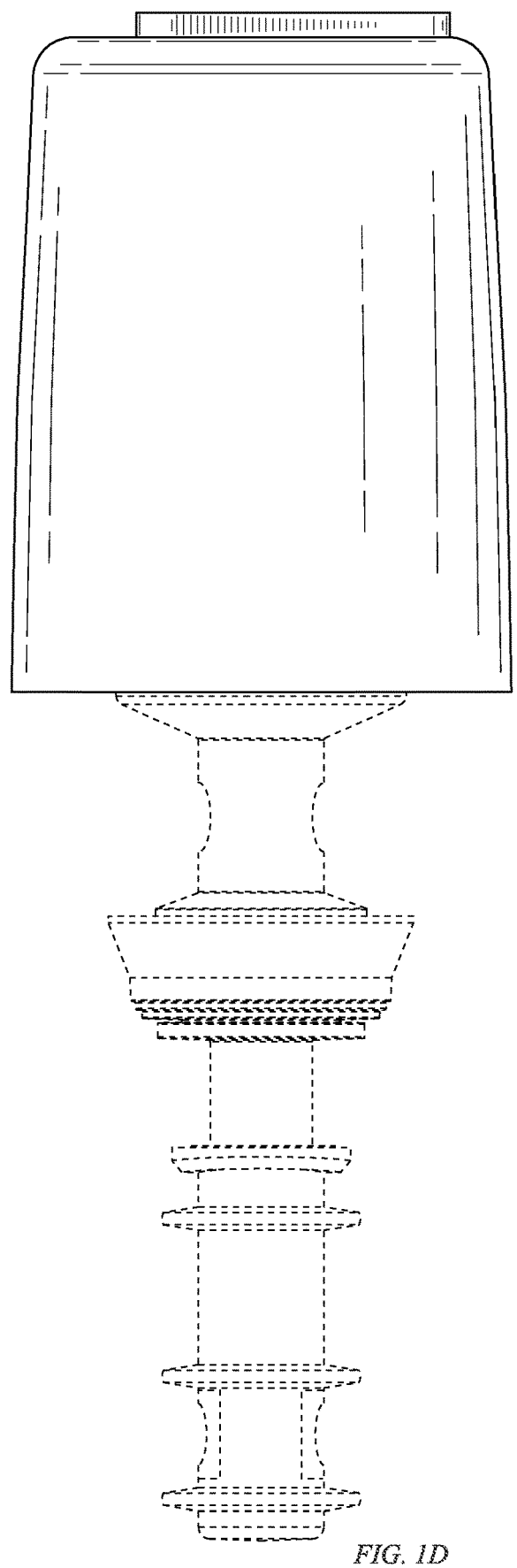
Figure 1E:
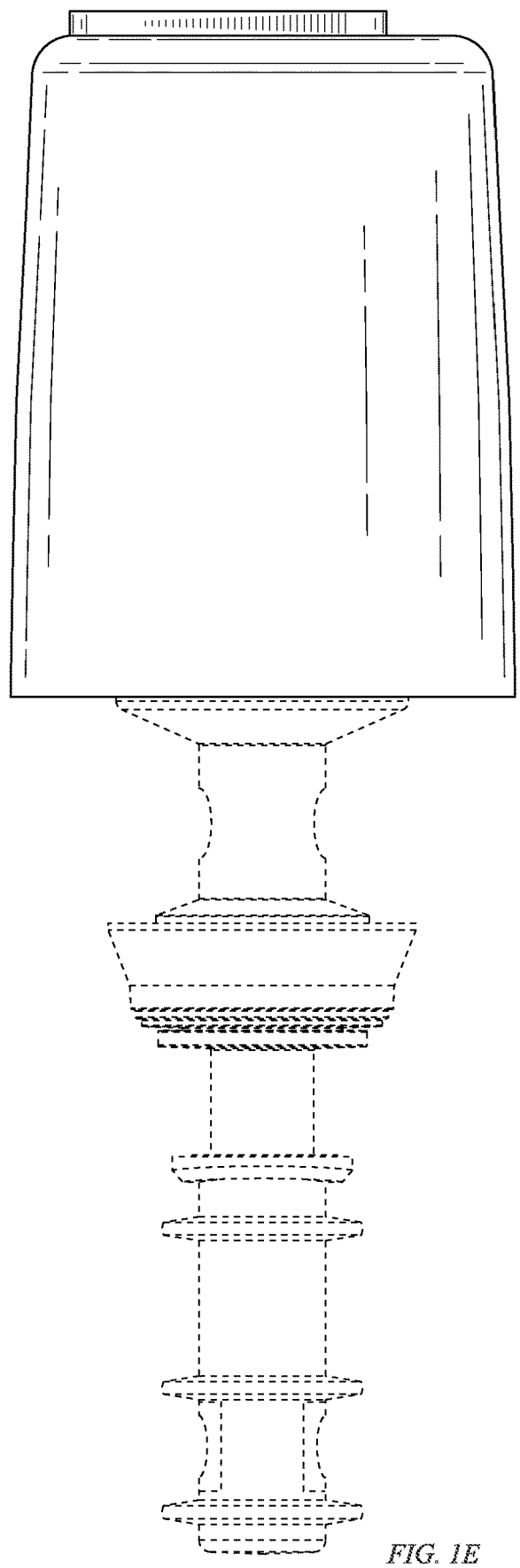
Figure 1F:
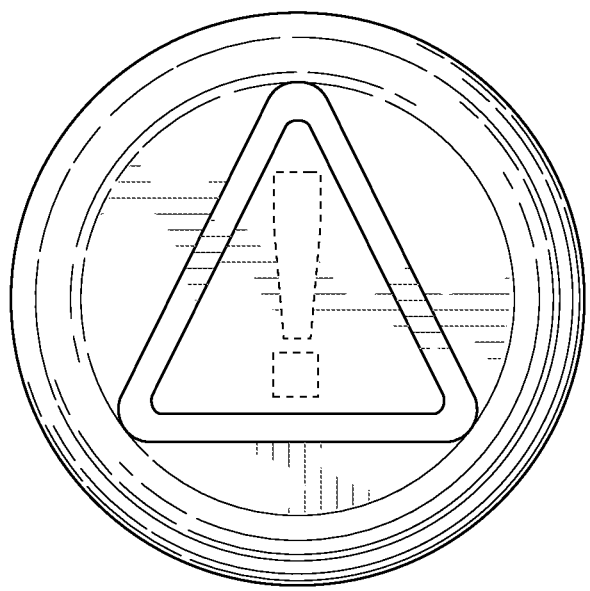
Figure 1G:
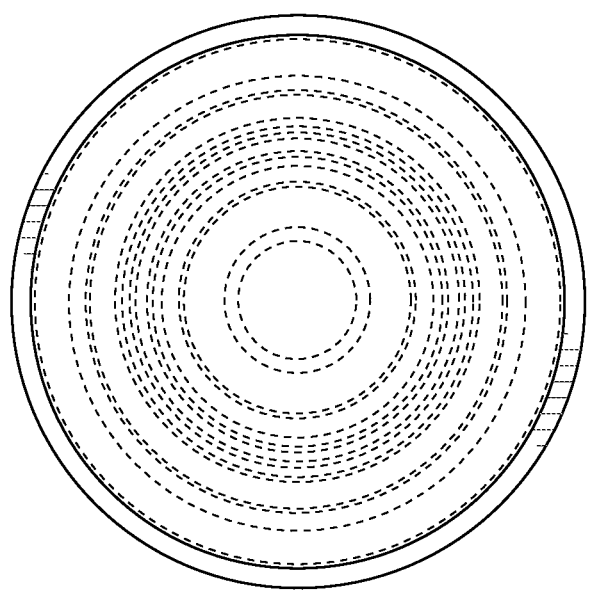
Figure 1H:
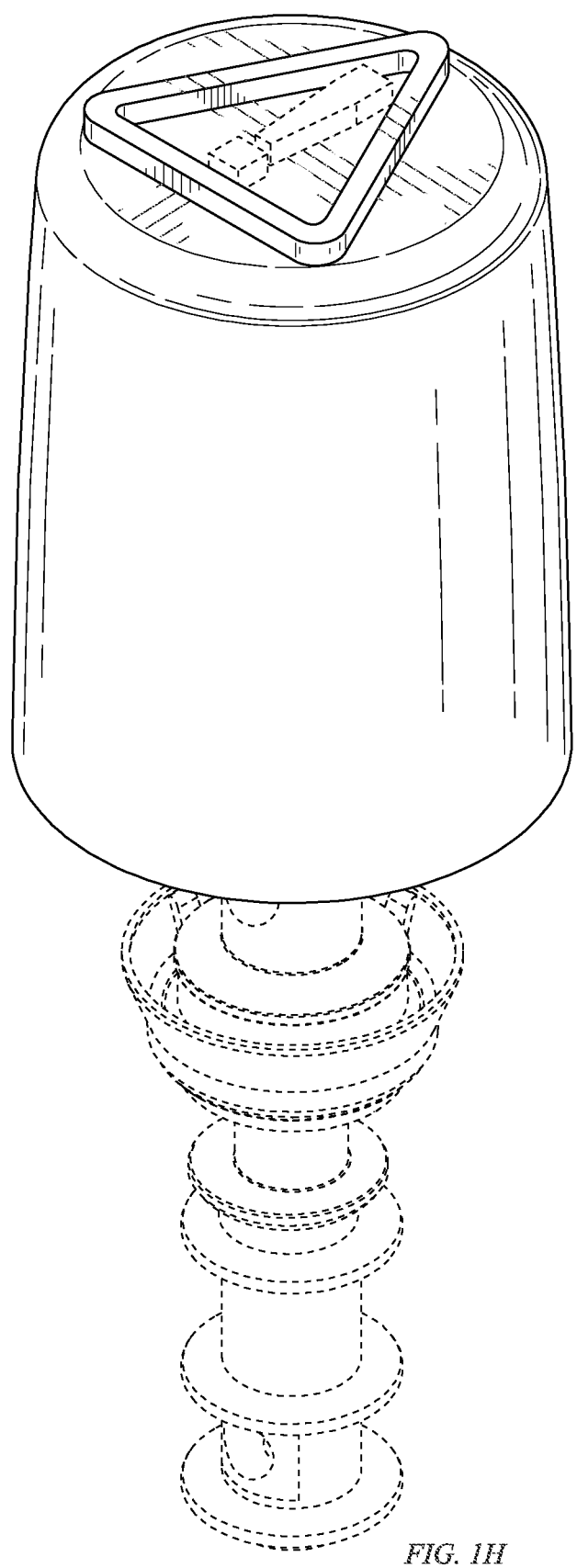

A medical cleaning valve (or cleaning valve) may be configured to provide cleaning functionality to air and water channels of an endoscope. In a first configuration, the cleaning valve may provide a continuous feed of air to both air and water channels in a handle and shaft of an endoscope, and through an air/water nozzle at the distal end of the endoscope. In a second configuration, the cleaning valve may feed water into the air channel in the handle and shaft of the endoscope, and through the air nozzle at the distal end of the endoscope. Oftentimes, cleaning valves may have a similar appearance to procedural valves. However, using a cleaning valve in place of a procedural valve may result in fluid flow through an incorrect endoscope channel, e.g., liquid being delivered through the air channel. Accordingly, one or more embodiments described herein may include cleaning valves with features and/or components that facilitate differentiating them from procedural valves. In at least some embodiments, the cleaning valve (or valve) may be appropriate for single-use and therefore be disposable. Accordingly, the valve may be made from a limited number of parts and materials, e.g., to limit its cost, so that it may be economically disposable. For example, multiple seals may be formed as a single component, such as via overmolding. In another example, wiper seals may be used to accommodate greater manufacturing tolerances. In yet another example, the valve may have a single elastomeric component, or spring cap, which may combine and simplify the functionality of a number of components (e.g., a boot, spring, spring housing, and stem cap).

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface used by an operator for operating a valve (e.g., an interface member, a user interface, a button) and the term "distal" means a direction away from the surface used by an operator for operating a valve (e.g., a button). Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1A-7H illustrate various aspects and/or components of cleaning valve assemblies (or cleaning valves) according to the present disclosure described herein. More specifically, FIGS. 1A-1H illustrate first perspective, front, back, right, left, top, bottom, and second perspective views, respectively, of a cleaning valve assembly 102; FIGS. 2A-2H illustrate first perspective, front, back, right, left, top, bottom, and second perspective views, respectively, of a cleaning valve assembly 202; FIGS. 3A-3H illustrate first perspective, front, back, right, left, top, bottom, and second perspective views, respectively, of a cleaning valve assembly 302; FIGS. 4A-4H illustrate first perspective, front, back, right, left, top, bottom, and second perspective views, respectively, of a cleaning valve assembly 402; FIGS. 5A-5H illustrate a first perspective, left, front, back, right, top, bottom, and second perspective views, respectively, of a cleaning valve assembly 502; FIGS. 6A-6H illustrate first perspective, front, back, right, left, top, bottom, and second perspective views, respectively, of a cleaning valve assembly 602; and FIGS. 7A-7H illustrate first perspective, front, back, right, left, top, bottom, and second perspective views, respectively, of a cleaning valve assembly 702. One or more of the cleaning valves disclosed herein may include features and/or components to facilitate differentiation from procedural valves (i.e., valves for use in a procedure performed on a patient). Further, the features and/or components described herein may be used in any combination to facilitate differentiation from procedural valves. For example, the feel and/or look may be varied from a procedural valve, including a differentiation in shape, color, material, and other visual and/or tactile indicators. In another example, an additional component, such as an indicator, may be included to facilitate differentiation from procedural valves. Embodiments are not limited in this context.

The feel of a valve may be important to where the user will recognize the valve as something they are conditioned to use in a procedure or if the valve is something that feels substantially different than what they are used to. Oftentimes, different valves (both the air water valve, as well as the suction valve) are designed to look and feel substantially similar. This may be done such that the physician does not interpret any tactile difference between different available valves. However, this may lead to confusion between cleaning and procedural valves, which can lead to adverse outcomes. Accordingly, embodiments described herein may have a substantially different feel to the user than a procedural valve, in order to minimize potential incorrect use, e.g., to make it apparent to a user if a procedure is started with the cleaning valve in the air/water valve well rather than the procedural air/water valve. In various embodiments, the interface member or user interface portion (e.g., button or spring cap) of the valve may be constructed out of a substantially different material. For example, a soft, tacky, and/or flexible material such as a silicone elastomer or thermoplastic elastomer (TPE) may form a soft and/or tacky user interface surface of the valve that interacts with a user (e.g., finger/hand of the user). In such examples, this soft, tacky, and/or flexible feel may differentiate the cleaning valve from rigid molded plastic valve buttons of procedural valves. In various embodiments, the soft, tacky, and/or flexible feel may be applied to selective components of the cleaning valve. For instance, a first raised surface may be tacky, a second raised surface may have a rough texture, and another surface may be smooth.

In many embodiments, features may be added to the user interface of the valve to differentiate the feel of the valve when compared to procedural valves. Procedural valves typically have smooth flat circular user interface surfaces that interact with a user when the valves are depressed. However, one or more embodiments described herein may have user interface surfaces that feel substantially different when depressing the valve. For example, the user interface surface may include a multitude of small protrusions from the surface in the form of cones, rods, bumps, loops, ridges, or any other three-dimensional textured surface that can cause the user to notice they are not pressing on a smooth surface.

In several embodiments, the interface member or user interface (e.g., button or spring cap) may be shaped to differentiate the feel of the cleaning valve when compared to procedural valves. For example, the user interface may include a geometric shape to interact with the user that has pronounced corners that could be felt during depression of the user interface, such as a circle, triangle, square, rhombus, hexagon, or any other shape that would have a distinct or pronounced edge when compared to a circle. When depressed these shapes may feel substantially different than a circular button used on procedural valves with a smooth radius on the edge of the valve.

In some embodiments, the user interface (e.g., button or spring cap) may be sized to facilitate distinction from procedural valves. Many procedural valves are roughly half an inch in diameter on the user interface surface (e.g., proximal side of the button). However, making the size of the user interface surface the user presses substantially larger or substantially smaller can allow the user to notice a size difference in the surface they are pressing, further differentiating the cleaning valve from the procedural valve. This size difference may include one or more of the surface area of the user interface surface being depressed, as well as the height that the surface sits above the endoscope handle when inserted into the air/water well. For instance, a substantially shorter or substantially taller surface may require the user to move their hands/fingers in a manner that they are not used to in order to operate the valve, again drawing further attention to the fact that this is not a typical procedural valve. For optimal differentiation, a valve may include any combination of the above-mentioned features and/or techniques of differentiating the look and/or feel of a cleaning valve from procedural valves.

In several embodiments, the look or appearance of a cleaning valve may be used to differentiate the feel of the valve when compared to procedural valves. Many procedural valves are primarily all black buttons, with a cylindrical collar that snaps onto the valve well and a cylindrical button with a flat button surface. By substantially changing the appearance of the cleaning valve from a procedural valve, a user may have their attention better drawn to it when they see one inserted in the air/water valve well of an endoscope handle. The appearance of the cleaning valve may be differentiated by including one or more of the following.

In some embodiments, color selection of one or more components of the cleaning valve may be used to differentiate the look of the cleaning valve when compared to procedural valves. In many embodiments, the colors may be selected to provide contrast to the black endoscope handle and/or black procedural valves that blend in with the endoscope handle. For example, using one or more bright or neon colors, such as yellow, orange, red, and pink, on one or more components of a cleaning valve assembly may be used to differentiate the valve visually. In another example, a clear or "natural" silicone elastomer color or TPE color may be used. This clear color may leave a translucent appearance that is clearly noticeable when looking at the valve in an endoscope handle. In some embodiments, reflective or glitter surfaces may be used.

Differentiating the valve by feel may also differentiate the valve by look. For instance, changing the shape of the valve user interface (e.g., button or spring cap) from circular to some other geometric shape would allow for visual differentiation in addition to feel differentiation, especially when combined with a substantially different color/pattern like described above. Making the interface a triangle shape, square shape, rhombus shape, hexagonal, or any other shape with sharp angular edges may provide visual and tactile differentiation of the valve from a circular procedural valve.

Typically, air/water and suction procedural valves used (whether disposable or re-usable versions) may have the same combination of a button surface to be depressed which slides inside of a collar component that attaches to the scope. By changing this configuration such that the same two components with the same type of interaction are no longer present may further help differentiate a cleaning valve from procedural valves. In various embodiments, switching the way the button component and collar component interact may be used to differentiate the valve. For example, the button may be a skirt that slides over the outside of the collar component. In such examples, this may change the overall shape of the user interface significantly compared to the button of procedural valves. In some embodiments, the shape and component interaction may be changed to eliminate separate button and collar components altogether, such as by having a single seamless spring cap that both connects to the valve well as well as the top of the valve stem fully enclosing the entire valve from the outside. This, along with a soft flexible material, and/or different colors may substantially differentiate the valve from procedural valves.

Figure 2A:
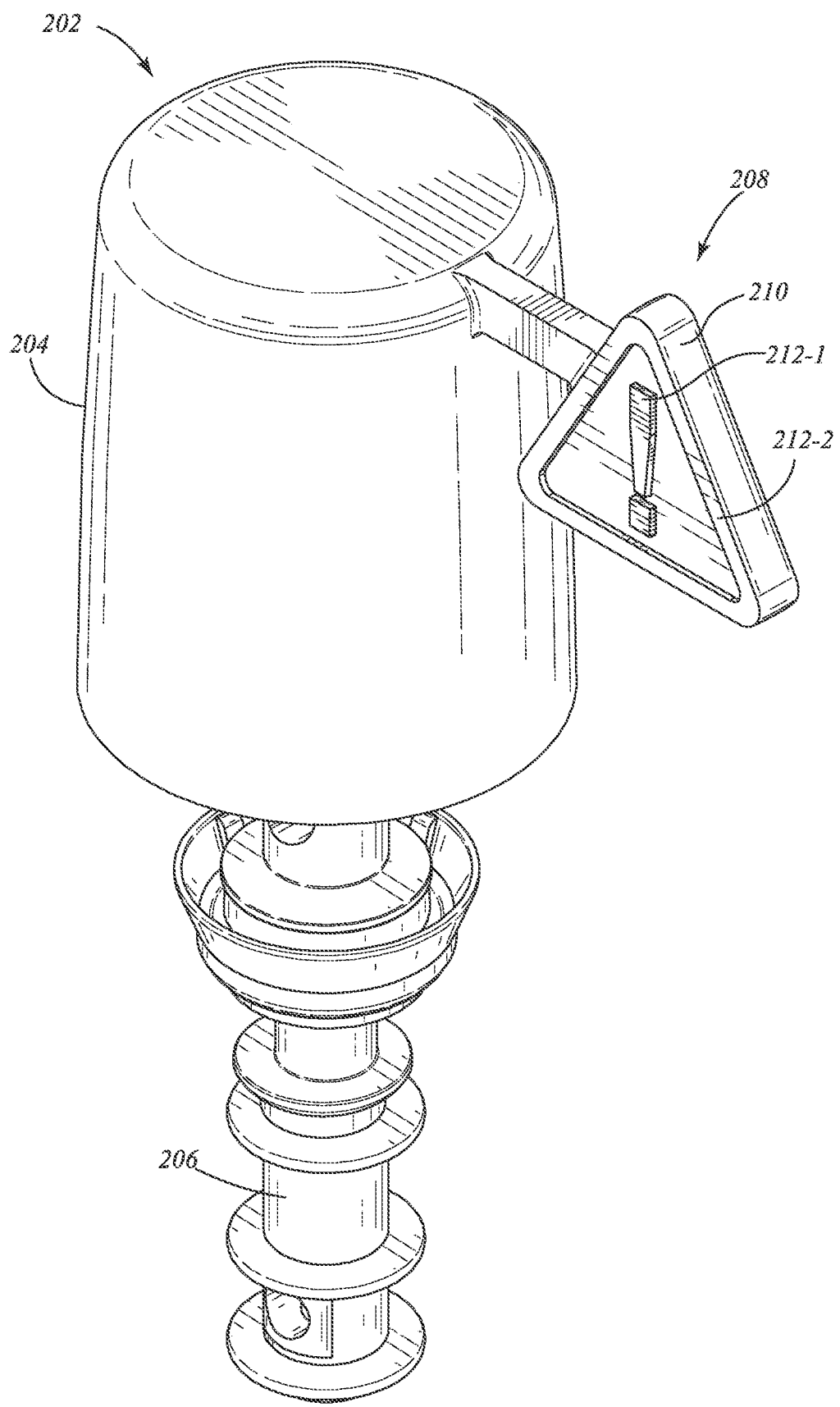
FIGS. 2A-2H illustrate first perspective, front, back, right, left, top, bottom, and second perspective views, respectively, of an exemplary embodiment of a medical cleaning valve assembly according to the present disclosure described herein.
Figure 2B:
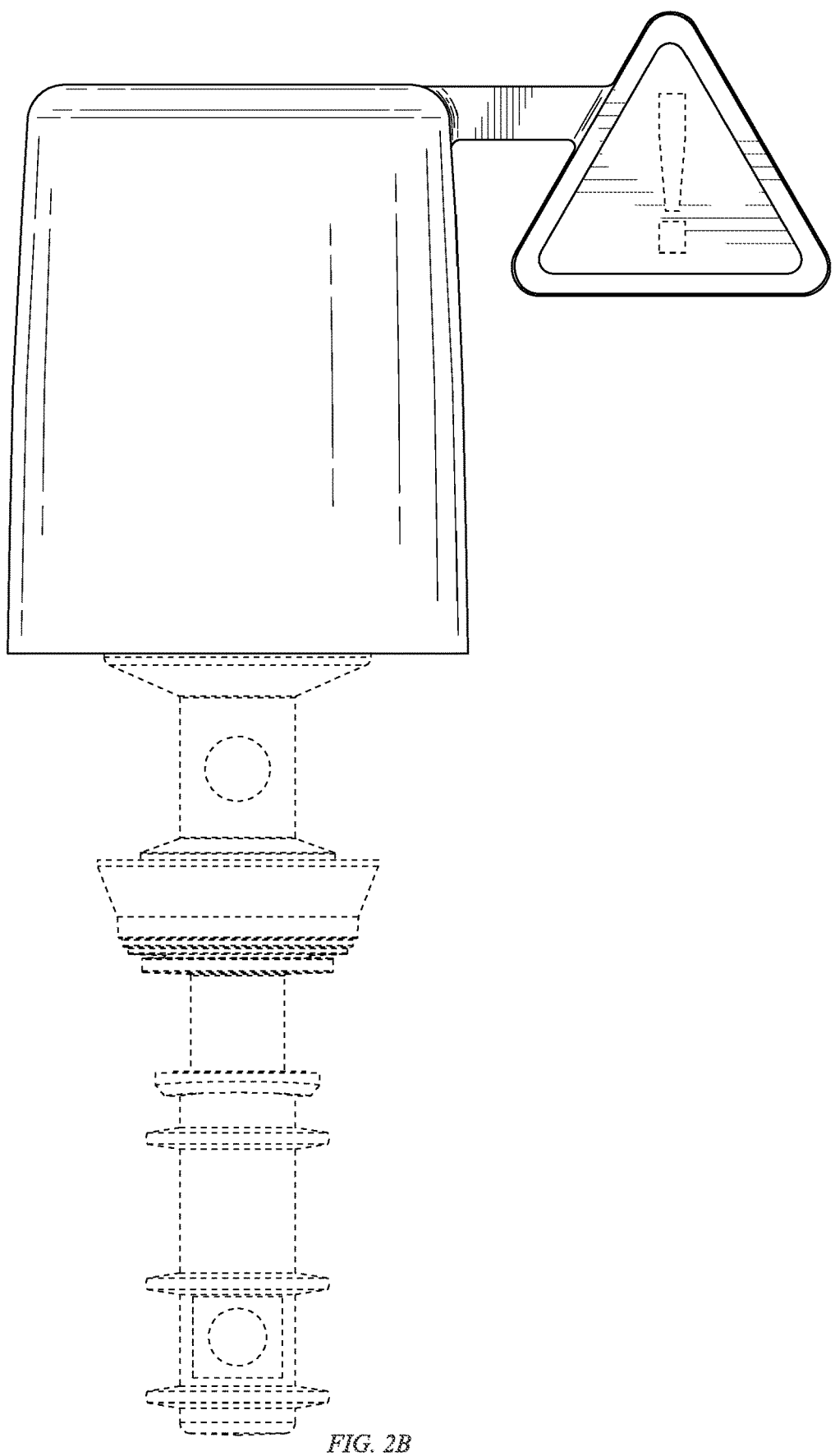
Figure 2C:
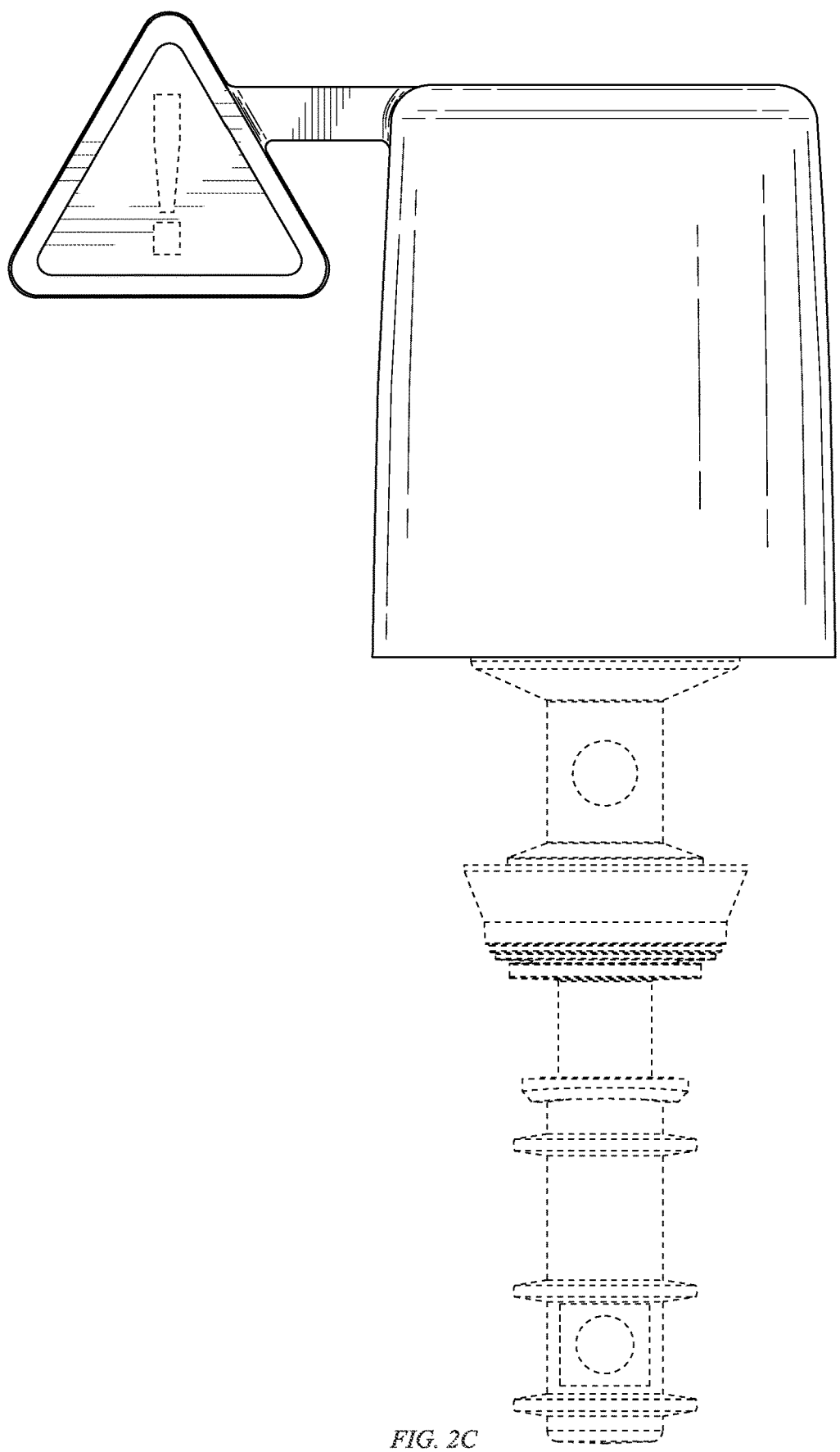
Figure 2D:
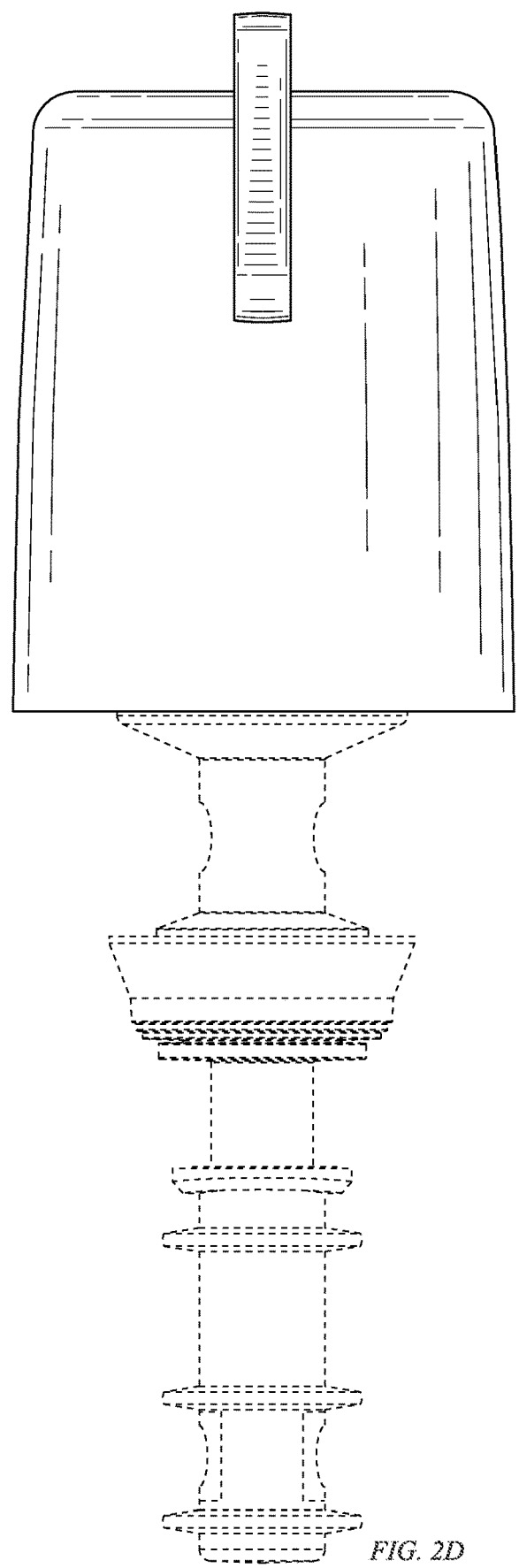
Figure 2E:
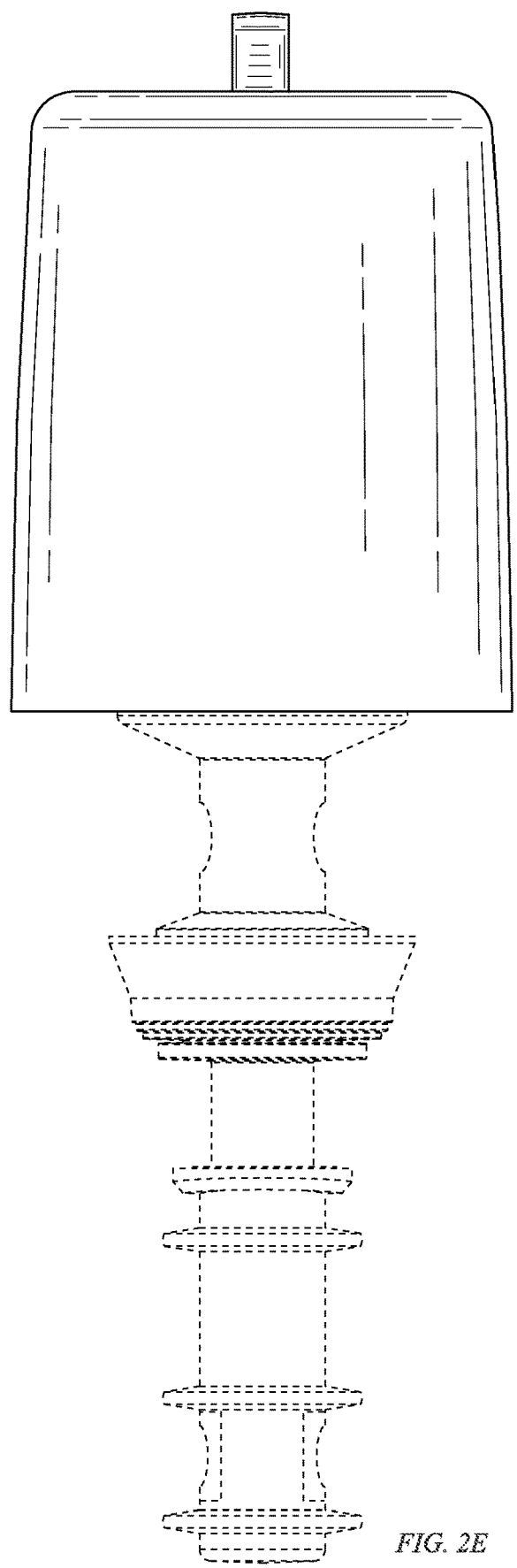
Figure 2F:
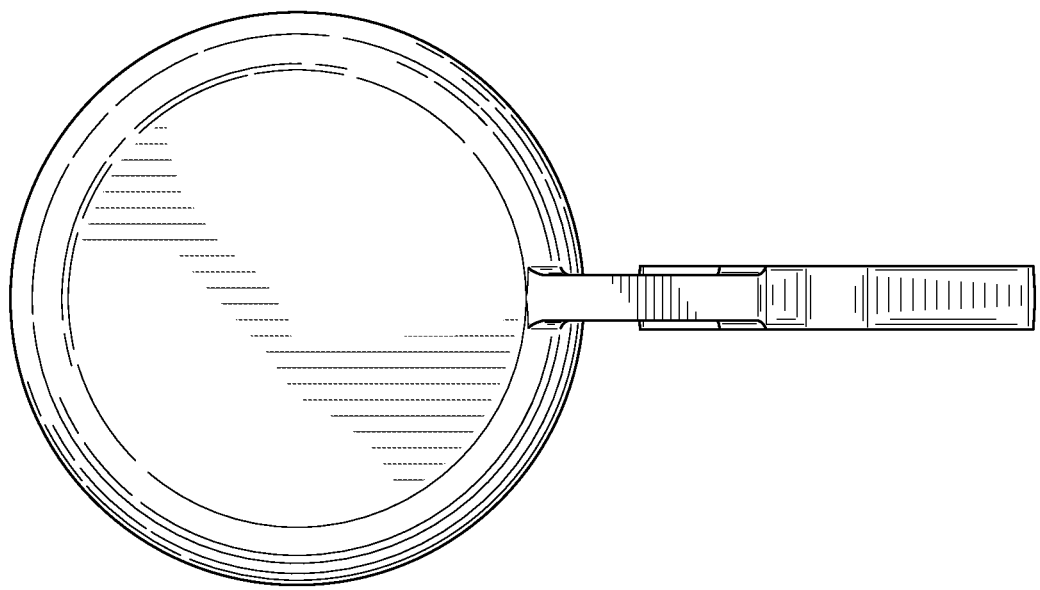
Figure 2G:
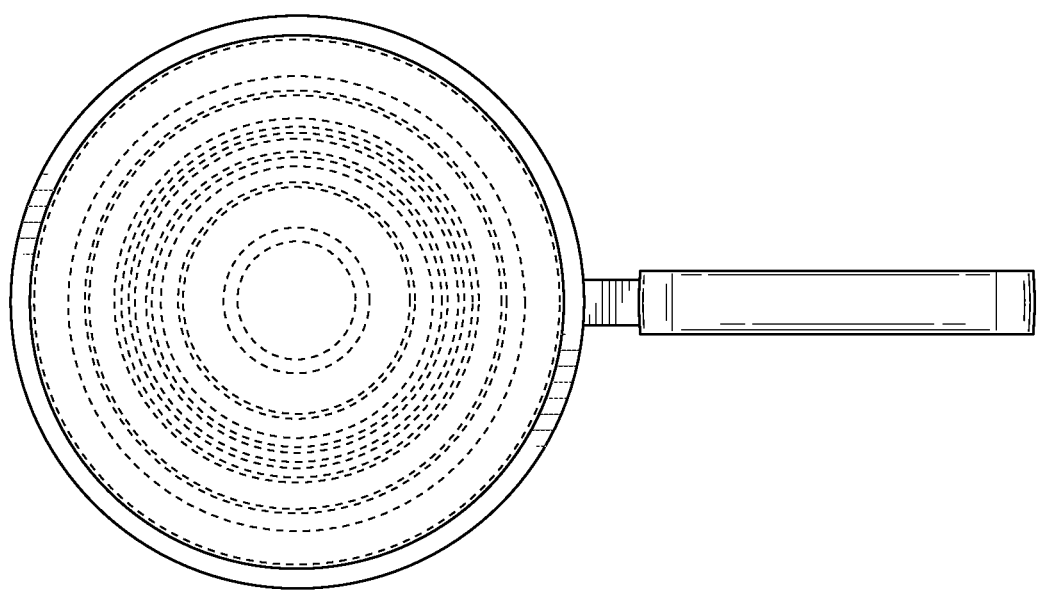
Figure 2H:
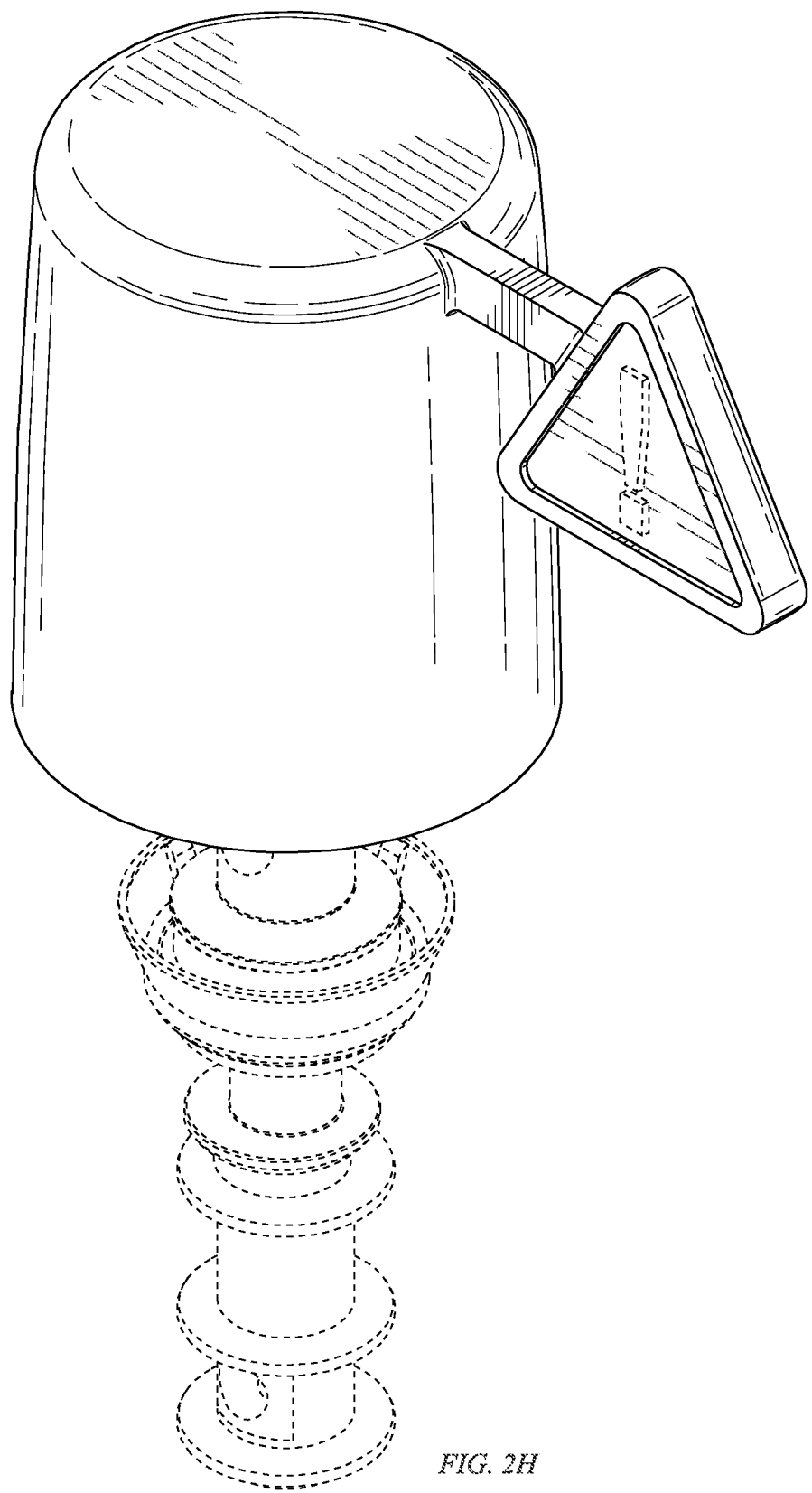
Figure 3A:
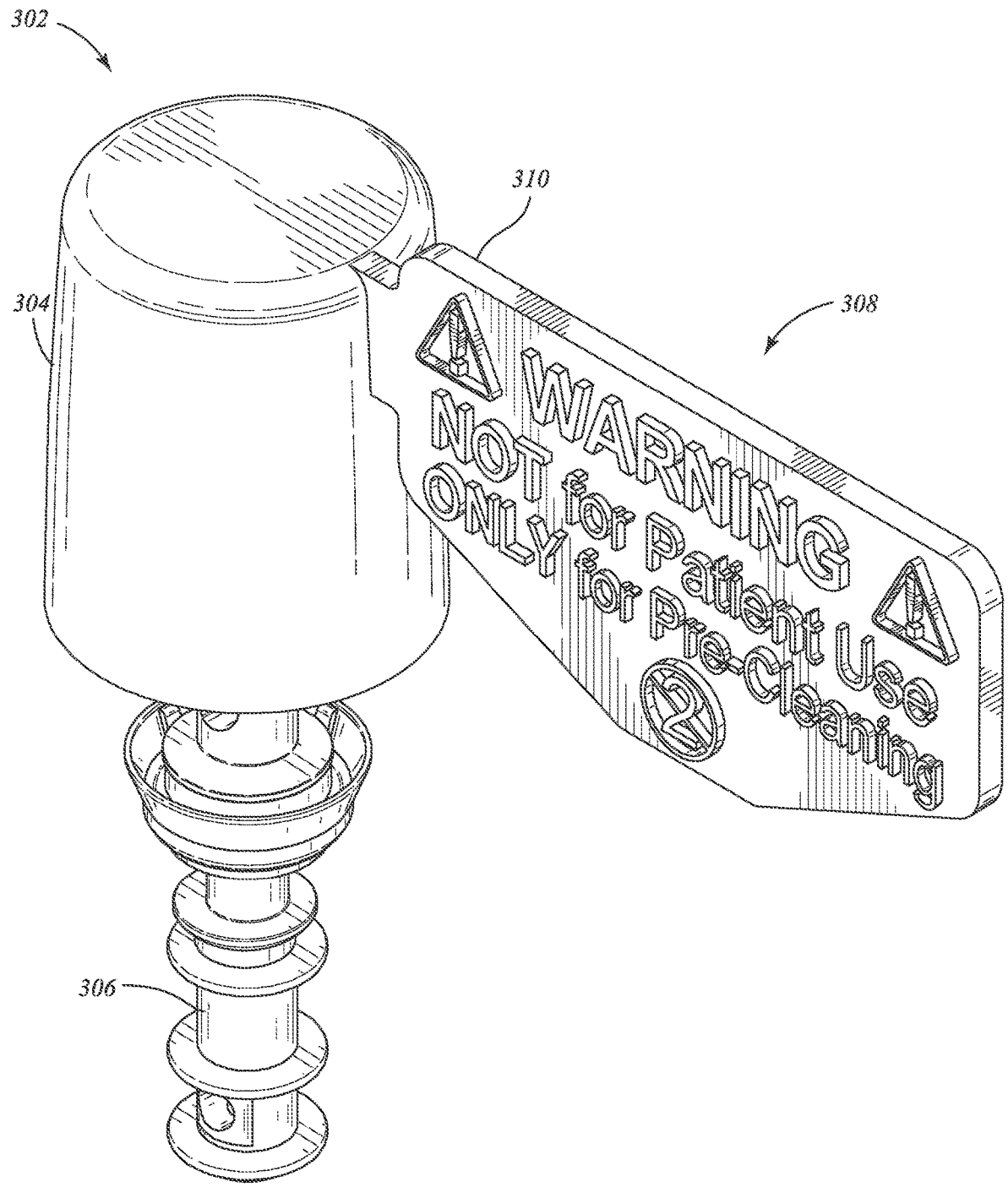
Figure 3B:
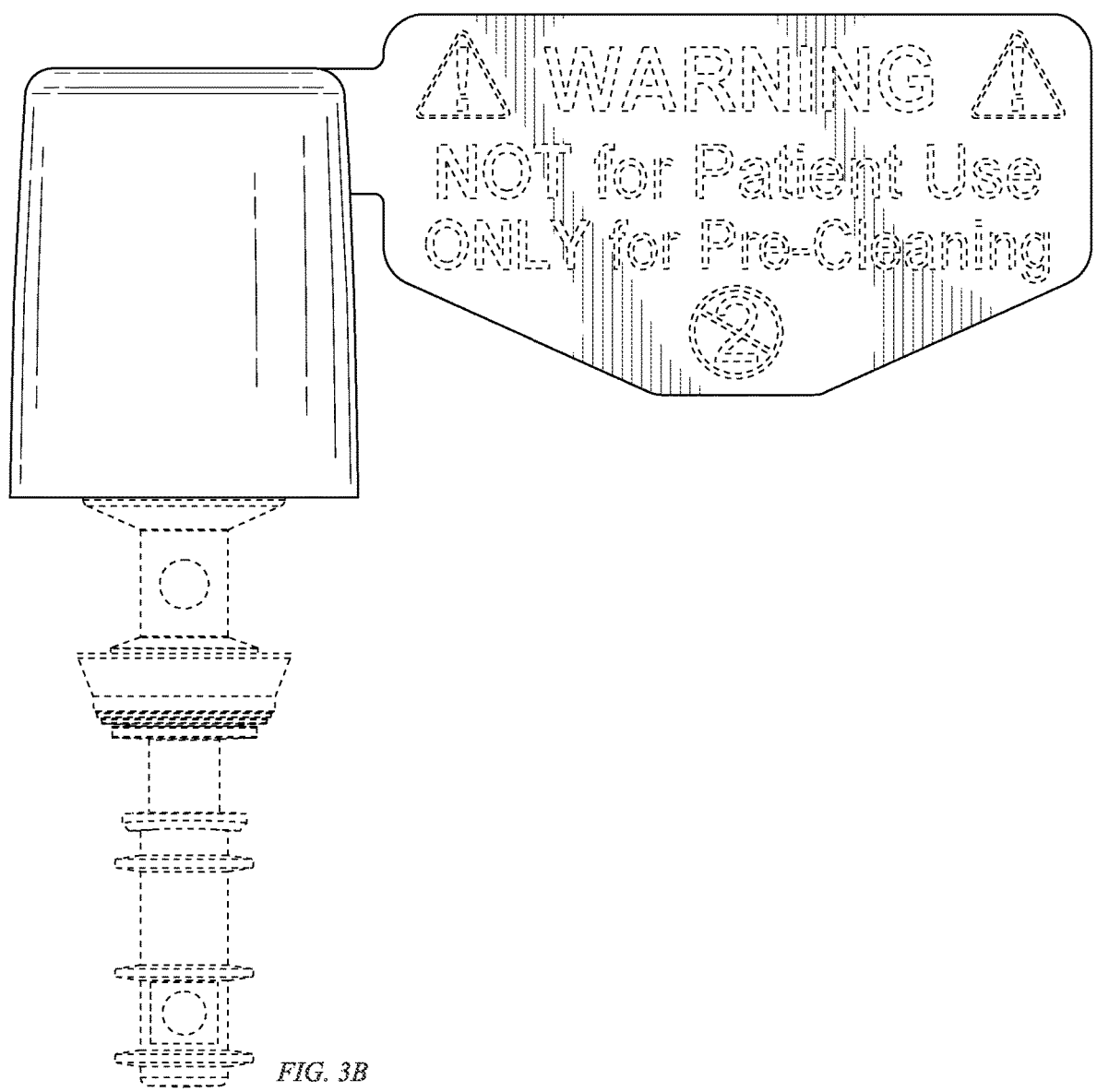
Figure 3C:
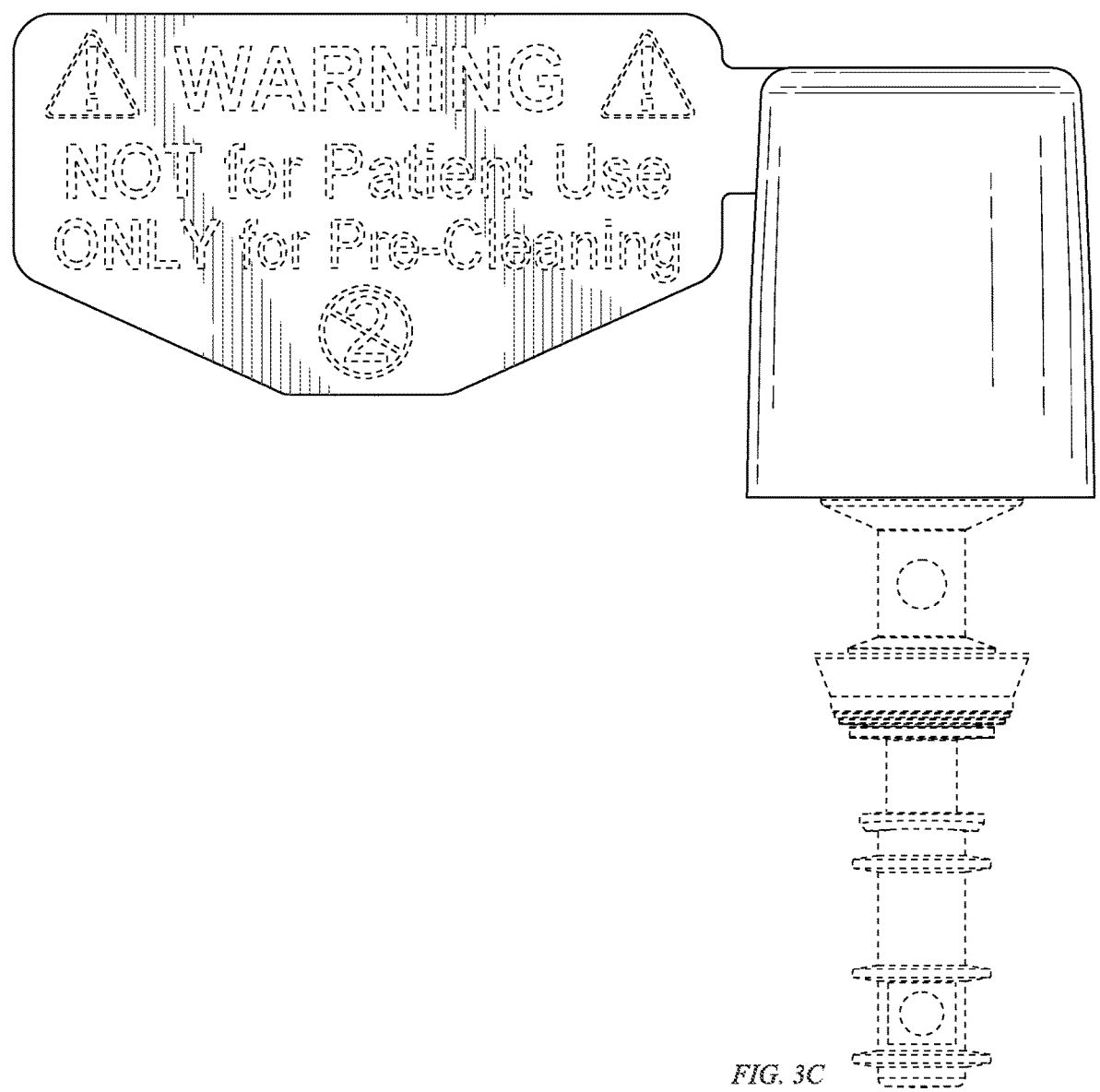
Figure 3F:
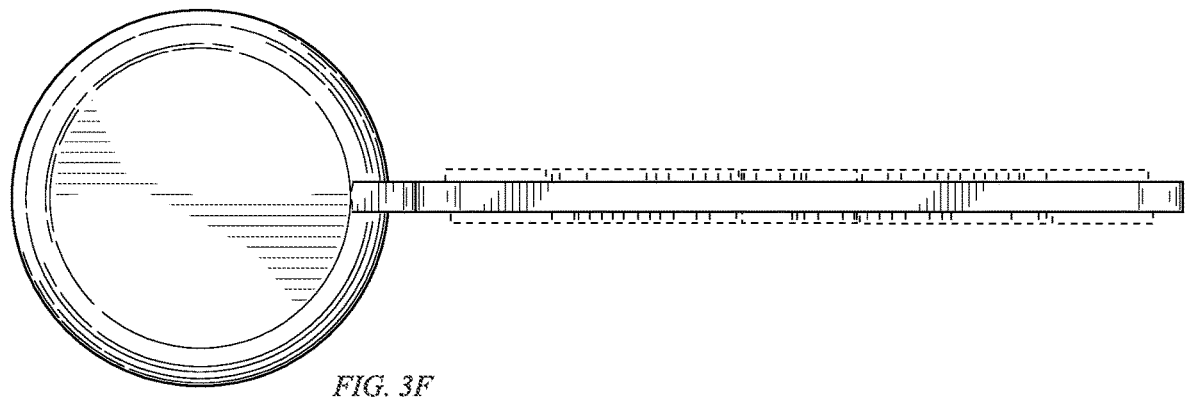
Figure 3G:
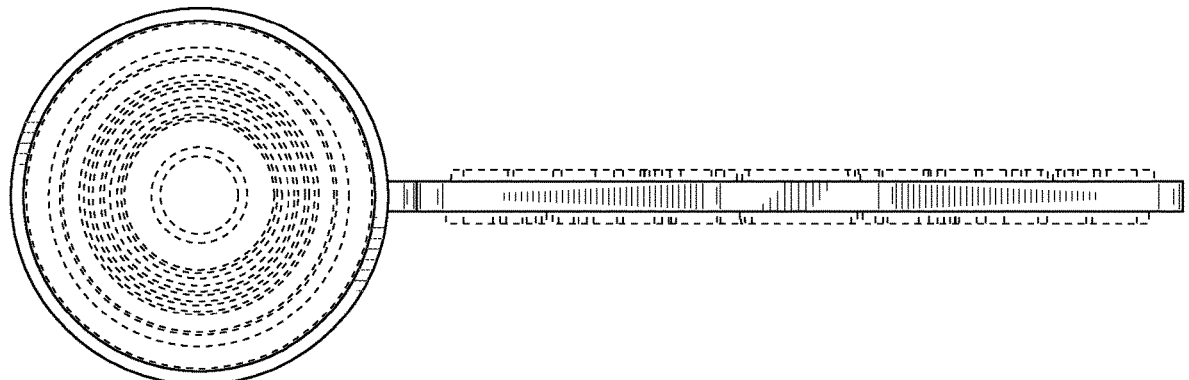
Figure 3H:
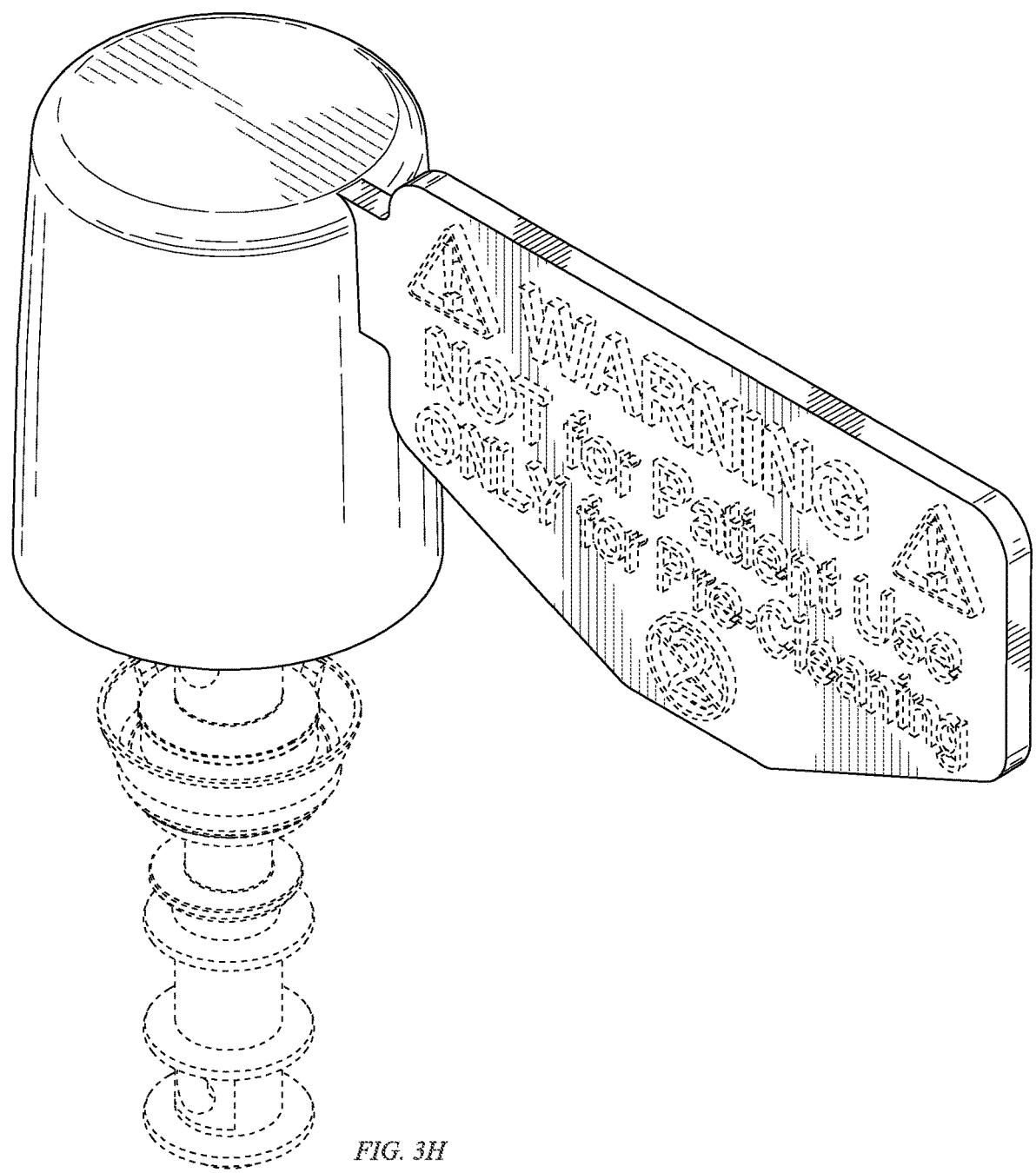

In several embodiments, an indicator (e.g., warning) of some kind may be included in or on the valve. For example, ways of including a warning on the valve for differentiating a cleaning valve from a procedural valve could include pad printing or laser etching a warning directly onto the user interface (e.g., spring cap or button) or exposed surface of the cleaning valve during use. Alternatively, or additionally, a warning label could be embossed on the side of the user interface (e.g., spring cap or button), providing a warning that protrudes out from the side of the valve and is felt and clearly visible during use. This could be located on the side of the valve, or on the top surface forcing the user to feel the warning when they depress the valve. An example of this can be seen in FIG. 1A. Alternatively, or additionally, a warning tag could be molded into the interface member and integrally attached as part of the component as seen in FIGS. 2A and 3A. In some embodiments, the tag may be removably attached to the interface member. As will be appreciated, the text and/or symbols may be varied (as long as they facilitate differentiation from a procedural valve) without departing from the scope of this disclosure.

In addition, or alternatively, to the cap color changing, the color of one or more other components may be changed to differentiate from a procedural valve. For example, the valve stem color may be substantially different than procedural valve stems. In some embodiments, the seal colors can be a bright color (e.g., yellow) on the stem, or a combination of any other colors, that draws the attention of a user to the fact that the valve is for cleaning. As well, the valve stem itself can be colored or patterned substantially different than the procedural valves, which may be a stainless-steel natural color. In various embodiments, a combination of natural color elastomer spring cap, with natural color seals and a yellow stem may be used, but any distinct combination such as yellow stem and seals, blue seals and yellow stem, pink stem and yellow seals, or the like may be used. Additionally, the cap could have a raised feature molded in, such as circumferentially around its base, and/or have pad printing circumferentially with writing indicating a warning or some type of instructions for use. In many embodiments, the user may be able to read a warning on the cap without actually having to have a separate warning tag attached as it would be directly printed or visible as part of the cap itself.

In many embodiments, there may be an additional component that slides over or removably attaches to the seal end of the valve stem in the packaging with a shape that prevents the valve from being inserted into the valve well of the endoscope without the additional component first being removed. See e.g., FIGS. 4A-7H. In many embodiments, a portion of this component may be inserted through a radial hole, orifice, or aperture of the valve stem. See e.g., FIGS. 4A-4H. In various embodiments, this component may clip to the valve stem. See e.g., FIGS. 5A-5H. In some embodiments, this component could be hollow with an inside diameter large enough to slide over the end of the valve stem and an outside diameter large enough such that it has an interference fit with the valve well on the scope so it is unable to be inserted. See e.g., FIGS. 6A-7H.

In various embodiments, this component could be a molded component made of a bright color material to further draw attention to it. In many embodiments, it must be removed from the valve prior to being able to insert the valve into the endoscope. This may ensure the user must complete an additional step prior to being able to insert the cleaning valve into the endoscope further drawing attention that the valve is not a procedure valve. This component could also be a clip style component that clips onto the valve stem from the side, again causing interference with the valve well if a user attempts to insert the valve prior to removal. The clip tag or the tag that slides over the end of the valve stem (i.e., barrel tag) could also have a molded tag off the side with embossed lettering or pad printed lettering. See e.g., FIG. 6A. In some embodiments, this verbiage could also act as a warning tag, not only informing the user of the intended "cleaning" use, but also requiring the user to remove the warning prior to insertion in the valve well, forcing them to focus their attention on it for some time prior to attempting to insert the valve into the scope.

Referring specifically to FIG. 1A, cleaning valve assembly 102 (or cleaning valve 102) may include an interface member 104 with a first indicator 108, a valve stem 106, a proximal end 145, and a distal end 155. In various embodiments, cleaning valve assembly 102, or one or more components thereof, may be the same or similar to other cleaning valve assemblies, or one or more components thereof, described herein. For example, cleaning valve assembly 102 may be the same or similar to cleaning valve assembly 1502 of FIG. 15. It will be appreciated that the orientation of other cleaning valves and/or cleaning valve components described herein will remain consistent with the orientation of cleaning valve 102 with respect to proximal and distal ends 145, 155. The interface member 104 may include a proximal surface 111-1 and a radial surface 111-2. The proximal surface 111-1 of interface member 104 may include indicator 108 comprising raised surfaces 112-1, 112-2. More generally, indicators described herein may include one or more raised surfaces with various features (e.g., texture, color, tackiness, or the like) configured to differentiate a cleaning valve from a procedural valve.

In indicator 108, raised surface 112-2 may surround raised surface 112-1. In one or more embodiments, raised surface 112-1 may be a symbol and raised surface 112-2 may be a geometric shape, such as a triangle, a square, a rhombus, a hexagon, or similar, surrounding the symbol. For example, raised surface 112-1 may be an exclamation point and raised surface 112-2 may be a triangle surrounding the exclamation point. In various embodiments, one or more of proximal surface 111-1, radial surface 111-2, and raised surfaces 112 may include one or more textures to differentiate cleaning valve 102 from a procedural valve. For instance, proximal surface 111-1 and radial surface 111-2 may be smooth while raised surface 112-1 has a texture comprising a multitude of cones and raised surface 112-2 has a texture comprising a multitude of bumps. Additionally, or alternatively, one or more of the surfaces may comprise a tacky material. For instance, raised surfaces 112 may be tacky while proximal and radial surfaces 111-1, 111-2 have non-tacky surfaces.

Referring specifically to FIG. 2A, cleaning valve assembly 202 (or cleaning valve 202) may include an interface member 204 with an indicator 208 and a valve stem 206. In various embodiments, cleaning valve assembly 202, or one or more components thereof, may be the same or similar to other cleaning valve assemblies, or one or more components thereof, described herein. For example, cleaning valve assembly 202 may be the same or similar to valve 10 of FIG. 8. All though not labeled, interface member 204 may include proximal and radial surfaces similar to interface member 104. The indicator 208 may comprise a tag 210 with raised surfaces 212-1, 212-2. The indicator 208 may be integrally attached (e.g., molded therewith) to the interface member 204. In many embodiments, indicator 208 extends laterally from the interface member 204 between the distal and proximal ends of interface member 204. For example, in the illustrated embodiment, indicator 208 extends laterally from the interface member 204 proximate the juncture of the proximal and radial surfaces. In some embodiments, an indicator and/or tag may extend horizontally, proximally, distally, or any angle in between, from the proximal and/or radial surfaces of an interface member.

Referring specifically to FIG. 3A, cleaning valve assembly 302 (or cleaning valve 302) may include an interface member 304 with an indicator 308 and a valve stem 306. In various embodiments, cleaning valve assembly 302, or one or more components thereof, may be the same or similar to other cleaning valve assemblies, or one or more components thereof, described herein. For example, valve stem 306 may be the same or similar to valve stem 1906 of FIG. 19. All though not labeled, interface member 304 may include proximal and radial surfaces similar to interface member 104. The interface member 304 may include an indicator 308 comprising a tag 310 with a plurality of raised surfaces (e.g., each letter can be considered a separate raised surface). The indicator 308 may be integrally attached (e.g., molded therewith) to the interface member 304. In many embodiments, indicator 308 extends laterally from the interface member 304 between the distal and proximal ends of interface member 304. For example, in the illustrated embodiment, indicator 308 extends laterally from the interface member 304 proximate the juncture of the proximal and radial surfaces.

Figure 4A:
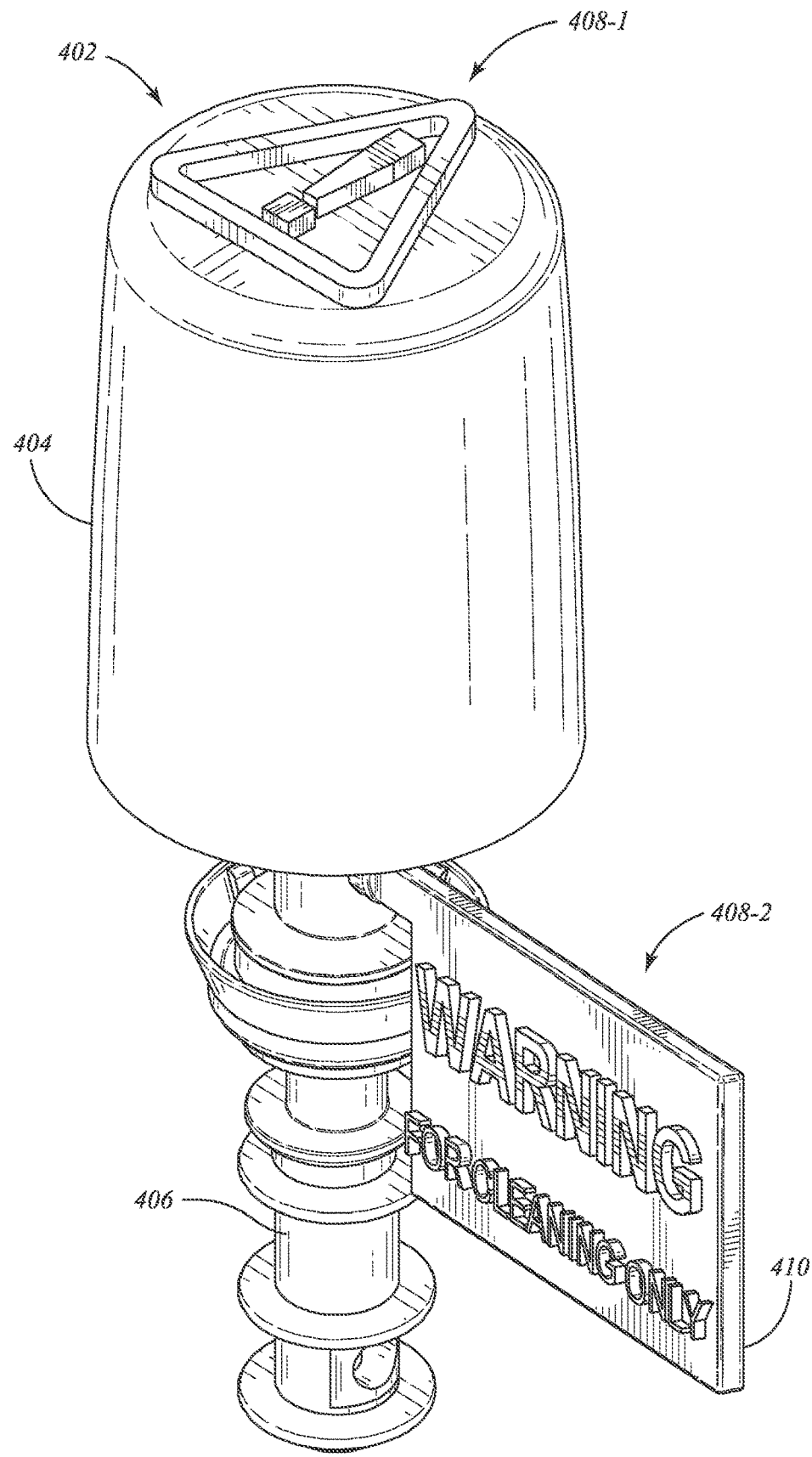
FIGS. 4A-4H illustrate first perspective, front, back, right, left, top, bottom, and second perspective views, respectively, of an exemplary embodiment of a medical cleaning valve assembly according to the present disclosure described herein.
Figure 4B:
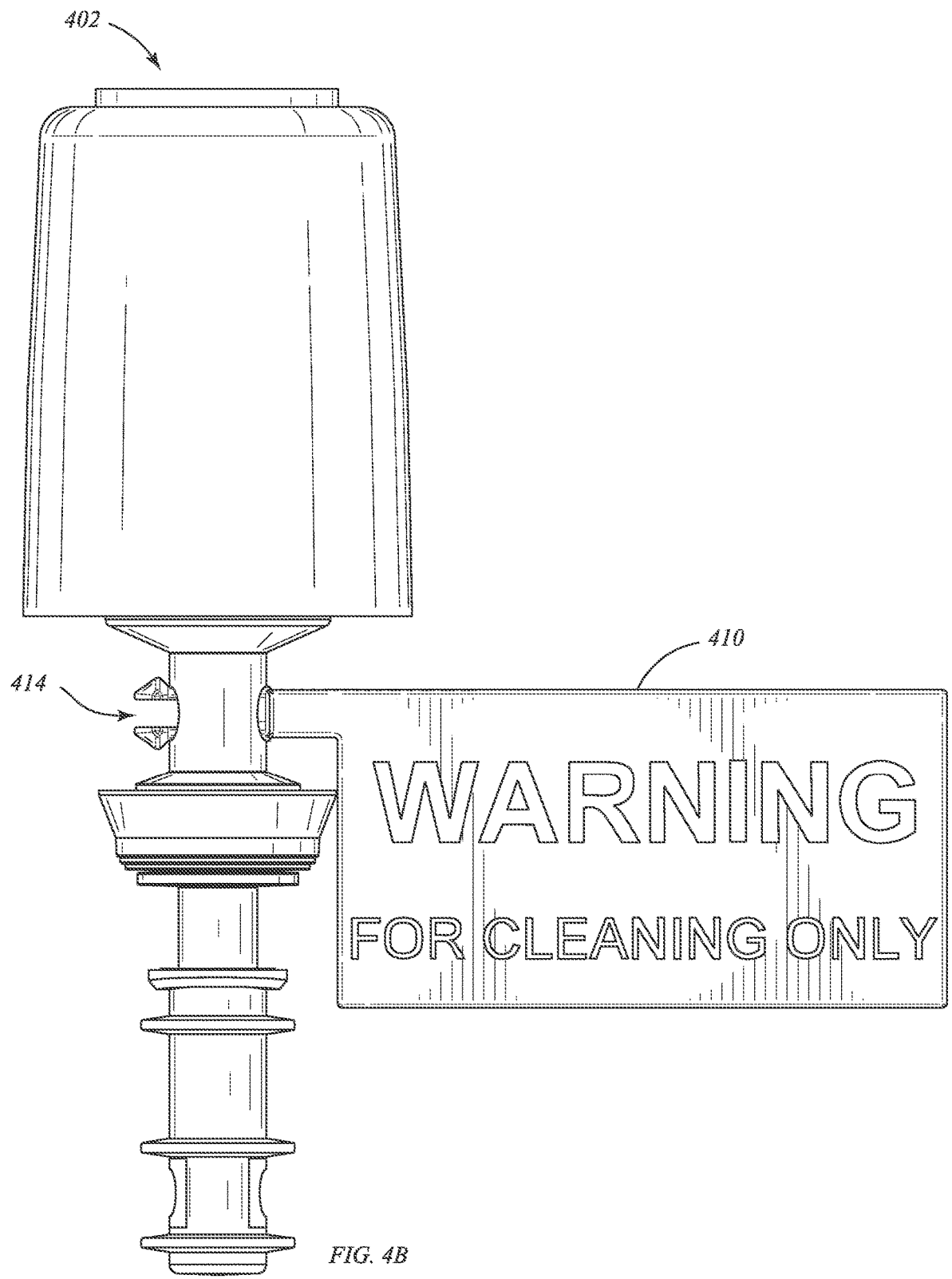
Figure 4C:
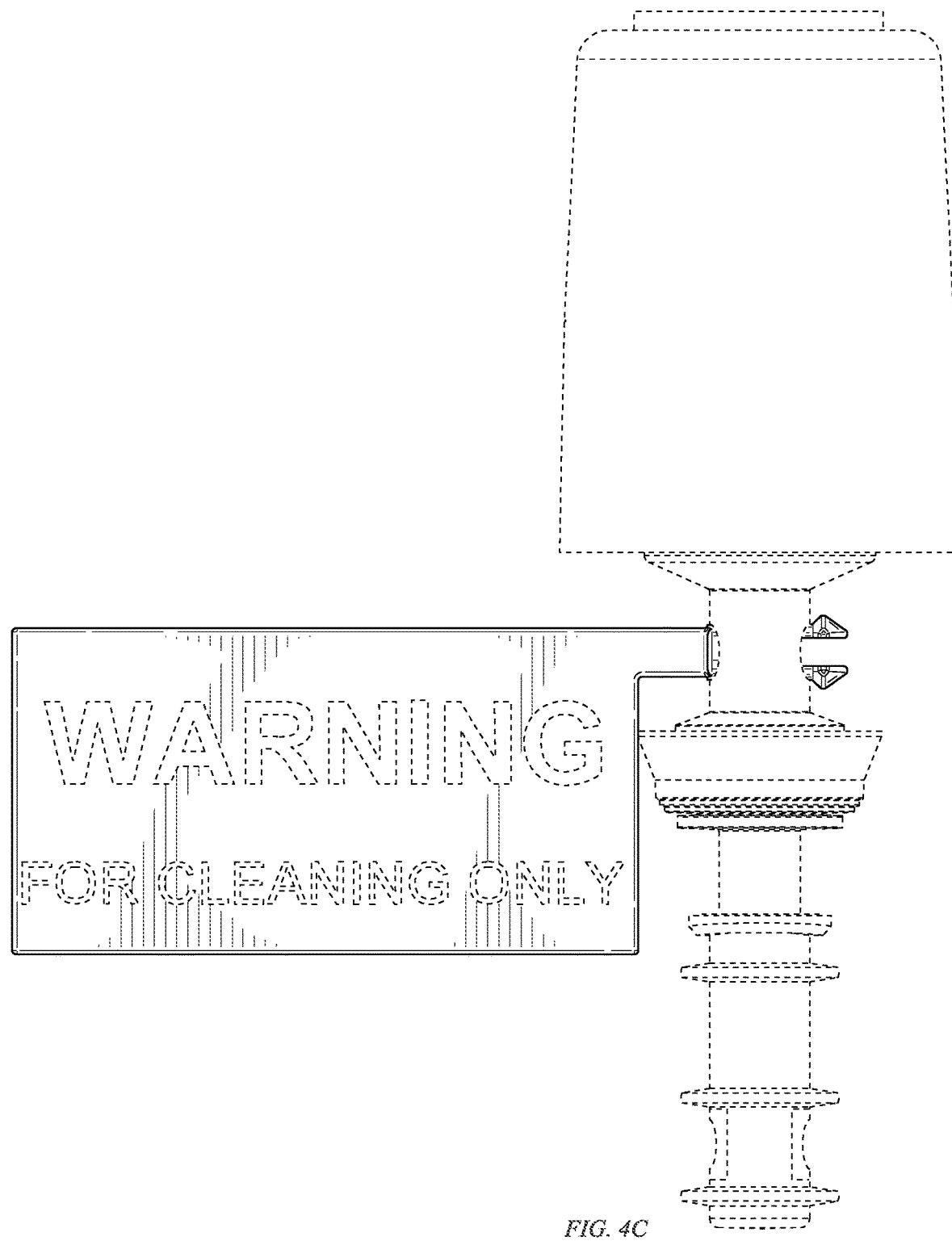
Figure 4D:
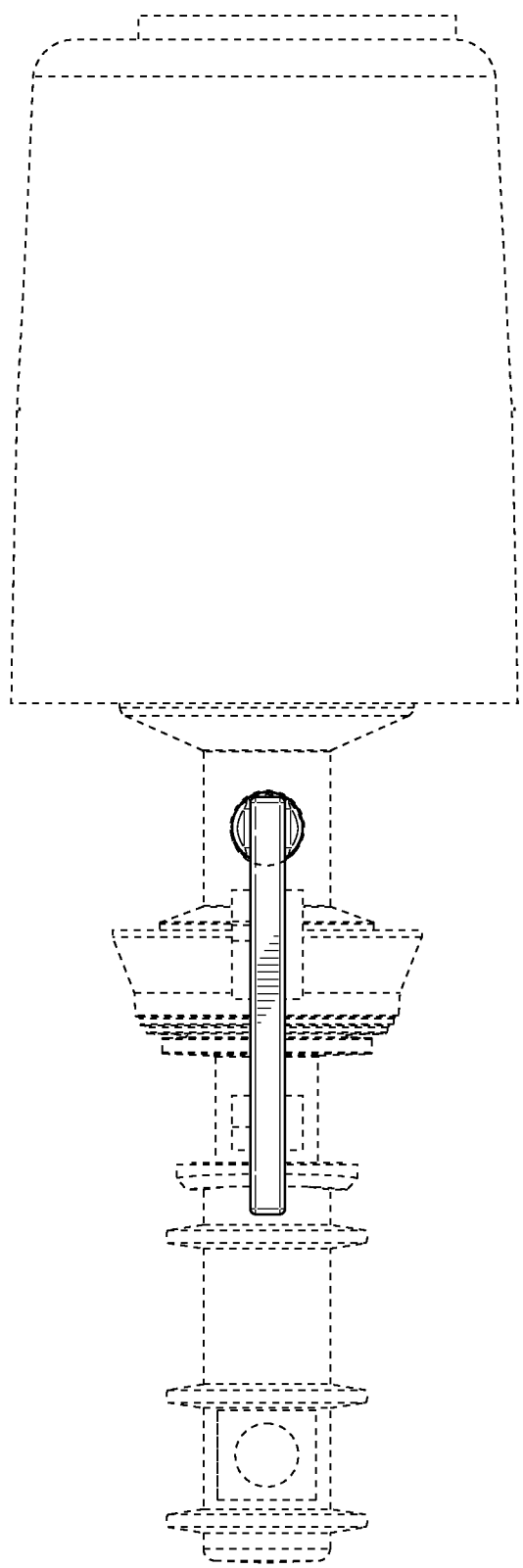
Figure 4E:
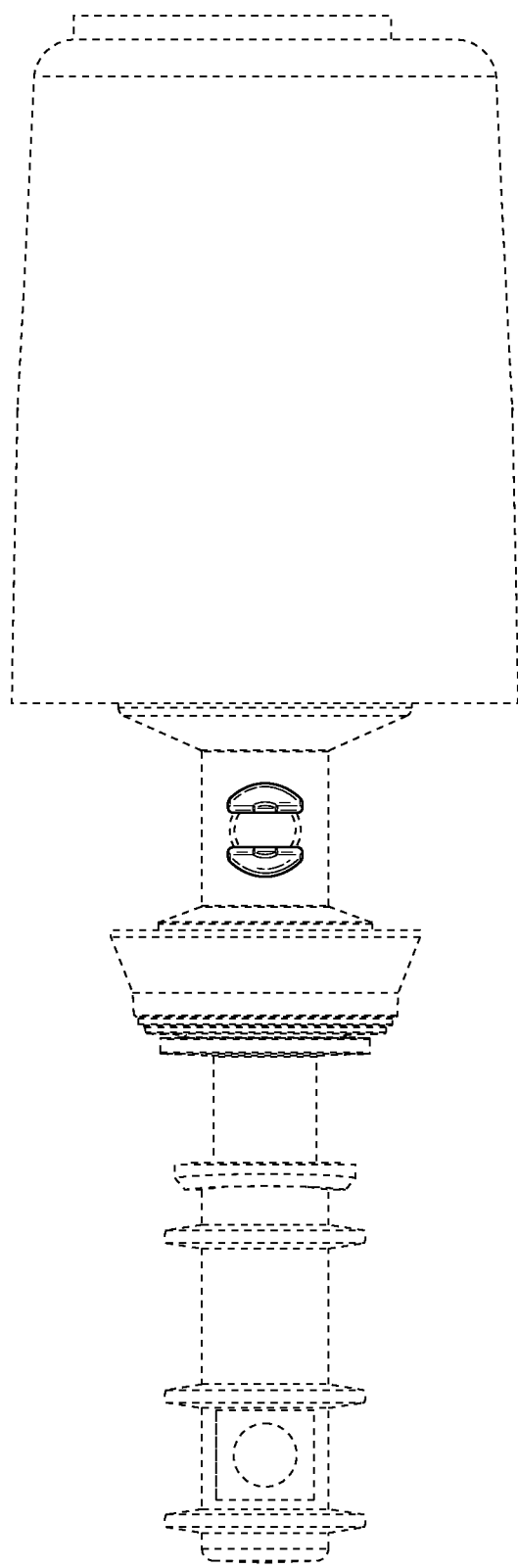
Figure 4F:
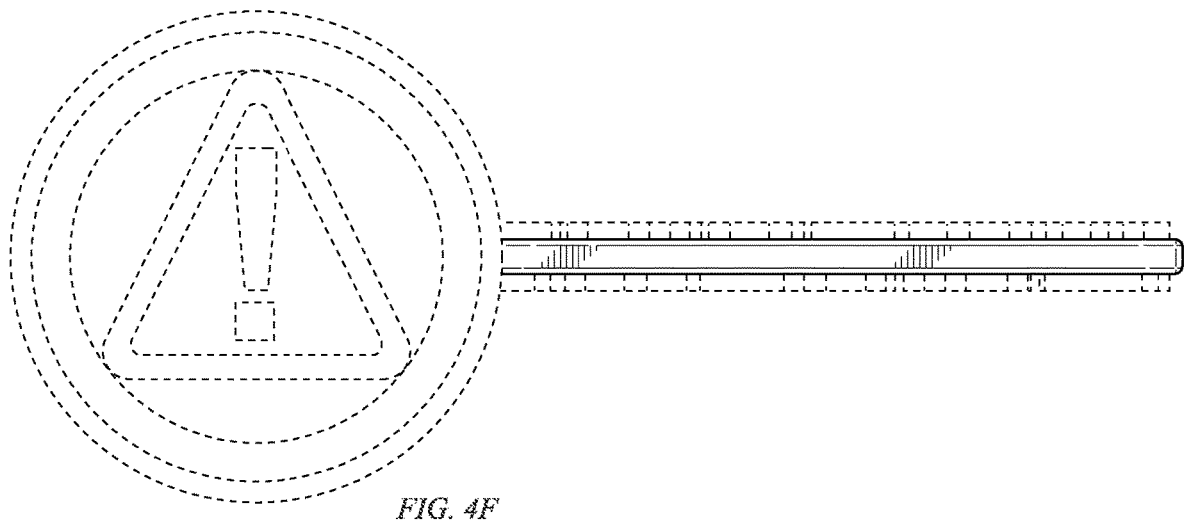
Figure 4G:
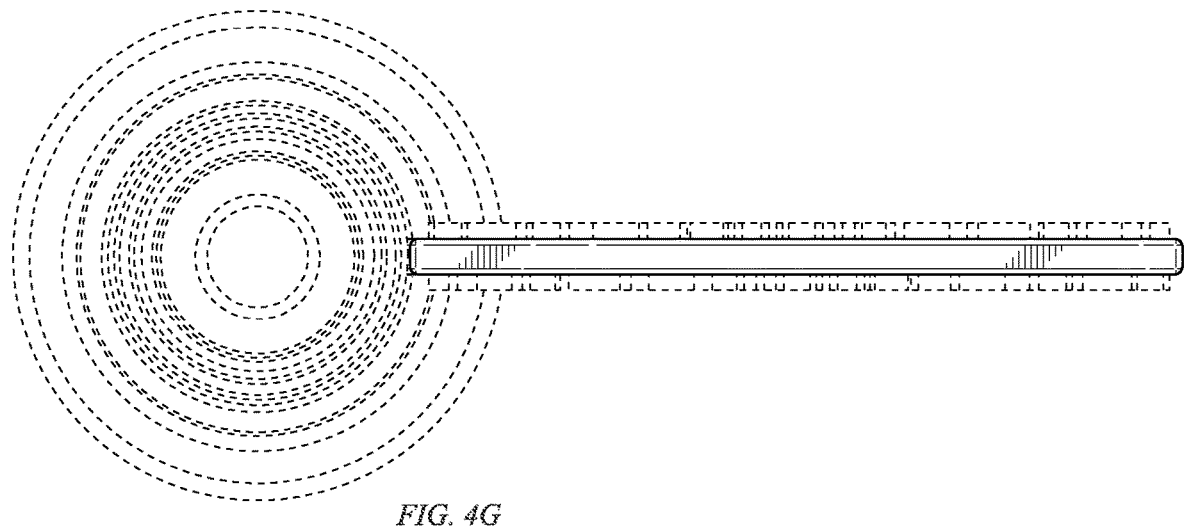
Figure 4H:
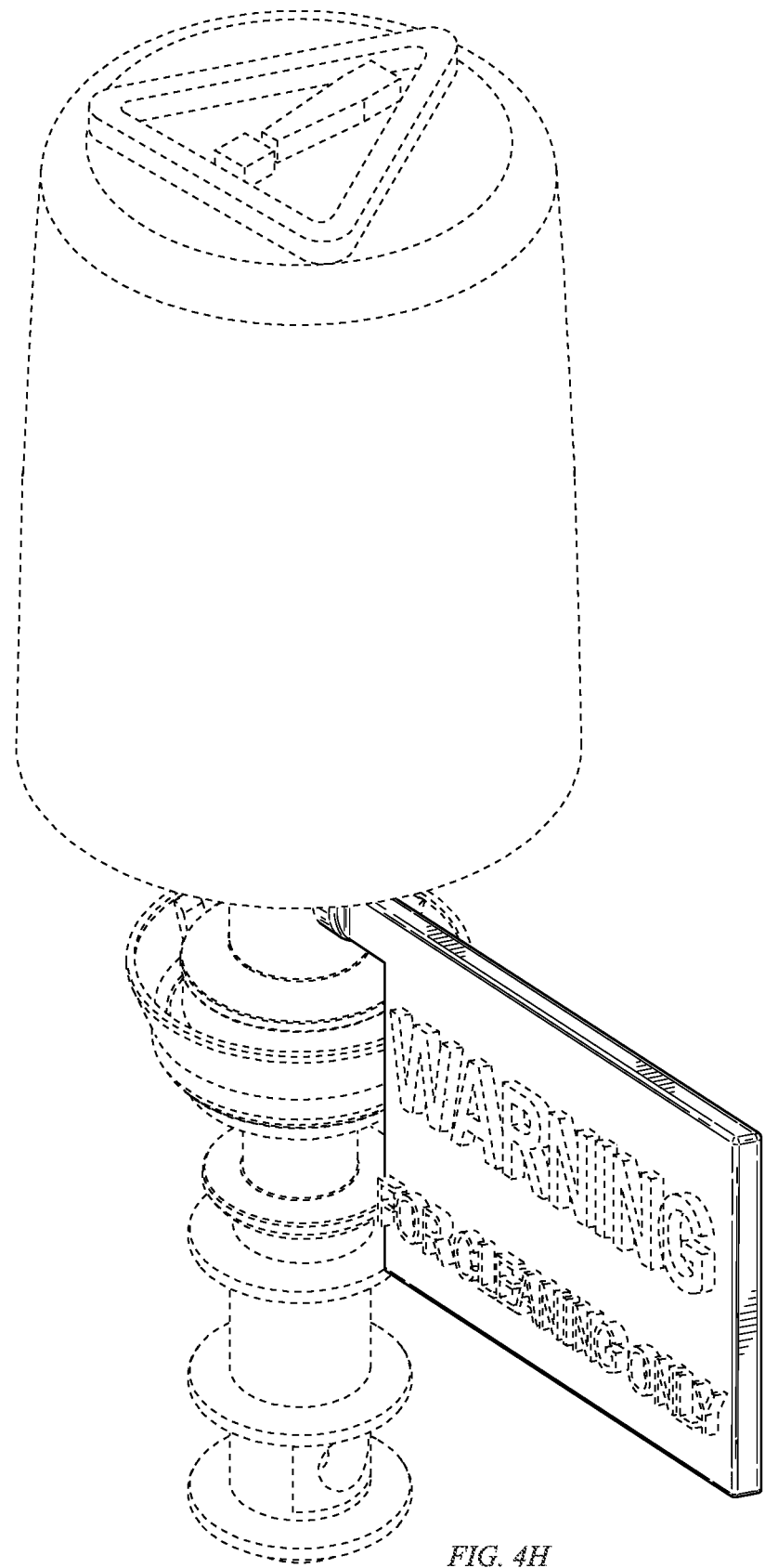

Referring specifically to FIGS. 4A and 4B, cleaning valve assembly 402 (or cleaning valve 402) may include an interface member 404 with a first indicator 408-1, a valve stem 406, and a second indicator 408-2. In various embodiments, cleaning valve assembly 402, or one or more components thereof, may be the same or similar to other cleaning valve assemblies, or one or more components thereof, described herein. For example, interface member 404 may be the same or similar to interface member 104 of FIG. 1A. As previously mentioned, the cleaning valve assembly 402 may include first indicator 408-1 and second indicator 408-2. The first indicator 408-1 may be the same as indicator 108 of FIG. 1A. The second indicator 408-2 may comprise a tag 410 with a plurality of raised surfaces (e.g., each letter can be considered a separate raised surface) and a clip 414. In many embodiments, the clip 414 is inserted through a radial hole, orifice, or aperture of the valve stem. In many such embodiments, the second indicator 408-2 may prevent insertion of the cleaning valve 402 into a valve well without removal of indicator 408-2. The clip 414 may include two arms that can deflect inwards to allow insertion through an orifice. Once the clip 414 is inserted through the orifice, the arms may deflect back outwards to retain the clip 414 in position (see e.g., FIG. 4B).

Figure 5A:
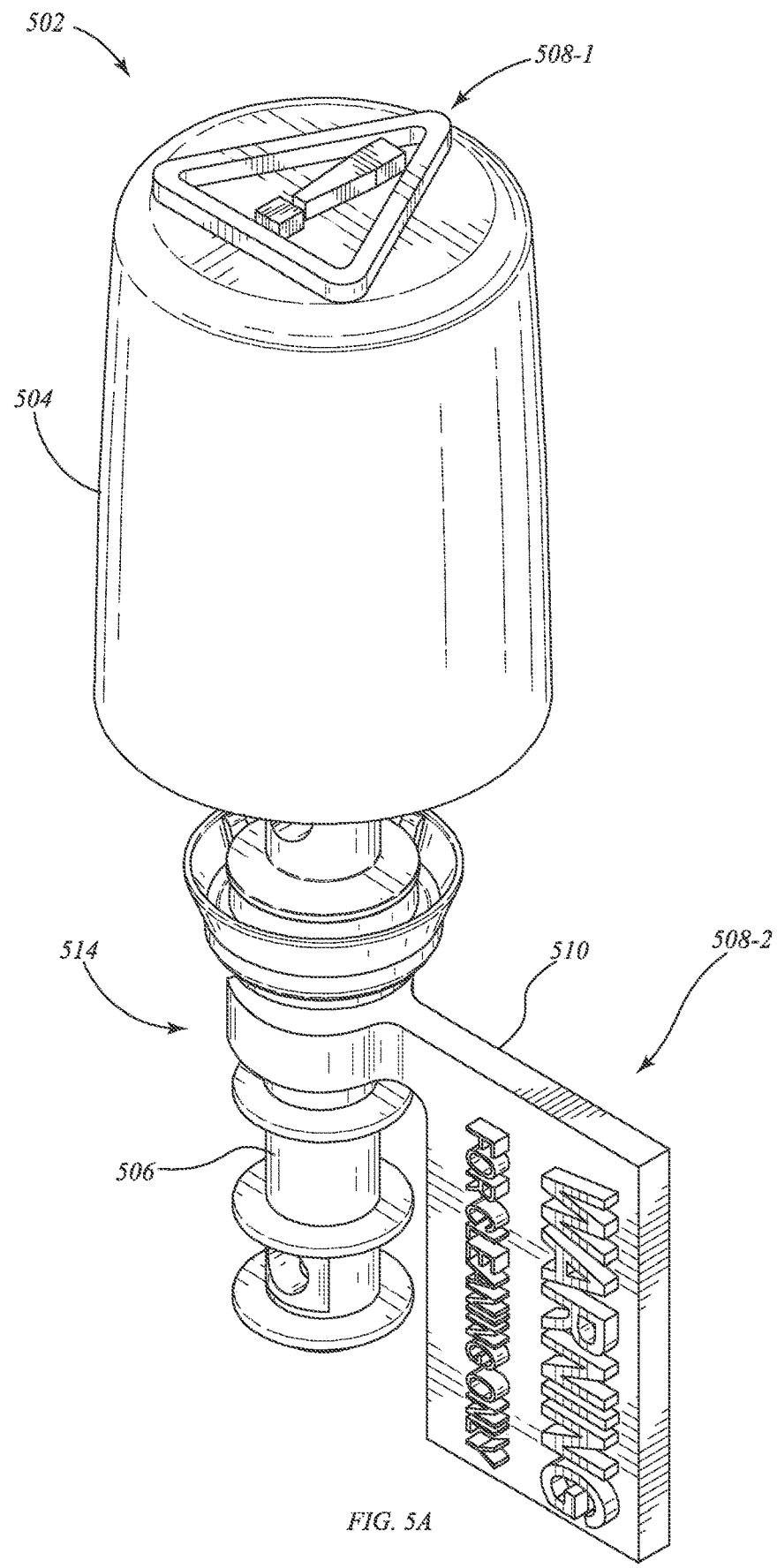
FIGS. 5A-5H illustrate a first perspective, left, front, back, right, top, bottom, and second perspective views, respectively, of an exemplary embodiment of a medical cleaning valve assembly according to the present disclosure described herein.
Figure 5B:
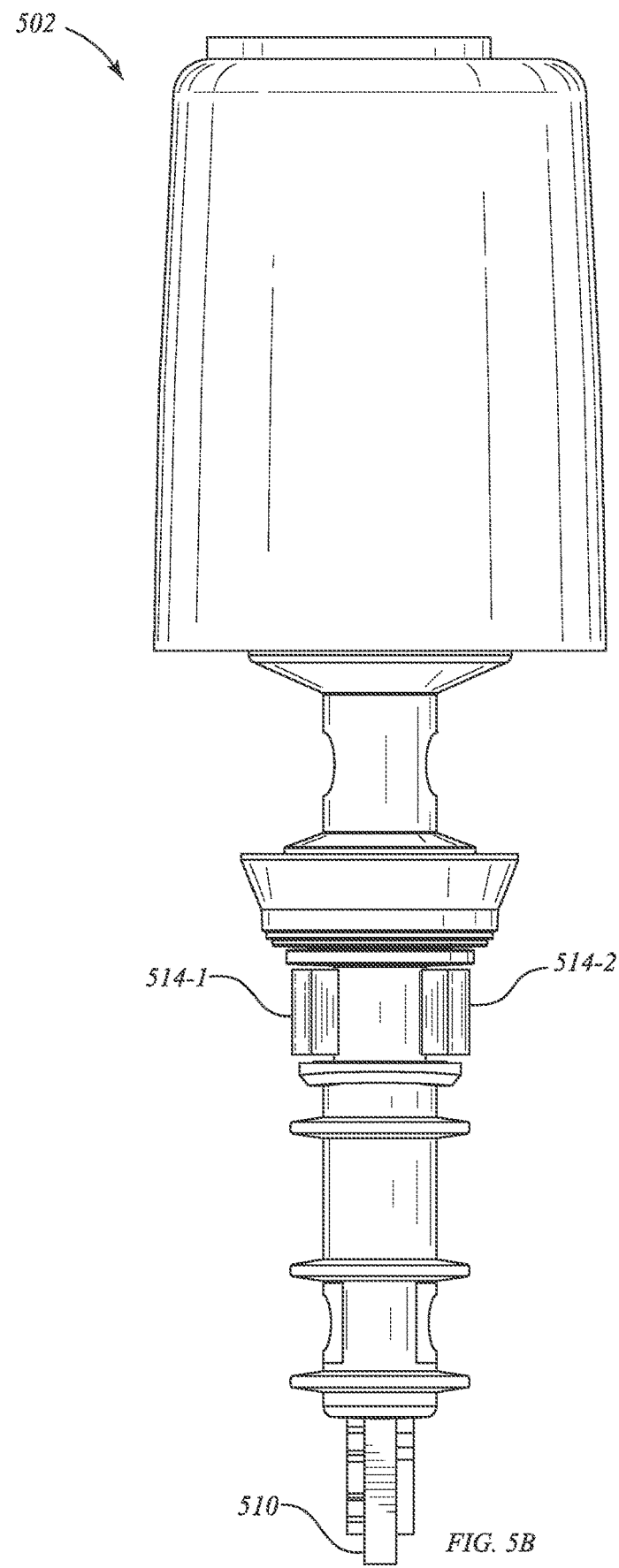
Figure 5C:
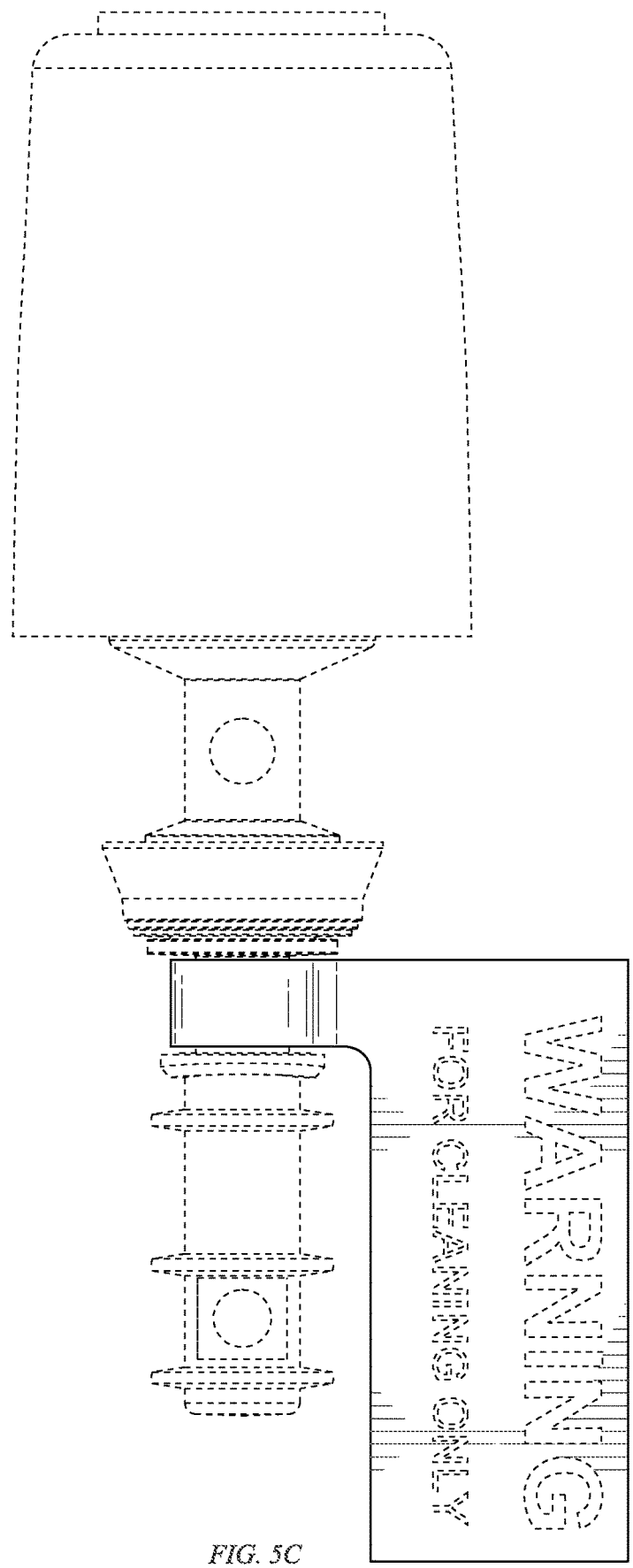
Figure 5D:
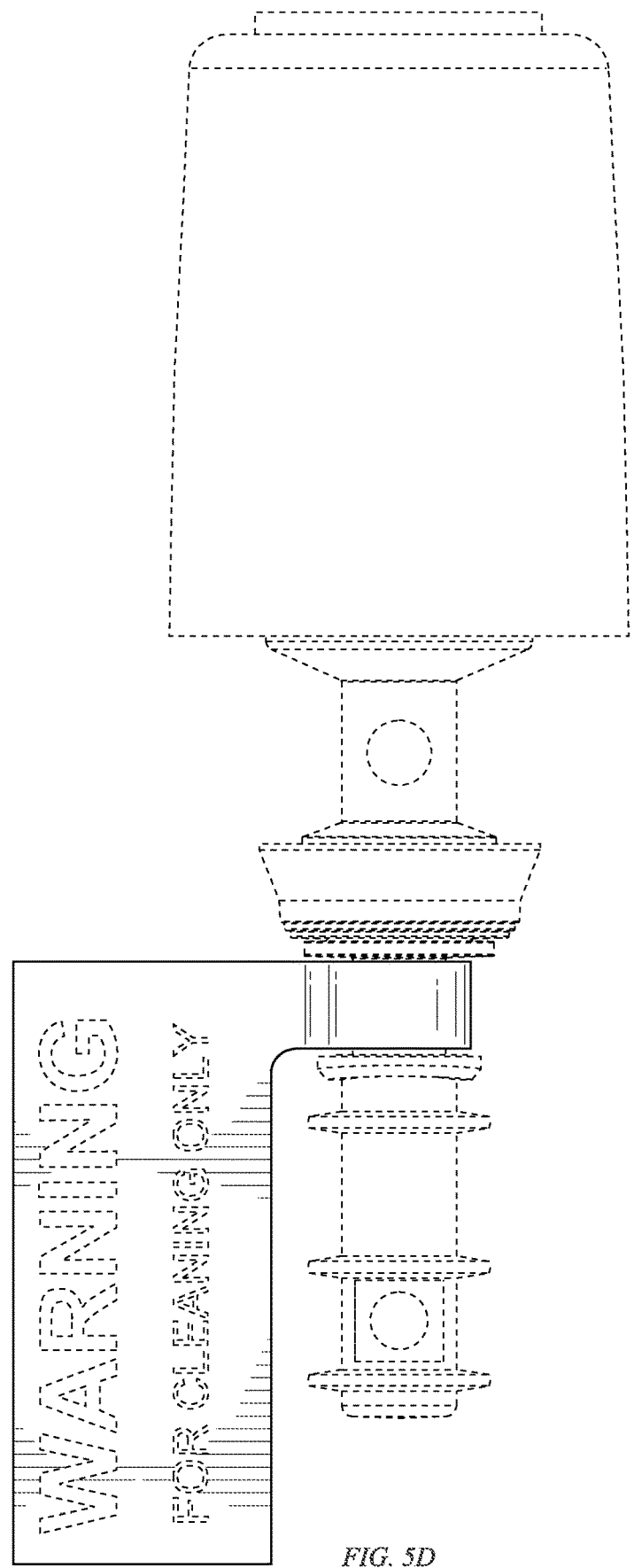
Figure 5E:
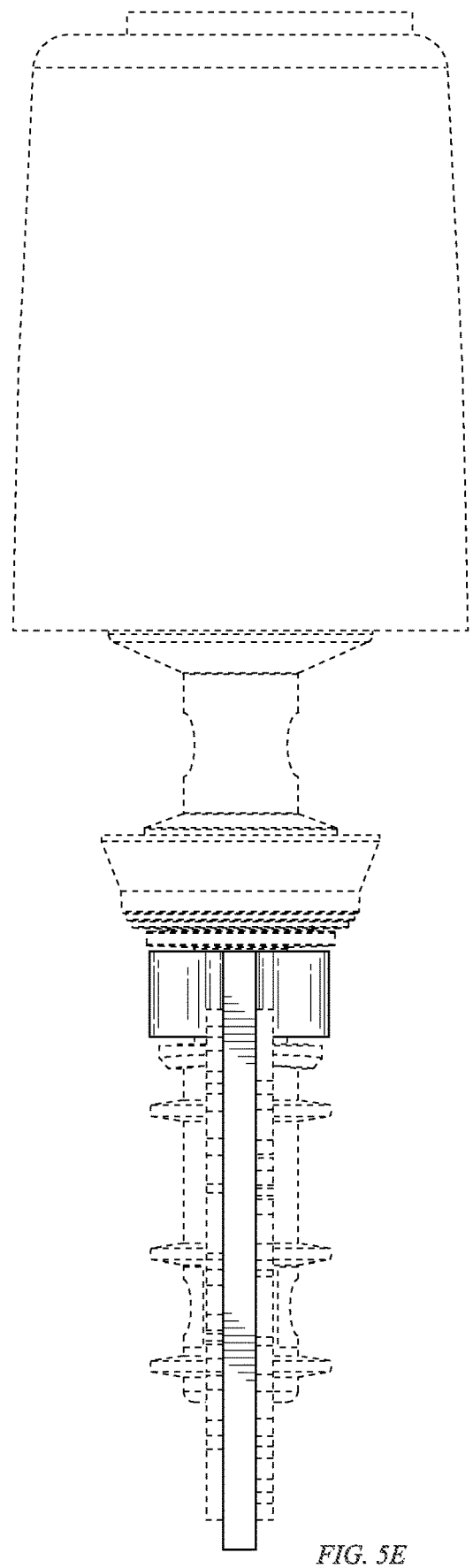
Figure 5F:
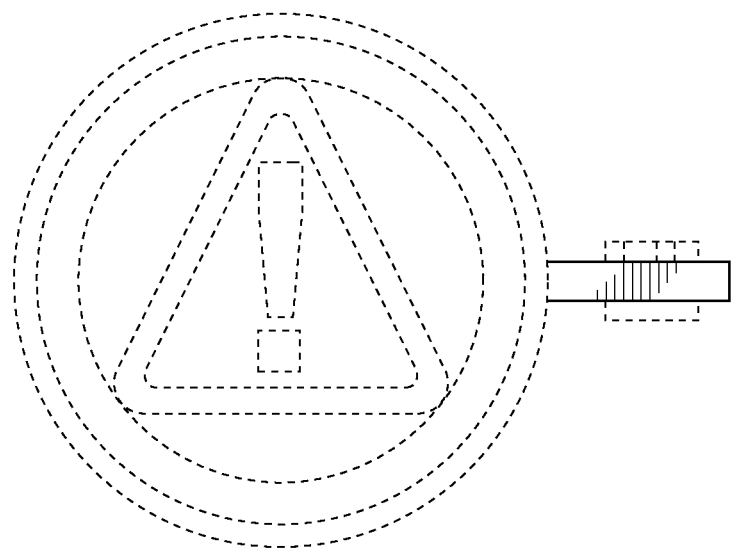
Figure 5G:
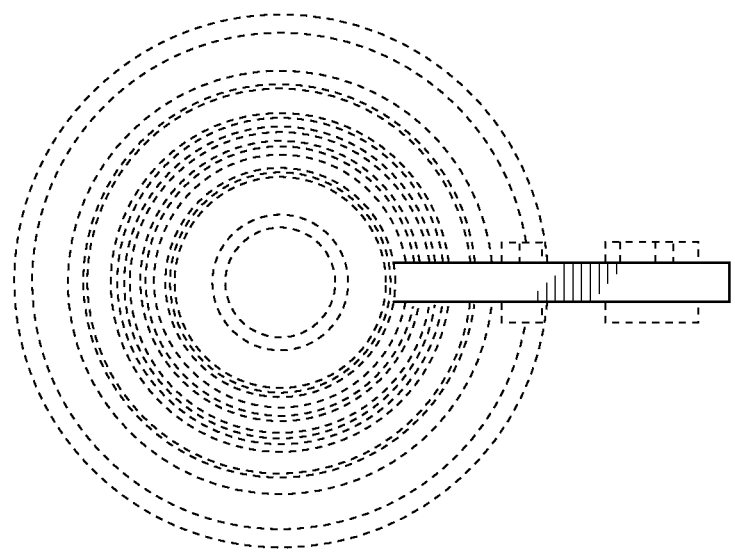
Figure 5H:
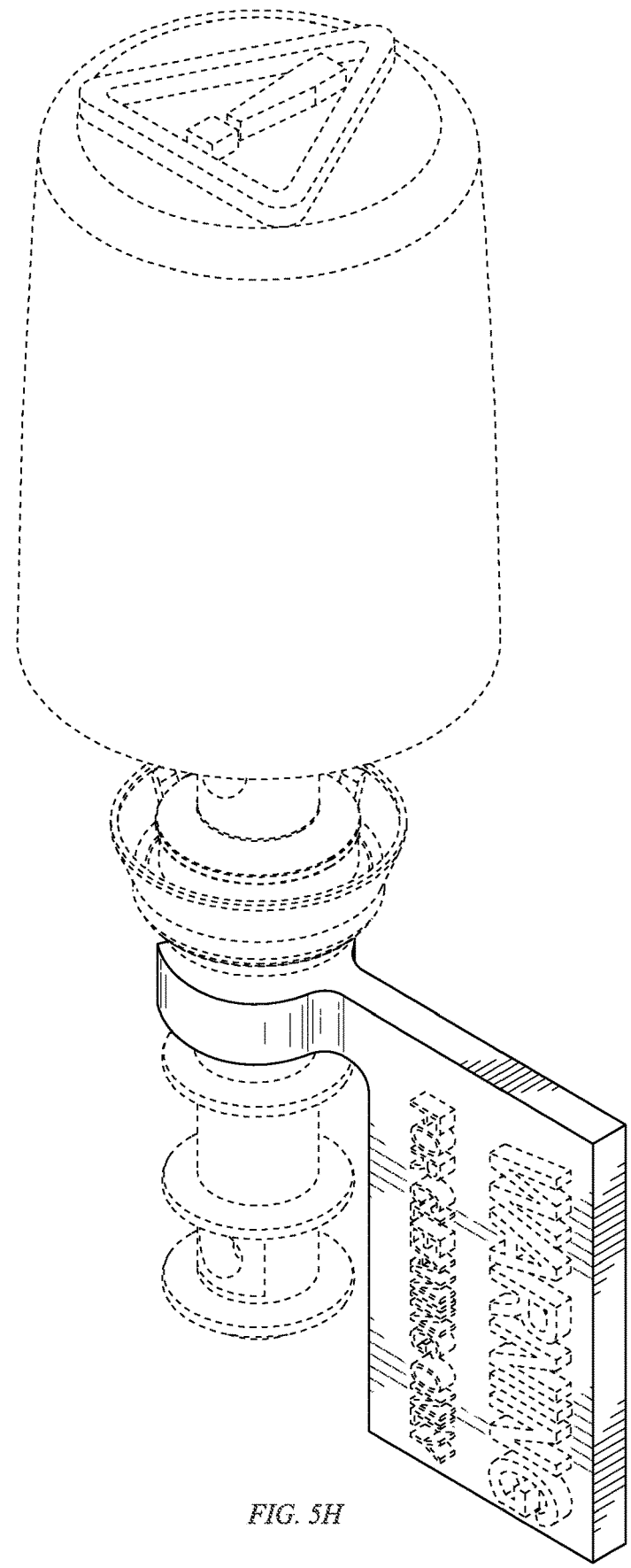

Referring specifically to FIGS. 5A and 5B, cleaning valve assembly 502 (or cleaning valve 502) may include an interface member 504 with a first indicator 508-1, a valve stem 506, and a second indicator 508-2. In various embodiments, cleaning valve assembly 502, or one or more components thereof, may be the same or similar to other cleaning valve assemblies, or one or more components thereof, described herein. For example, cleaning valve assembly 502 may be the same or similar to valve 100 of FIG. 11. As previously mentioned, the cleaning valve assembly 502 may include first indicator 508-1 and second indicator 508-2. The first indicator 508-1 may be the same as indicator 108 of FIG. 1A. The second indicator 508-2 may comprise a tag 510 with a plurality of raised surfaces (e.g., each letter can be considered a separate raised surface) and a clip 514. In many embodiments, the clip 514 couples around a portion of the valve stem 514. In many such embodiments, the second indicator 508-2 may prevent insertion of the cleaning valve 502 into a valve well without removal of indicator 508-2. The clip 514 may include two arms that can deflect outwards to allow coupling around a portion of the valve stem 514. Once the clip 514 is coupled around the valve stem 514, the arms may deflect back inwards to retain the clip 514 coupled to the valve stem 514 (see e.g., 514-1, 514-2 of FIG. 5B).

Figure 6A:
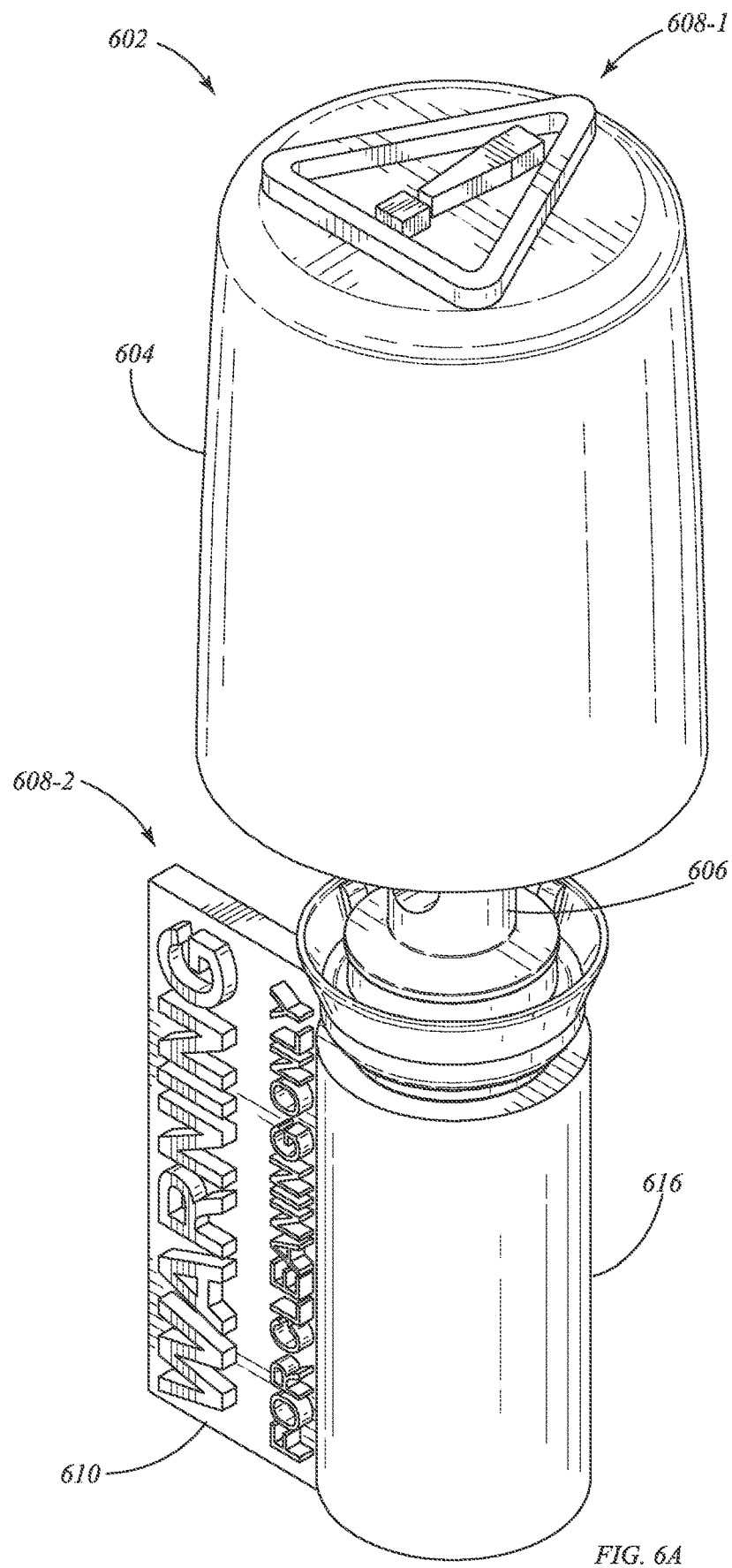
FIGS. 6A-6H illustrate first perspective, front, back, right, left, top, bottom, and second perspective views, respectively, of an exemplary embodiment of a medical cleaning valve assembly according to the present disclosure described herein.
Figure 6B:
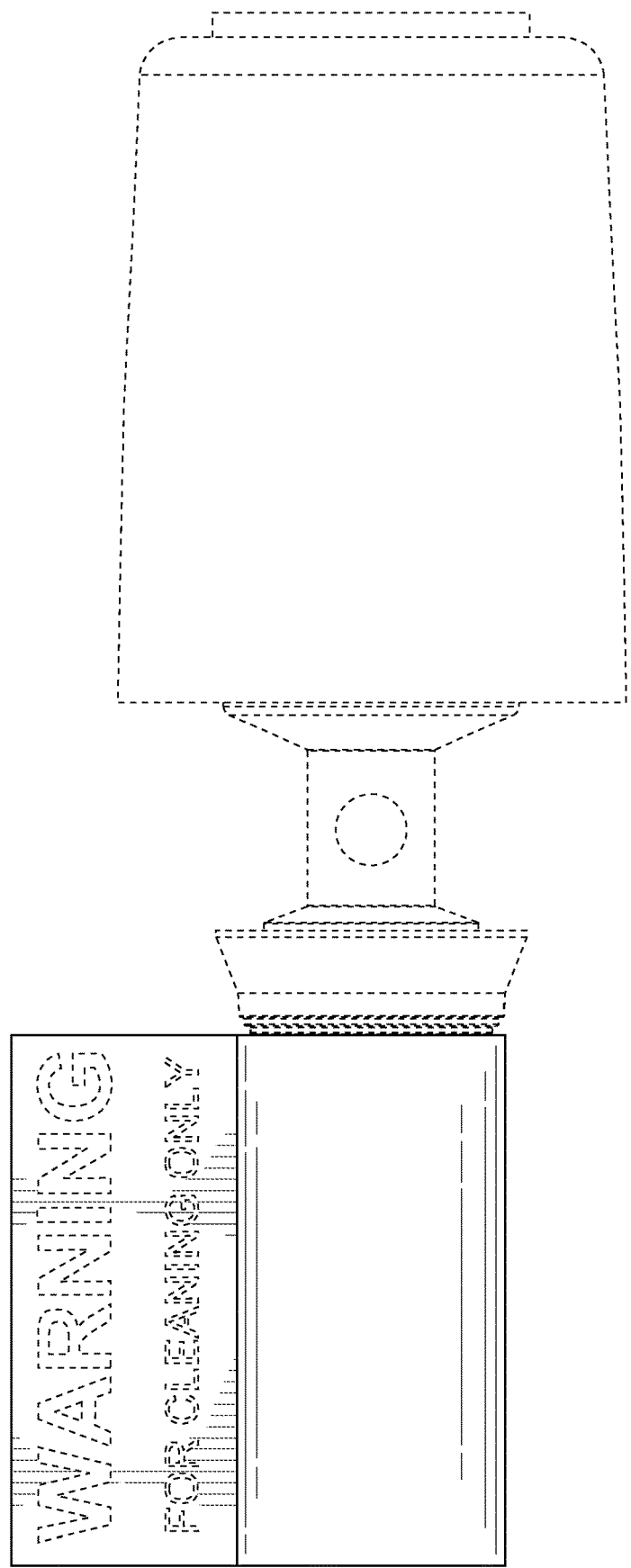
Figure 6C:
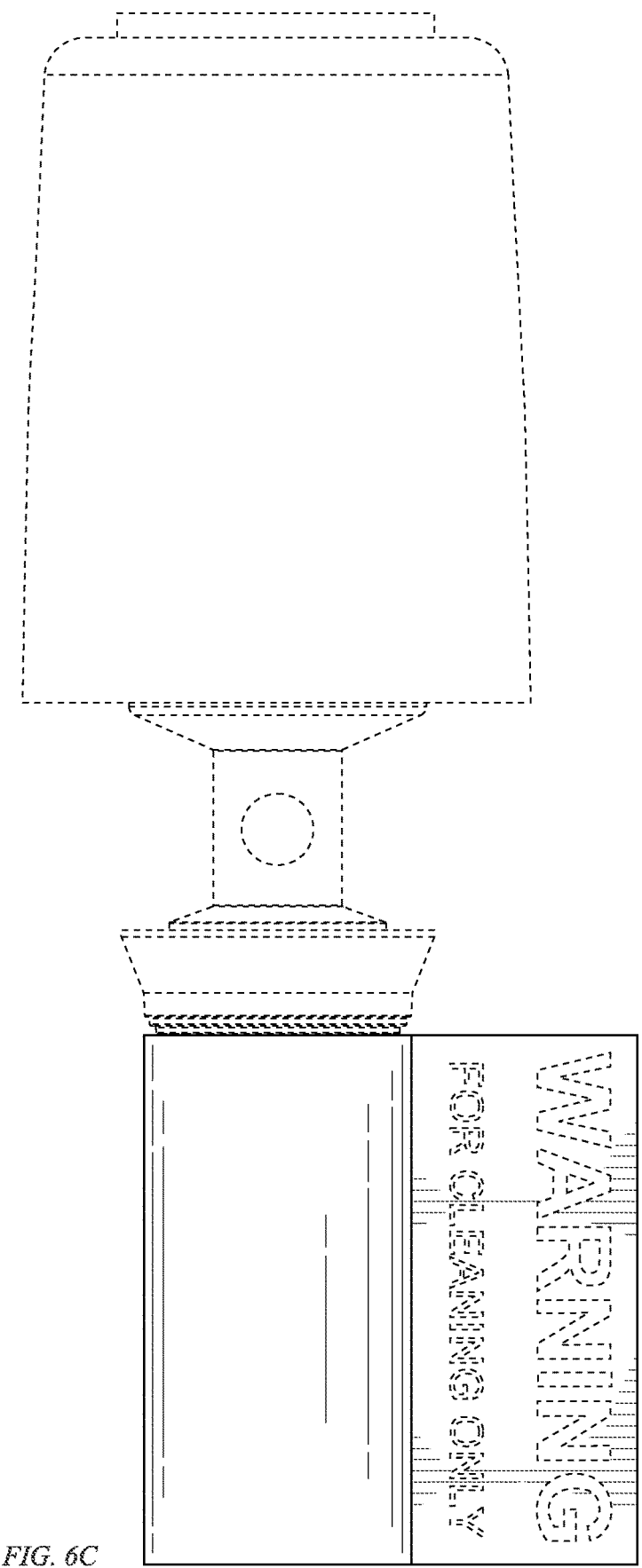
Figure 6D:
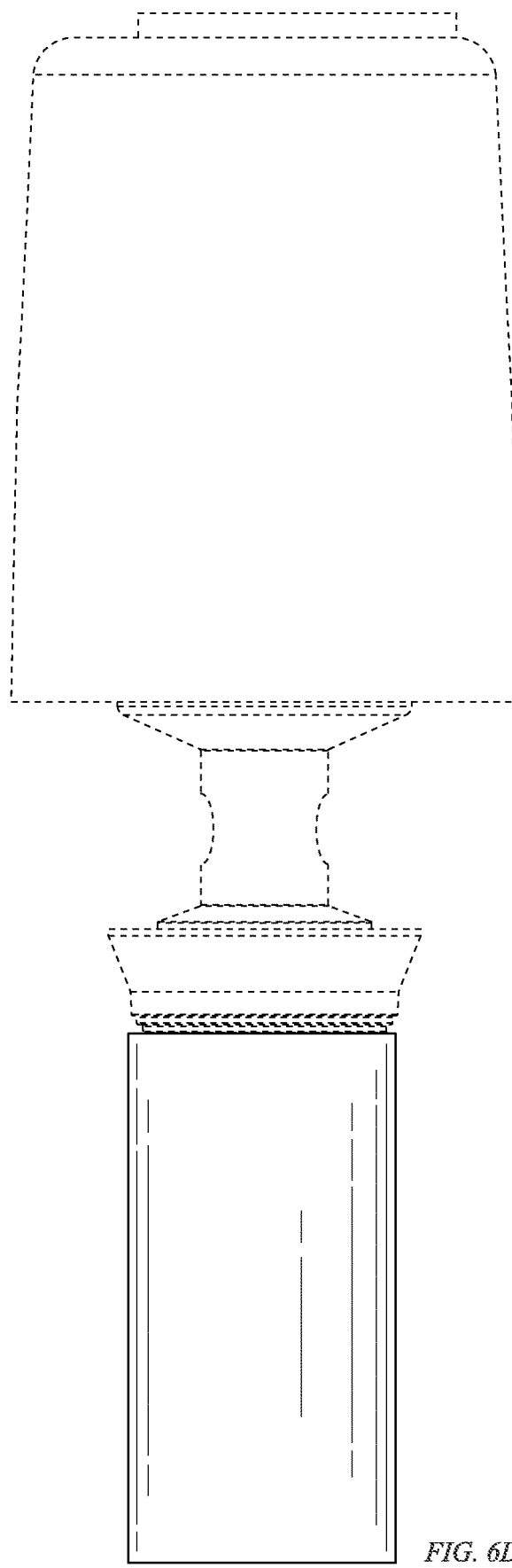
Figure 6E:
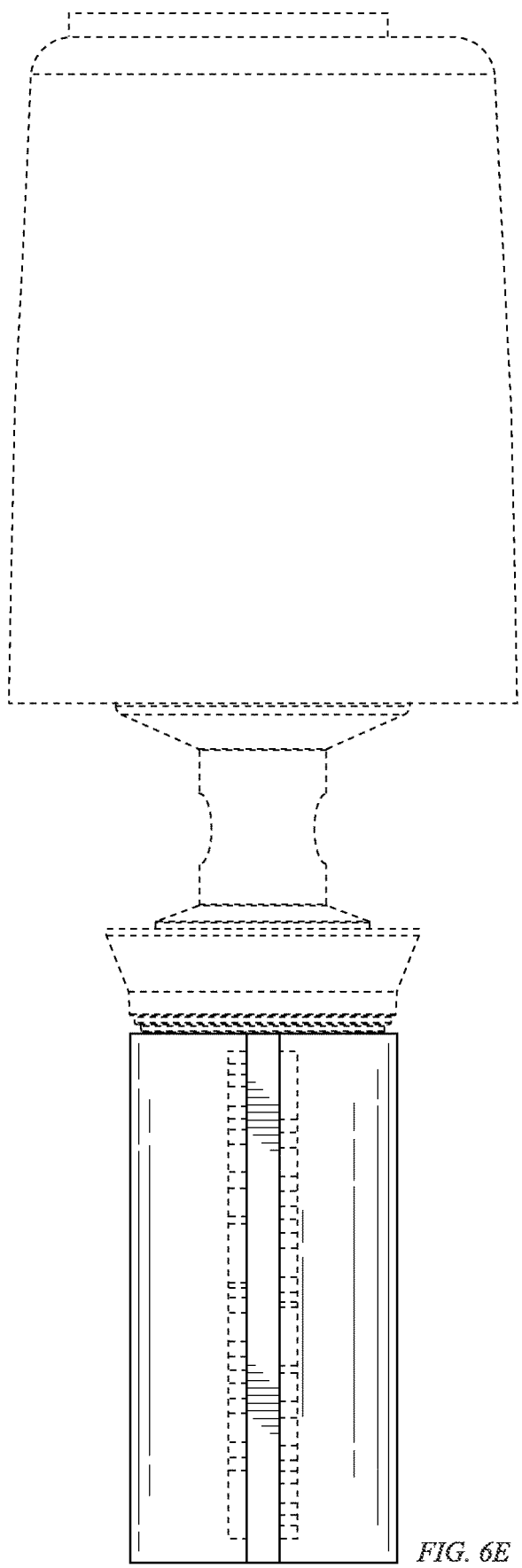
Figure 6F:
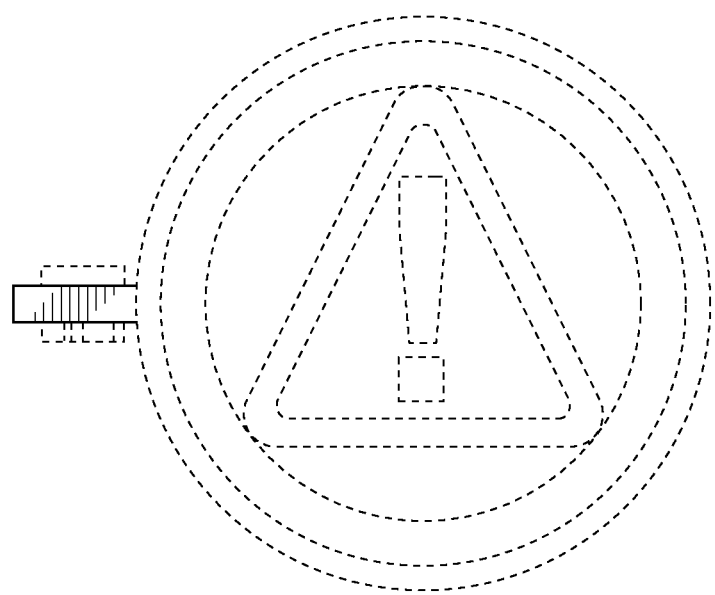
Figure 6G:
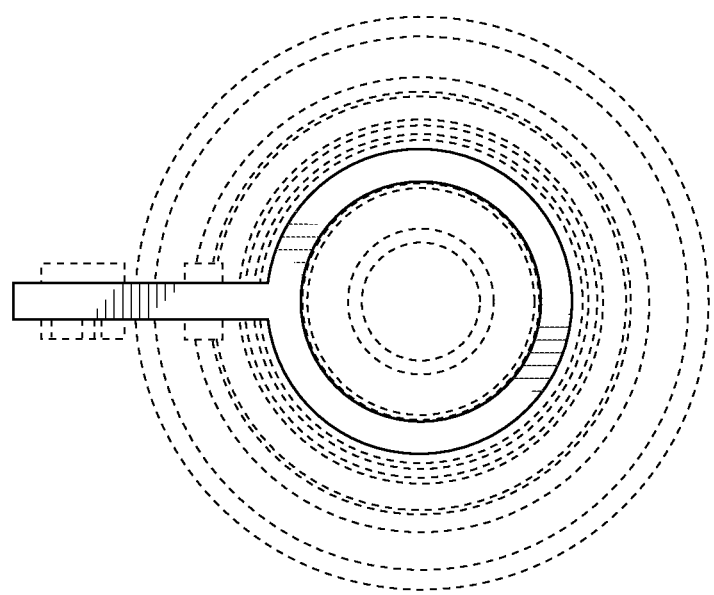
Figure 6H:
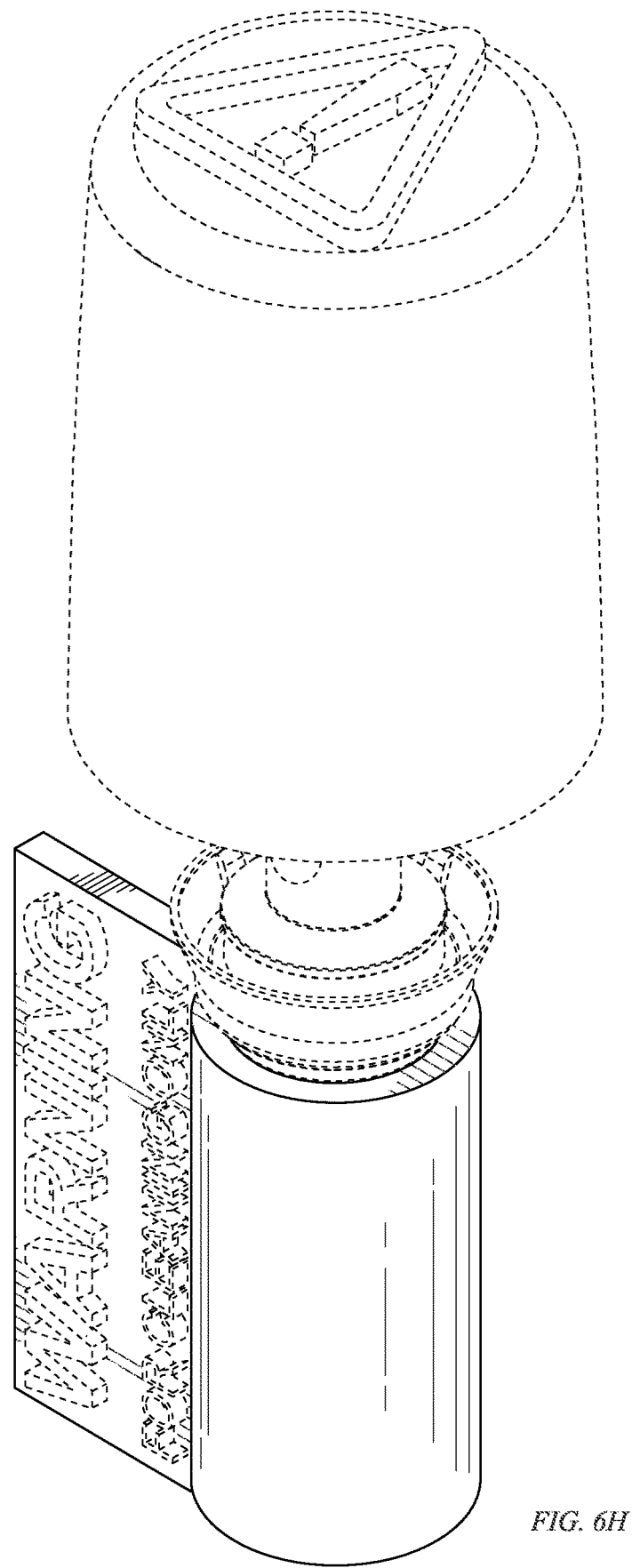

Referring specifically to FIG. 6A, cleaning valve assembly 602 (or cleaning valve 602) may include an interface member 604 with a first indicator 608-1, a valve stem 606, and a second indicator 608-2. In various embodiments, cleaning valve assembly 602, or one or more components thereof, may be the same or similar to other cleaning valve assemblies, or one or more components thereof, described herein. For example, valve stem 606 may be the same or similar to valve stem 1506 of FIG. 15. As previously mentioned, the cleaning valve assembly 602 may include first indicator 608-1 and second indicator 608-2. The first indicator 608-1 may be the same as indicator 108 of FIG. 1A. The second indicator 608-2 may comprise a barrel 616 and a tag 610 with a plurality of raised surfaces (e.g., each letter can be considered a separate raised surface).

In many embodiments, the barrel 616 may slide over a portion of the valve stem 606. In many such embodiments, the second indicator 608-2 may prevent insertion of the cleaning valve 602 into a valve well without removal of indicator 608-2. The barrel 616 may have an inside diameter that is approximately the same as the largest outside diameter of a distal portion of the valve stem 606. In some embodiments, there may be a slight interference fit between the barrel 616 and the valve stem 606. For example, the slight interference fit may prevent the barrel 616 from sliding off the valve stem 606 in the absence of an external force. In various embodiments, the tag 610 may be integrally formed with the barrel 616. In the illustrated embodiment, the tag 610 radially extends from the barrel 616 along the entire length of the barrel 616. In some embodiments, an indicator and/or tag may extend horizontally, proximally, distally, or any angle in between, from any portion of the barrel 616. For example, tag 610 may extend distally from the distal end of barrel 616.

Figure 7A:
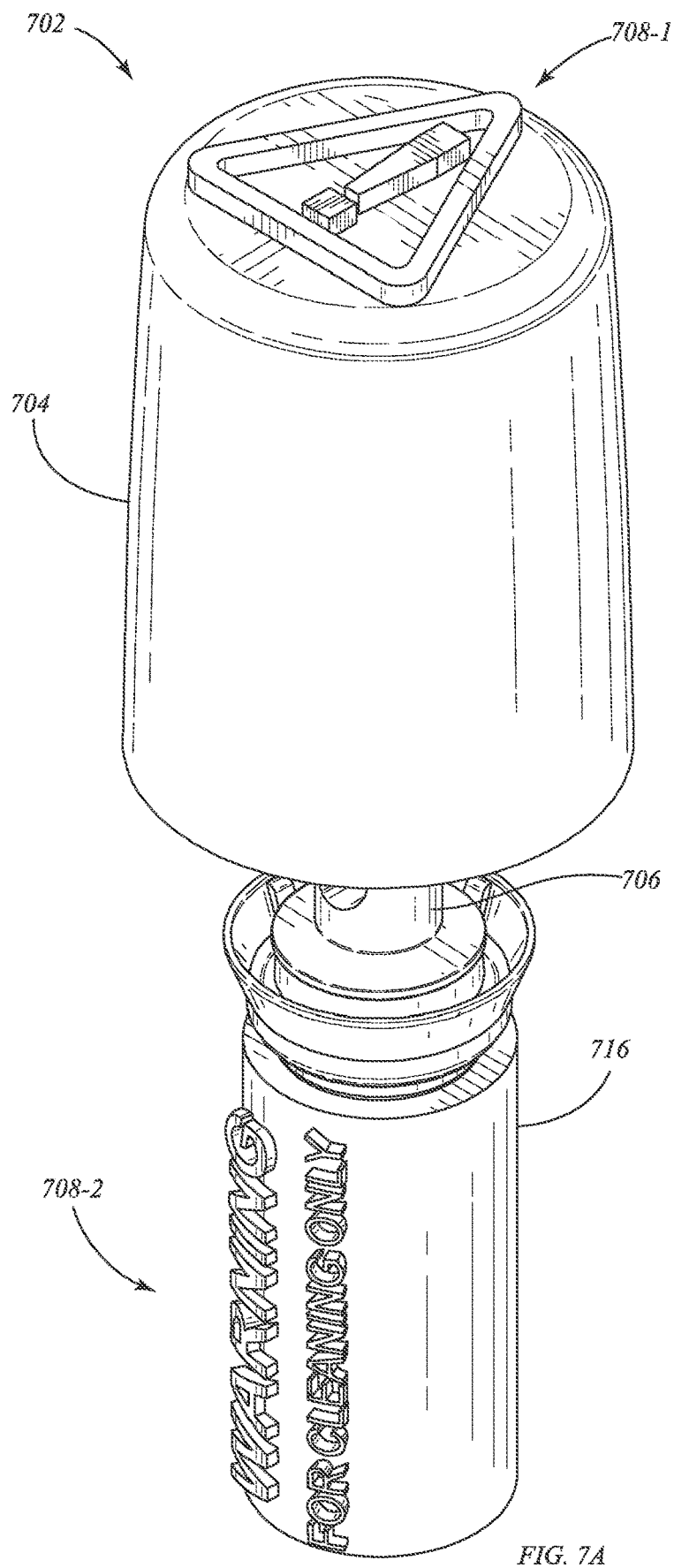
FIGS. 7A-7H illustrate first perspective, front, back, right, left, top, bottom, and second perspective views, respectively, of an exemplary embodiment of a medical cleaning valve assembly according to the present disclosure described herein.
Figure 7B:
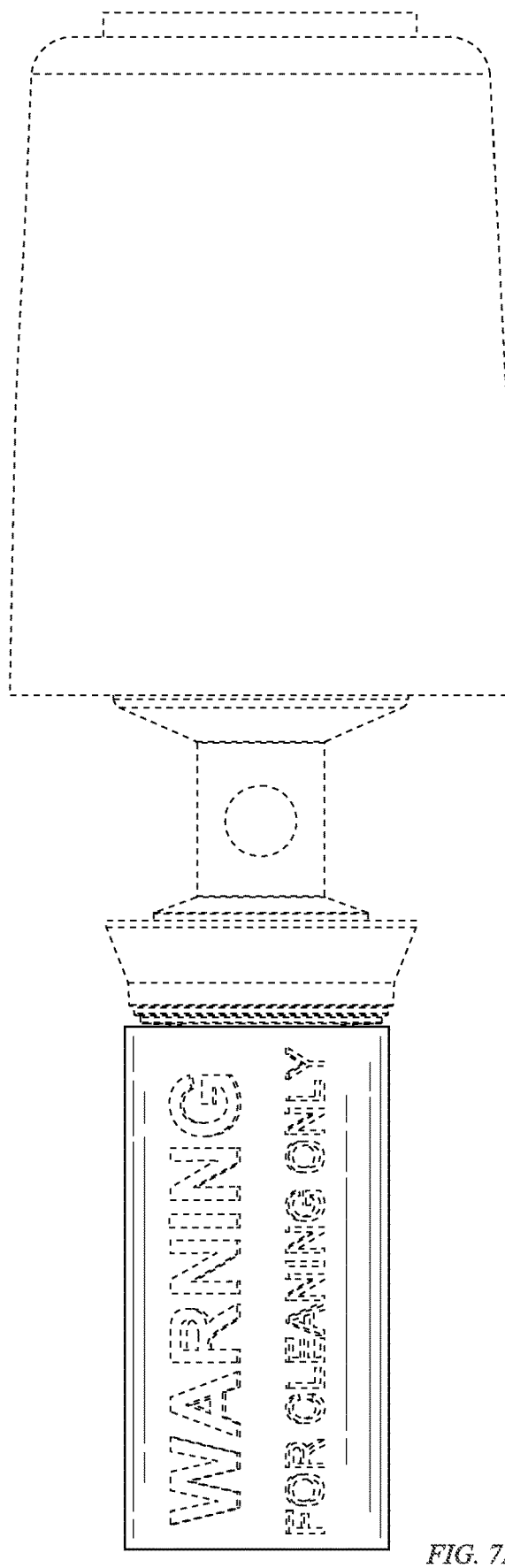
Figure 7C:
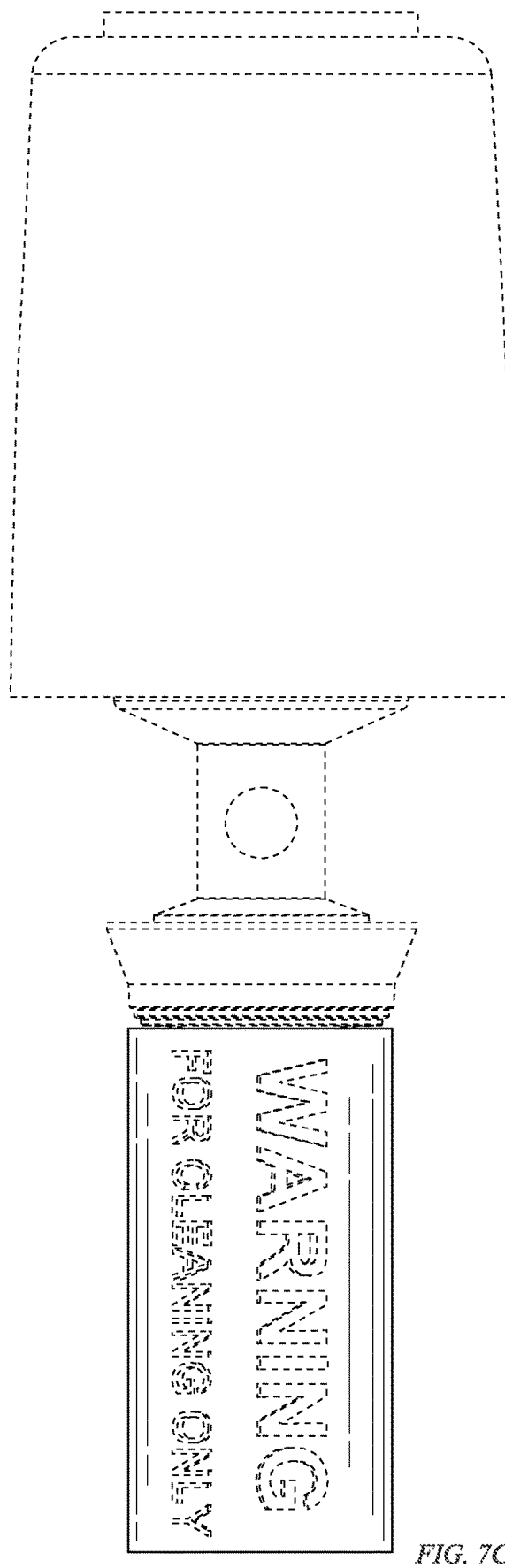
Figure 7D:
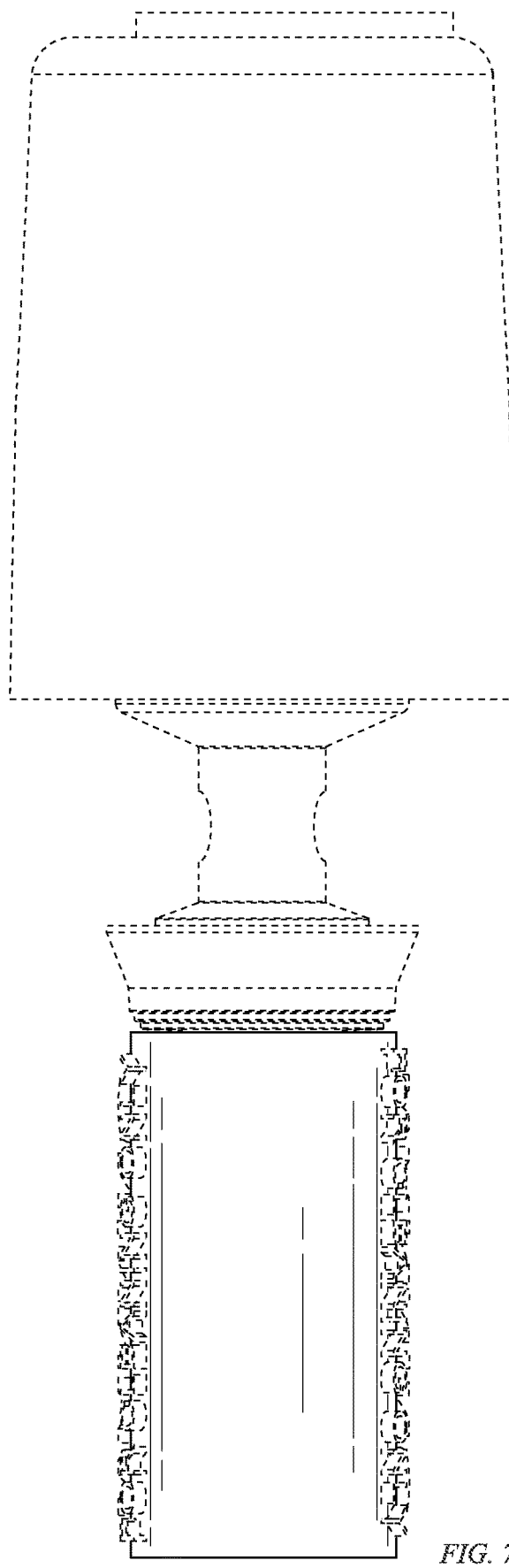
Figure 7E:
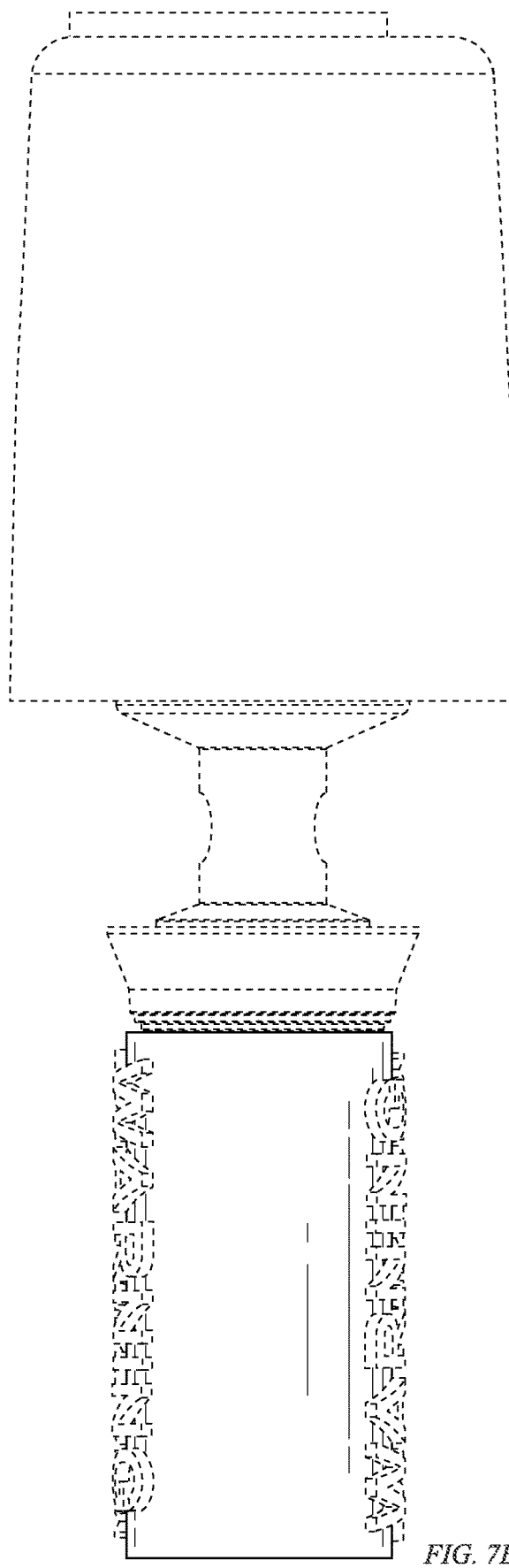
Figure 7F:
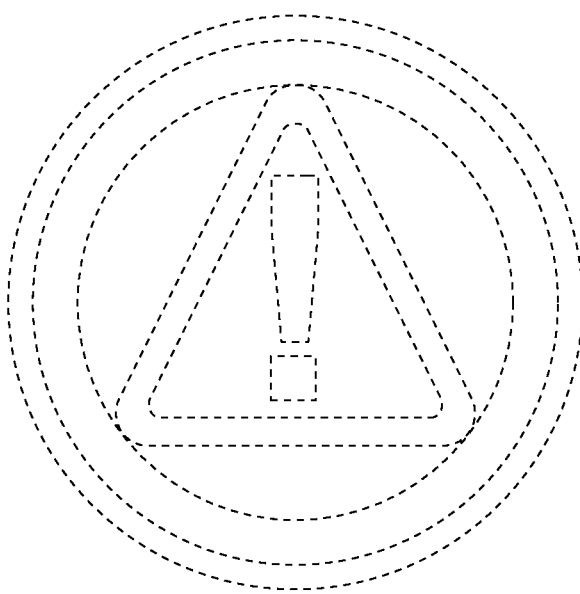
Figure 7G:
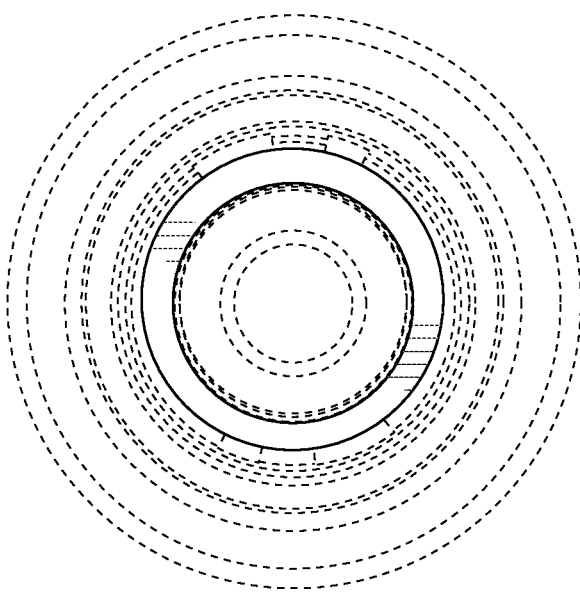
Figure 7H:
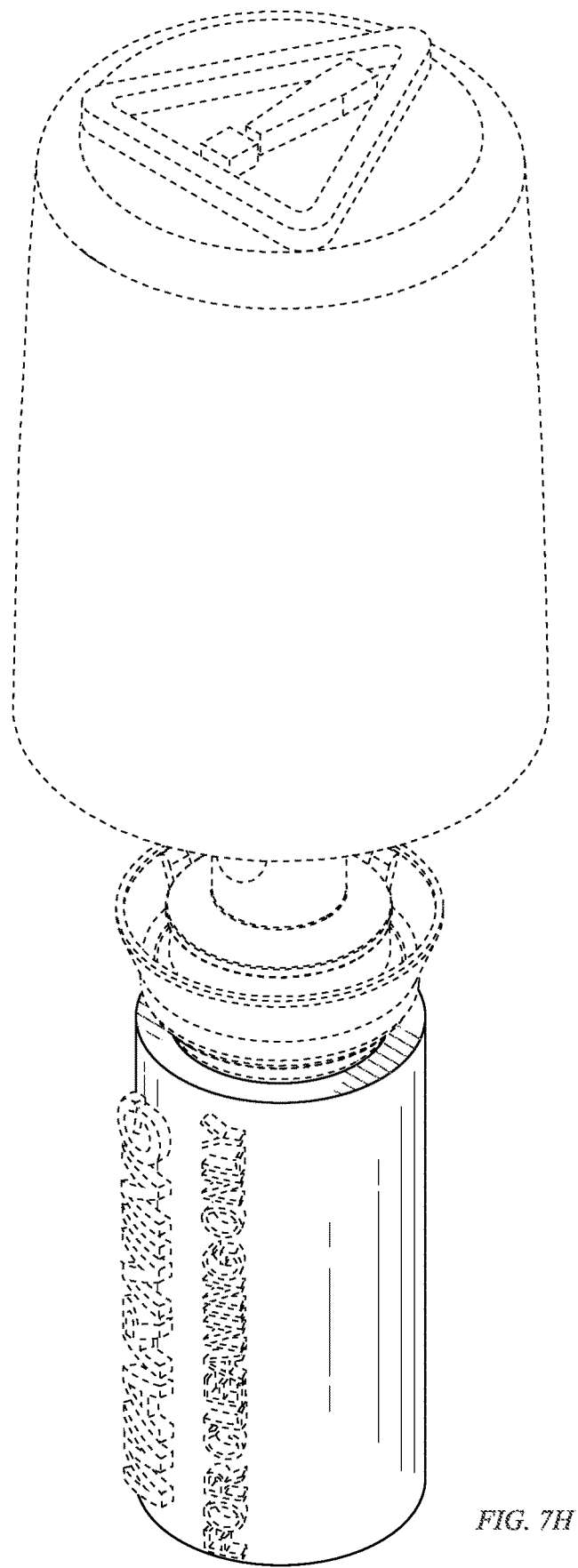

Referring specifically to FIG. 7A, cleaning valve assembly 702 (or cleaning valve 702) may include an interface member 704 with a first indicator 708-1, a valve stem 706, and a second indicator 708-2. In various embodiments, cleaning valve assembly 702, or one or more components thereof, may be the same or similar to other cleaning valve assemblies, or one or more components thereof, described herein. For example, cleaning valve assembly 702 may be the same or similar to cleaning valve assembly 1502 of FIG. 15. As previously mentioned, the cleaning valve assembly 702 may include first indicator 708-1 and second indicator 708-2. The first indicator 708-1 may be the same as indicator 108 of FIG. 1A. The second indicator 708-2 may comprise a barrel 716 with a plurality of raised surfaces (e.g., each letter can be considered a separate raised surface). In many embodiments, the barrel 716 may slide over a portion of the valve stem 706. In many such embodiments, the second indicator 708-2 may prevent insertion of the cleaning valve 702 into a valve well without removal of indicator 708-2. The barrel 716 may have an inside diameter that is approximately the same as the largest outside diameter of a distal portion of the valve stem 706. In some embodiments, there may be a slight interference fit between the barrel 716 and the valve stem 706. For example, the slight interference fit may prevent the barrel 716 from sliding off the valve stem 706 in the absence of an external force.

FIGS. 8-14 illustrate exemplary medical cleaning valves, assemblies, and systems accordingly to the present disclosure described herein. In many embodiments, one or more components of the medical cleaning valve assemblies of FIGS. 1A-7H may be the same or similar in construction, function, and/or appearance as described with respect to FIGS. 8-14. One or more of the features for differentiating procedural valves, described above, may be incorporated into the designs of FIGS. 8-14. Embodiments are not limited in this context.

Figure 8:
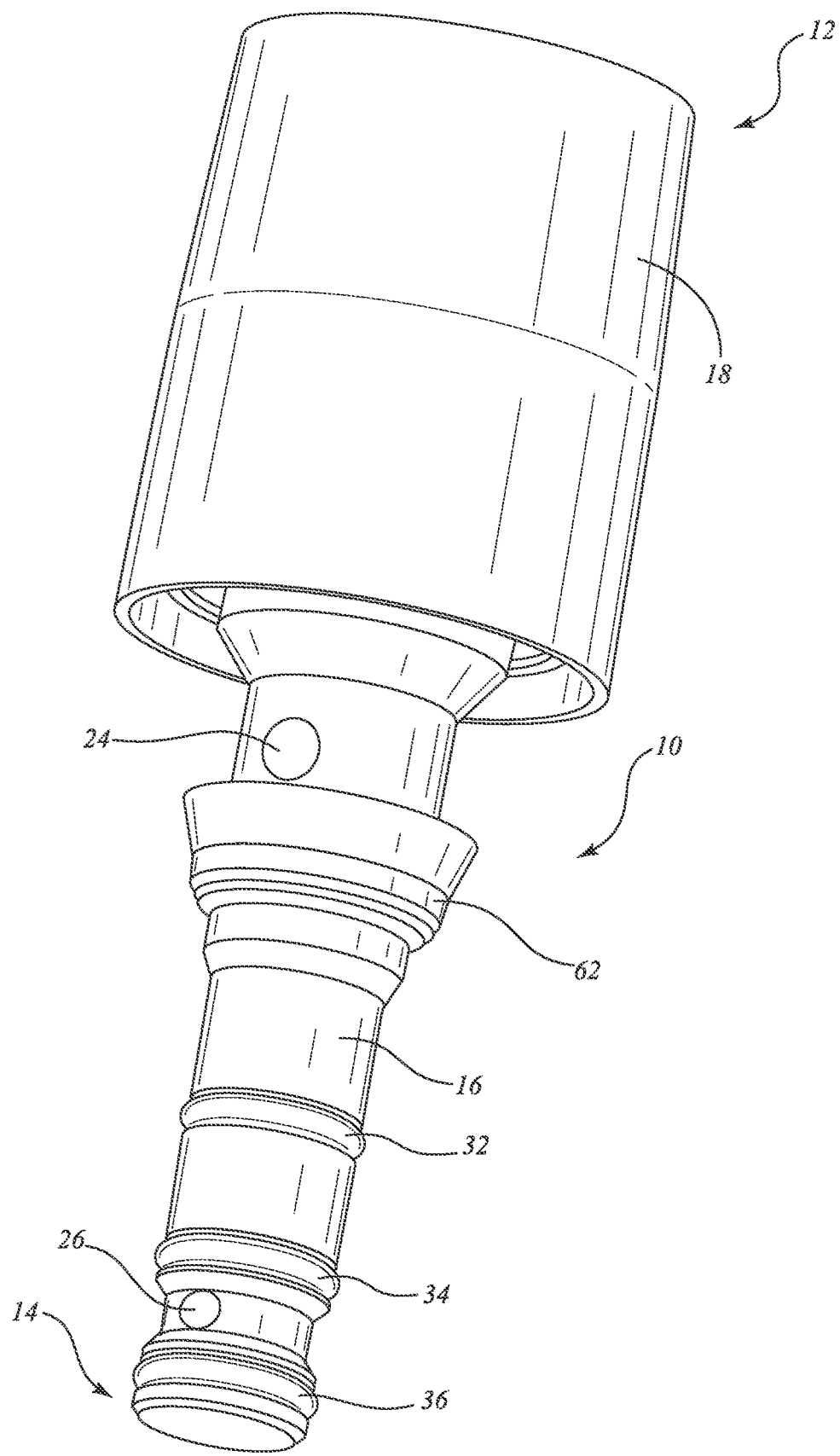
FIG. 8 illustrates a perspective view of a first exemplary valve according to the present disclosure described herein.
Figure 9:
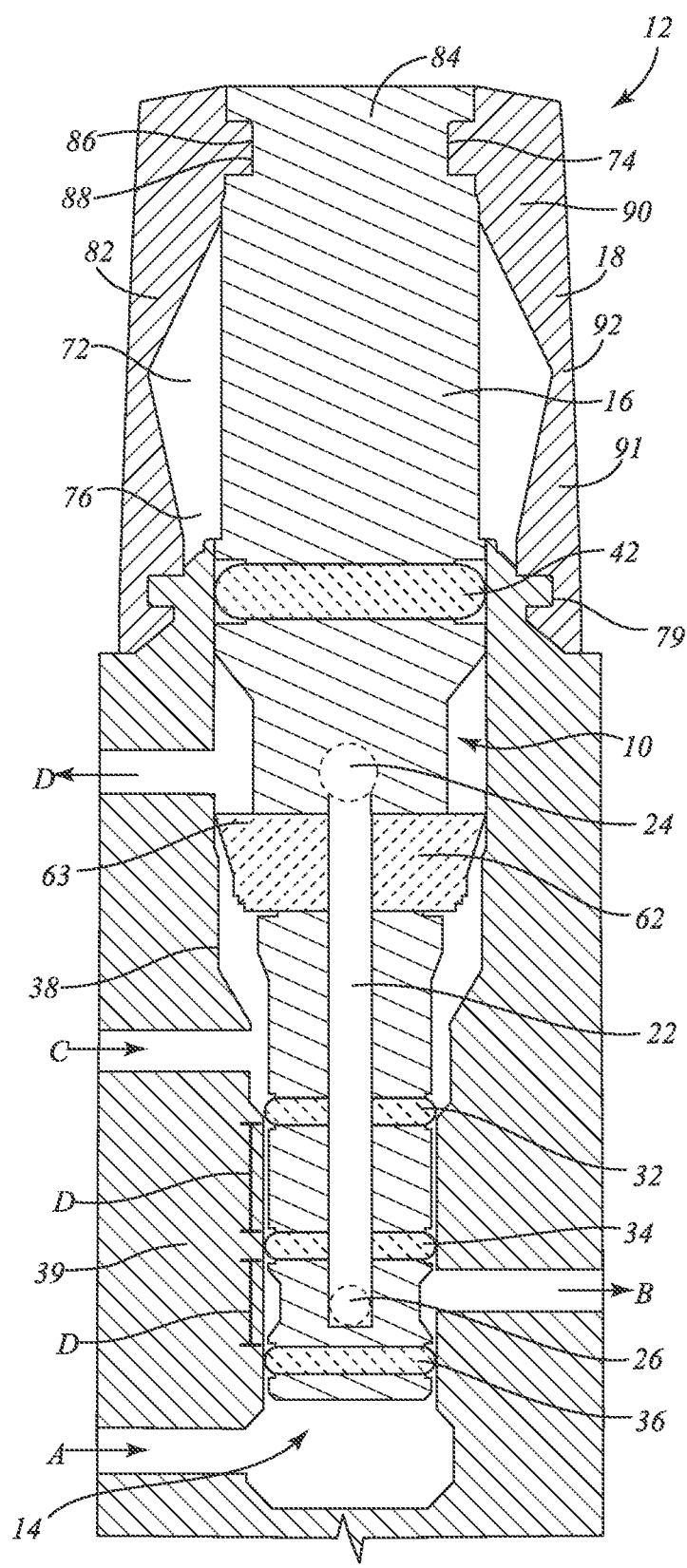
FIGS. 9 and 10 illustrate cross-sectional views of the first exemplary valve of FIG. 8 according to the present disclosure described herein.
Figure 10:
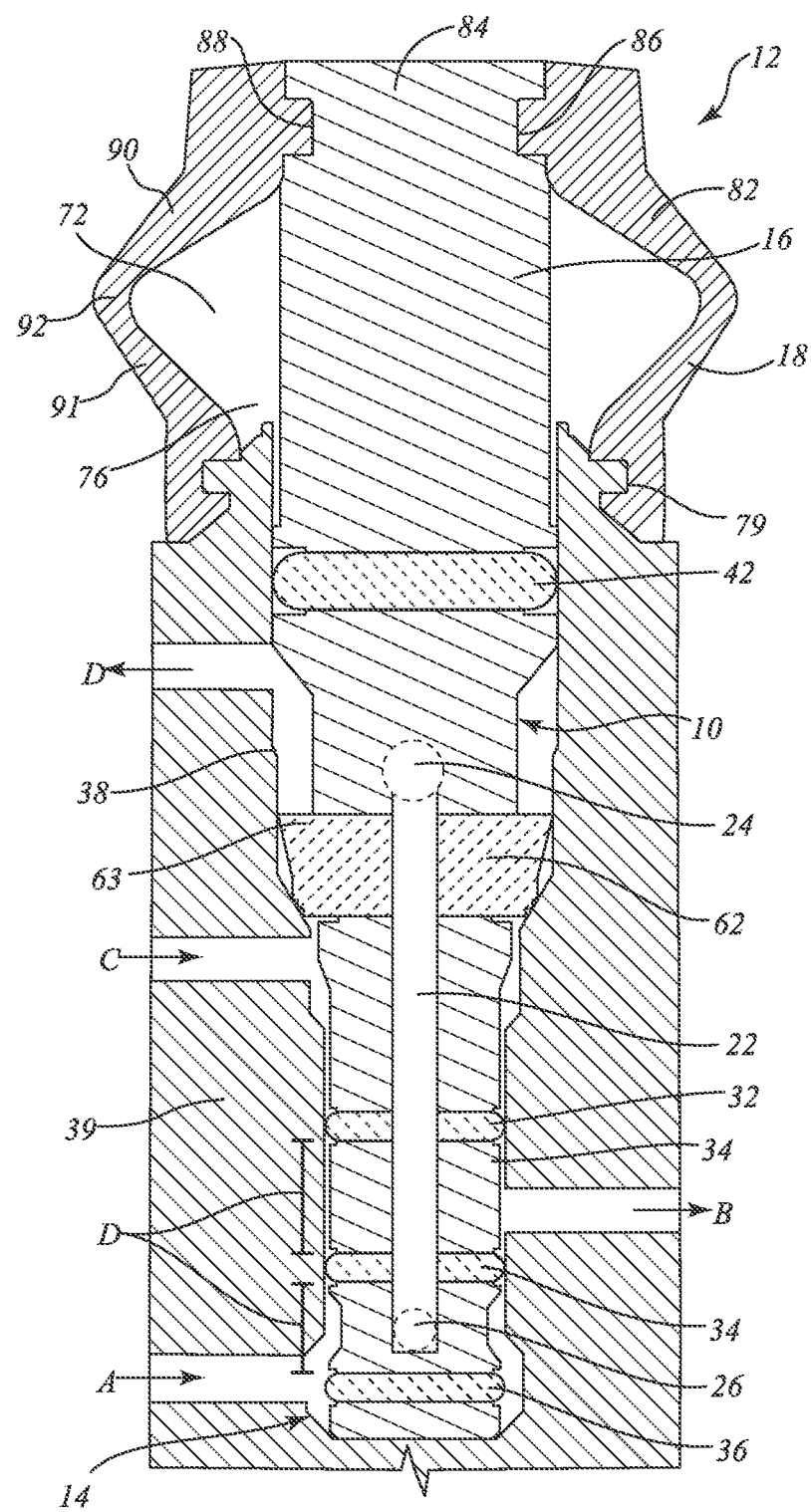

FIG. 8 illustrates a perspective view of an exemplary cleaning valve 10 (or cleaning valve assembly 10). FIG. 9 illustrates a cross-sectional view of valve 10 in a first configuration, and FIG. 10 illustrates a cross-sectional view the valve 10 in a second configuration. FIGS. 9 and 10 show valve 10 inserted into an endoscope valve cylinder (i.e., valve well) in a handle of an endoscope. Valve 10 may have a proximal end 12 and a distal end 14. An inner cylindrical member 16 may extend from proximal end 12 to distal end 14. An outer cylindrical member 18 may be disposed around inner cylindrical member 16 at proximal end 12. In the illustrated embodiment, one or more portions of the outer cylindrical member 18 and the inner cylindrical member 16 may form an interface member. For example, the proximal end 12 of the inner cylindrical member 16 may comprise a first portion of the interface member and the outer cylindrical member 18 may comprise a second portion of the interface member. Further, in some embodiments, the distal end of the inner cylindrical member 16 may include one or more indicators. In many embodiments, the inner cylindrical member 16 may comprise and/or be referred to as a valve stem.

Inner cylindrical member 16 may be, for example, a valve stem. Inner cylindrical member 16 may be a single, unitary structure formed of a single, continuous piece of material and may be made from a metal (e.g., stainless steel, titanium, aluminum, alloys, or the like), from a polymer (e.g. polycarbonate, acrylonitrile butadiene styrene (ABS), high-density polyethylene (HDPE), Nylon, polyether ether ketone (PEEK), thermoplastic, plastic, or the like), or from any other suitable material. Depending on the material used, inner cylindrical member 16 may be machined, injection molded, extruded (via, e.g., 3D printing), or otherwise formed. Inner cylindrical member 16 may be formed of a clear thermoplastic so that certain portions of an interior of inner cylindrical member 16 are visible through external walls of inner cylindrical member.

Inner cylindrical member 16 may have a first lumen 22 (see, e.g., FIGS. 9 and 10) extending at least partway through inner cylindrical member 16 along a central longitudinal axis. Alternatively, first lumen 22 may extend through another longitudinal axis of inner cylindrical member 16 (e.g., first lumen 22 may be off-centered). A space between an exterior surface of inner cylindrical member 16 and a surface defining first lumen 22 may be solid, and first lumen 22 may be a bore formed in inner cylindrical member 16. In another example, a space between an exterior surface of inner cylindrical member 16 and a surface defining first lumen 22 may be hollow. In such a case, first lumen 22 may be formed by a longitudinal tube within inner cylindrical member 16.

First lumen 22 may be open to an exterior of inner cylindrical member 16 on a proximal end of first lumen 22 via one or more proximal apertures 24. For example, first lumen 22 may be fluidly connected to proximal aperture(s) 24 via a second, proximal lumen (not shown) which may be transverse to first lumen 22. For example, the second, lumen may be perpendicular to first lumen 22 (extending into the page in FIG. 9). First lumen 22 may be open to an area exterior of inner cylindrical member 16 on a distal end of first lumen 22 via one or more distal apertures 26. First lumen 22 may be fluidly connected to distal aperture(s) 26 via a third, distal lumen (not shown) which may be transverse to first lumen 22. For example, the third, distal lumen may be perpendicular to first lumen 22 (extending into the page in FIG. 9). In some embodiments described herein, aperture may be used interchangeably with orifice. Further, in one or more embodiments described herein, inner cylindrical member may be used interchangeably with valve stem. Accordingly, for example, an aperture of an inner cylindrical member may be equivalent to an orifice of a valve stem.

Inner cylindrical member 16 may have disposed on it a first distal seal 32, a second distal seal 34, and a third distal seal 36. Distal seals 32, 34, 36 may be made from elastomeric material. Distal seals 32, 34, 36 may be identical to one another and may be, for example, O-rings. In some embodiments, distal seals may be formed as discs, such that edges of the disc seals may contact and conform to the valve well to form seals. Discs, or "wiper" seals, may accommodate for greater manufacturing tolerances. Distal seals 32, 34, 36 may be disposed in circumferential, annular grooves or indentations on inner cylindrical member 16 along the central longitudinal axis and spaced a distance "D" apart. The distance "D" between each of distal seals 32, 34, 36 may be the same, although the distance may be different, and/or any distance apart from each other for sealing the valve 10. An outer surface of distal seals 32, 34, 36 may be configured of a size, and/or seals 32, 34, and 36 may be made of a material and/or have a property (such as an appropriate durometer value), such that the distal seals 32, 34, 36 have an interference fit with an inner wall 38 (see FIGS. 9 and 10) of an endoscope valve cylinder 39 when valve 10 is inserted in endoscope valve cylinder 39. The interference fit may be loose enough so that inner cylindrical member 16 may slidably move relative to wall 38 in response to an application of force (e.g., user insertion/removal from endoscope valve cylinder 39) but tight enough so that the valve 10 remains stationary in endoscope valve cylinder 39, and fluids cannot flow longitudinally between a radially outermost surface of seals 32, 34, 36 and wall 38. Third distal seal 36 may be disposed near to a distal end 14 of valve 10 and distal to distal aperture 26. Second distal seal 34 may be proximal of third distal seal 36 and proximal to distal aperture 26. First distal seal 32 may be proximal of second distal seal 34 but still distal of proximal aperture 24.

Referring to FIGS. 9 and 10, a proximal seal 42 may also be disposed on inner cylindrical member 16. Proximal seal 42 may have any of the properties of distal seals 32, 34, 36. For example, proximal seal 42 may be an elastomeric O-ring and may be disposed in an annular circumferential groove or indentation of inner cylindrical member 16. An outer surface of proximal seal 42 may be configured of a size and/or material such that the proximal seal 42 has an interference fit with wall 38 (see FIGS. 9 and 10) when valve 10 is inserted in endoscope valve cylinder 39. The interference fit may be loose enough so that inner cylindrical member 16 may slidably move relative to endoscope valve cylinder wall 38 in response to an application of force (e.g., user insertion/removal from endoscope valve cylinder 39) but tight enough so that the valve 10 remains stationary in endoscope valve cylinder 39, and fluids cannot flow longitudinally between a radially outermost surface of proximal seal 42 and wall 38. Proximal seal 42 may have a larger inner diameter than distal seals 32, 34, 36 due to a wider diameter of inner cylindrical member 16 at a location of proximal seal 42. Proximal seal 42 may have a larger outer diameter than distal seals 32, 34, 36 due to a wider space defined by wall 38 at the location of seal 42 compared to a space defined by wall 38 at the location of seals 32, 34, 36.

Inner cylindrical member 16 may also be fitted with a one-way seal 62, which may be disposed between first distal seal 32 and proximal seal 42. One-way seal 62 may be formed of an elastomeric material, and may be annularly shaped, having an inner surface and an outer surface. One-way seal 62 may be stretchable so that a central opening of one-way seal 62 may be expanded so as to fit over inner cylindrical member 16. One-way seal 62 may be disposed in a groove or indentation of inner cylindrical member 16. The inner surface of one-way seal 62 may be sized so that there is a slight interference between an external surface of inner cylindrical member 16 and the inner surface of one-way seal 62, so that a tight seal is formed. An outer diameter of one-way seal 62 may be sized so as to form a slight interference fit with wall 38. A thin flap 63 of one-way seal 62 may extend radially outward from inner cylindrical member 16 at an angle transverse to a longitudinal axis of inner cylindrical member 16. For example, the thin flap may extend at an angle between 10 degrees and 80 degrees relative to a longitudinal axis of inner cylindrical member 16. The flap of one-way seal 62 may be expandable so that when fluid (e.g., water or air) moves in a distal direction, a positive pressure will expand the flap, maintaining a seal between one-way seal 62 and wall 38. Fluid moving proximally will also create a positive pressure, but the positive pressure will produce a force normal to a longitudinal axis of inner cylindrical member 16 to radially compress the flap of one-way seal 62 toward inner cylindrical member 16. Thus, fluid (e.g., air or water) is permitted to move proximally past one-way seal 62, between one-way seal 62 and wall 38.

Proximal aperture 24 may be disposed between one-way seal 62 and proximal seal 42. Distal aperture 26 may be disposed between third distal seal 36 and second distal seal 34.

Referring back to FIG. 8, an outer cylindrical member 18 (e.g., spring cap) may be coupled to a portion of inner cylindrical member 16 on proximal end 12 of valve 10. Outer cylindrical member 18 may be formed of an elastomeric material such as, for example, silicone rubber, urethane rubber, natural rubber, nitrile rubber, butyl rubber, any combinations thereof, and/or any material exhibiting the appropriate material properties including elongation/recovery characteristics. Outer cylindrical member 18 may be a single, unitary structure formed from a single, continuous piece of material and may be, for example, molded, extruded, or otherwise formed. Outer cylindrical member 18 may be a cap.

As shown particularly in FIGS. 9 and 10, outer cylindrical member 18 may have an interior chamber 72 that may extend from a proximal portion 74 to a distal portion 76 of outer cylindrical member 18. Interior chamber 72 may be open on distal portion 76 (e.g., an annular gap exists between the distal end of outer cylindrical member 18 and inner cylindrical member 16) and closed on proximal portion 74 (e.g., the proximal end of outer cylindrical member 18 is closed around the proximal end of member 16). An annular wall 82 of outer cylindrical member 18 may extend from a radially outer surface of outer cylindrical member 18 to a radially inner surface of outer cylindrical member 18. The radially inner surface of outer cylindrical member 18 may define interior chamber 72. Interior chamber 72 may be sized to receive a proximal portion 84 of inner cylindrical member 16. A surface defining interior chamber 72, a radially inner surface of outer cylindrical member 18, and a radially inner surface of an interior of annular wall 82 may be discussed interchangeably herein and may refer to the same or similar structures.

Outer cylindrical member 18 and inner cylindrical member 16 may have corresponding features for coupling an outer surface of proximal portion 84 of outer cylindrical member 18 with a surface defining interior chamber 72. For example, an outer surface of proximal portion 84 of inner cylindrical member 16 may have one or more annular indentations or channels 86, and an inner surface of proximal portion 74 of outer cylindrical member 18 may have one or more corresponding annular protrusions 88 that mate with the indentations 86 on inner cylindrical member 16. When inner cylindrical member 16 is inserted into outer cylindrical member 18, indentation 86 of inner cylindrical member 16 may mate with protrusion 88 of outer cylindrical member 18 to retain inner cylindrical member 16 within interior chamber 72 of outer cylindrical member 18. Additionally, or alternatively, inner cylindrical member 16 may have protrusions and outer cylinder may have one or more indentations or channels that may achieve the same mating function described above. Alternatively, other features (e.g., tabs, notches, or the like) may be used to fixedly attach the proximal end of the inner cylindrical member 16 and the outer cylindrical member 18. In various embodiments, annular protrusions 88, or any alternative structures used for annular protrusions 88, may include, or be referred to as, a first connector portion.

Proximal portion 74 of outer cylindrical member 18 may have features that are complementary to a shape of endoscope valve cylinder 39. For example, as shown in FIGS. 9 and 10, outer cylindrical member 18 may have a feature 79, such as an annular indentation or channel, to releasably receive a portion of endoscope valve cylinder 39 and to fix outer cylindrical member 18 relative to endoscope valve cylinder 39. Any alternative structures may be used for feature 79, including grooves, protrusions, lips, rims, tabs, slots, or the like. In some embodiments, feature 79, or any alternative structures used for feature 79, may include, or be referred to as, a second connector portion.

A thickness of wall 82 may vary longitudinally along proximal outer cylindrical member 18. A thickness of wall 82 may be a distance between an outer surface of outer cylindrical member 18 and an inner surface of outer cylindrical member 18. A first portion 90 and a third portion 91 may have relatively thicker wall 82. In other words, a distance between an outer surface and an inner surface of inner cylindrical member 18 may be relatively large at first portion 90 and third portion 91. Outer cylindrical member 18 may have relatively thinner portions of wall 82 at second portion 92 (e.g., a midsection) of outer cylindrical member 18 between first portion 90 and third portion 91. Each of first portion 90, second portion 92, and third portion 91 may be between protrusion 88 and feature 79. For example, first portion 90 may be distal to protrusion 88, second portion 92 may be distal to first portion 90, third portion 91 may be distal to second portion 92, and feature 79 may be distal to third portion 91. In various embodiments, the first portion 90, second portion 92, and third portion 91 may be collectively referred to as the spring portion. In many embodiments, in response to a force exerted on the proximal surface, the annular wall 82 is expandable radially outward at the second portion.

At any longitudinal position along wall 82, its thickness may be constant, or its thickness may vary. An inner surface of outer cylindrical member 18 may taper radially outwardly from first portion 90 to second portion 92 and from third portion 91 to second portion 92. A thickness of wall 82 of outer cylindrical member 18 also may taper between first portion 90 and second portion 92 and between third portion 91 and second portion 92. As discussed in further detail below with respect to FIG. 10, a tapered profile of walls 82 may facilitate radially outward displacement of walls 82 about second portion 92 when an axial force is applied to proximal portion 84.

FIG. 9 shows valve 10 in a first configuration, in which air is flushed through both a water channel and an air channel of an endoscope. Valve 10 may be in the first configuration when it is first inserted into the scope. As discussed in further detail below, valve 10 may be returned to the first configuration after being operated in the second configuration so as to flush water out of both the air and water channels of the endoscope. In the first configuration, outer cylindrical member 18 may be in an uncompressed (e.g., relaxed) state. Outer cylindrical member 18 may be biased to the uncompressed state of the first configuration of valve 10. In the first configuration, third distal seal 36 may be positioned proximal to a water inlet A of endoscope valve cylinder 39 and also distal to a water outlet B of endoscope valve cylinder 39. Second distal seal 34 may be proximal of water outlet B but distal to air inlet C. First distal seal 32 may also be distal to air inlet C. One-way seal 62 may be proximal of air inlet C and distal to air outlet D.

Thus, in the first configuration, water from water inlet A may not move proximally past third distal seal 36 and may thus not move to water outlet B. Air from air inlet C may not move distally along an outer surface of inner cylindrical member 16 due to first distal seal 32. However, air from air inlet C may move proximally past one-way seal 62. Air may thus pass into air outlet D and also into proximal aperture 24. Air that has passed into proximal aperture 24 may pass distally through first lumen 22 and out of distal aperture 26. Because distal aperture 26 is between third distal seal 36 and second distal seal 34, the air exiting distal aperture 26 may not move proximally or distally along an outer surface of inner cylindrical member 16. However, the air exiting distal aperture 26 may exit the water outlet B.

FIG. 10 shows valve 10 in a second, compressed configuration, in which water is flushed down the air channel. Outer cylindrical member 18 is compressed about midsection 92. The tapered wall 82 of outer cylindrical member 18 facilitate the compression of outer cylindrical member 18 to the second configuration. Second portion 92 may bulge outward due to the relative thinness of wall 82 at second portion 92. An entirety of inner cylindrical member 16 is shifted distally by a same amount in which outer cylindrical member 18 is compressed. Distal end 14 of valve 10 may rest along a distal surface of endoscope valve cylinder 39. Proximal seal 42 may be shifted distally to be positioned proximal of water outlet D. One-way seal 62 may be shifted distally relative to the first configuration, so that air from air inlet C may not move past one-way seal 62 because a distal portion of one-way seal 62 fits in a narrowed, tapered region of endoscope valve cylinder 39 so that air cannot pass proximally past the distal portion of one-way seal 62 to reach the proximal movable flap portion of one-way seal 62.

In the second configuration, third distal seal 36 may be distal to water inlet A, and second distal seal 34 may be proximal of water inlet A. Therefore, water from water inlet A may enter proximally of third distal seal 36 but may not move proximally past second distal seal 34 along an outer surface of inner cylindrical member 16. However, water may enter distal aperture 26 and travel through first lumen 22 and through proximal aperture 24. After water exits proximal aperture 24, the water may not travel distally past one-way seal 62. However, water may travel out air outlet D to flush out the air channels of an endoscope.

After a procedure using an endoscope is completed, an operator may remove an air/water valve used during the procedure from valve cylinder 39. The operator may then insert valve 10 into valve cylinder 39. Distal portion 76 of outer cylindrical member 18 may be secured to valve cylinder 39 using the protrusions or grooves in the inner surface of distal portion 76 of the outer cylindrical member. Valve 10 may be inserted into valve cylinder 39 in the first configuration of valve 10 (e.g., FIG. 9). An operator may press down on a proximal surface of outer cylindrical member 18 and/or on a proximal surface of inner cylindrical member 16 (e.g., at the top of the FIGS. 8-14). Pressing distally on those proximal surfaces causes compression of outer cylindrical member 18 so that wall 82 of outer cylindrical member 18 bulges radially outward (e.g., FIG. 10). For example, wall 82 of outer cylindrical member 18 may buckle (e.g., bend, fold, compress, or at least partially collapse like an accordion) at a predetermined location, with second portion 92 bulging radially outward where wall 82 is thinnest. Inner cylindrical member 16 may simultaneously move distally relative to endoscope valve cylinder 39. Valve 10 may be maintained in the second, compressed configuration for a predetermined amount of time (e.g., thirty seconds) so as to flush water through an air channel of the endoscope, thereby removing debris from the air channel. The amount of time needed for flushing may be dependent upon a length of tubing in the endoscope to reach the distal end. Due to shape memory features or other material features of outer cylindrical member 18, valve 10 may be biased to the first configuration (FIG. 9).

When an operator releases pressure from the proximal most surface of valve 10, it may return to the first configuration due to shape memory or other biasing properties of outer cylindrical member 18. The properties of outer cylindrical member 18 are such that valve 10 may not require a separate spring to return to the relaxed configuration of FIG. 9. Thus, the functionality of other valves may be accomplished alone by outer cylindrical member 18. The valve may be maintained in the first configuration for a predetermined duration so as to use air to flush water out of both the air and water channels. Following completion of flushing of water through the air channel and air through the air and water channels, valve 10 may be removed from the endoscope valve cylinder 39. Disposable valve 10 may be discarded, or reusable valve 10 may be reprocessed for subsequent use.

Figure 11:
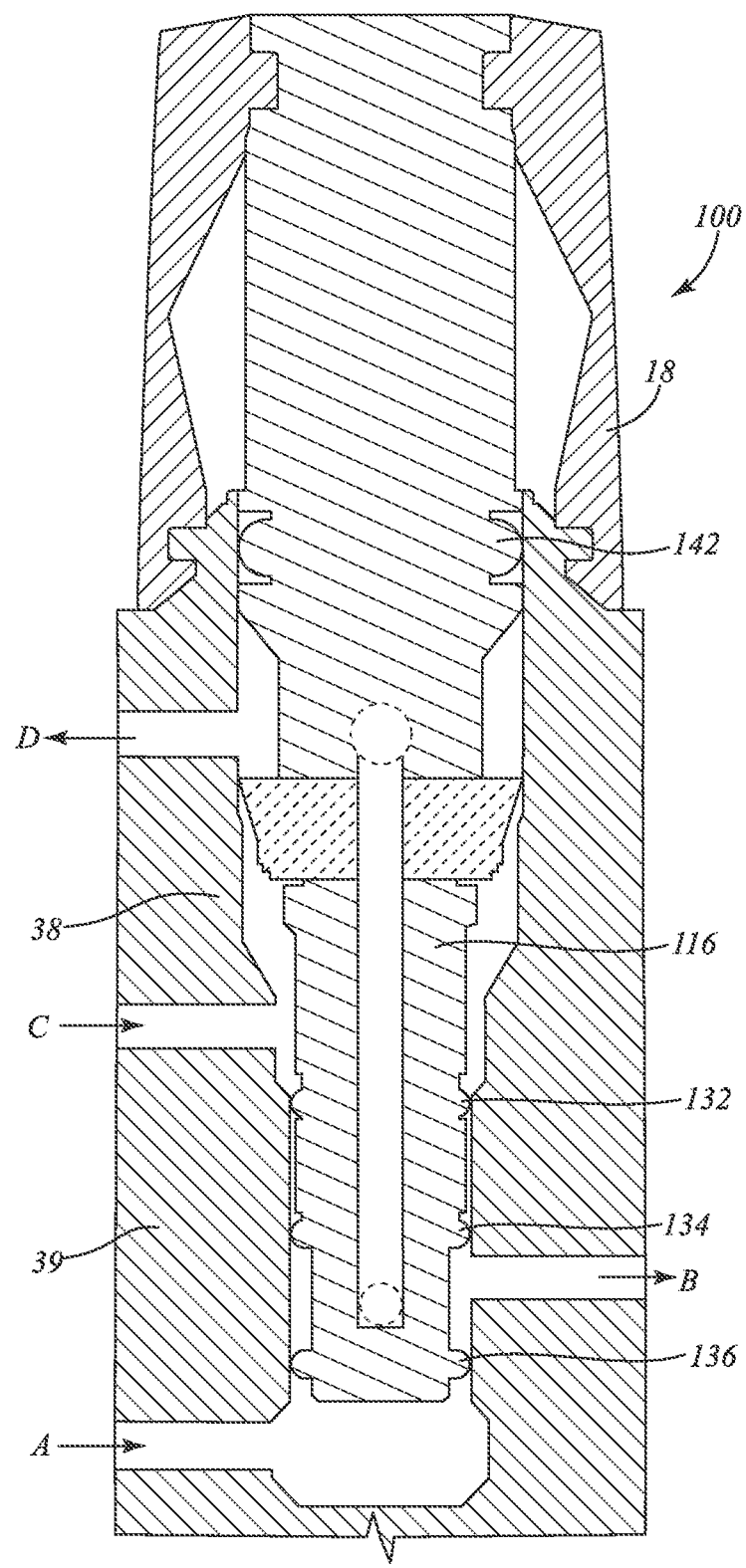
FIGS. 11 and 12 illustrate cross-sectional view of a second exemplary valve according to the present disclosure described herein.
Figure 12:
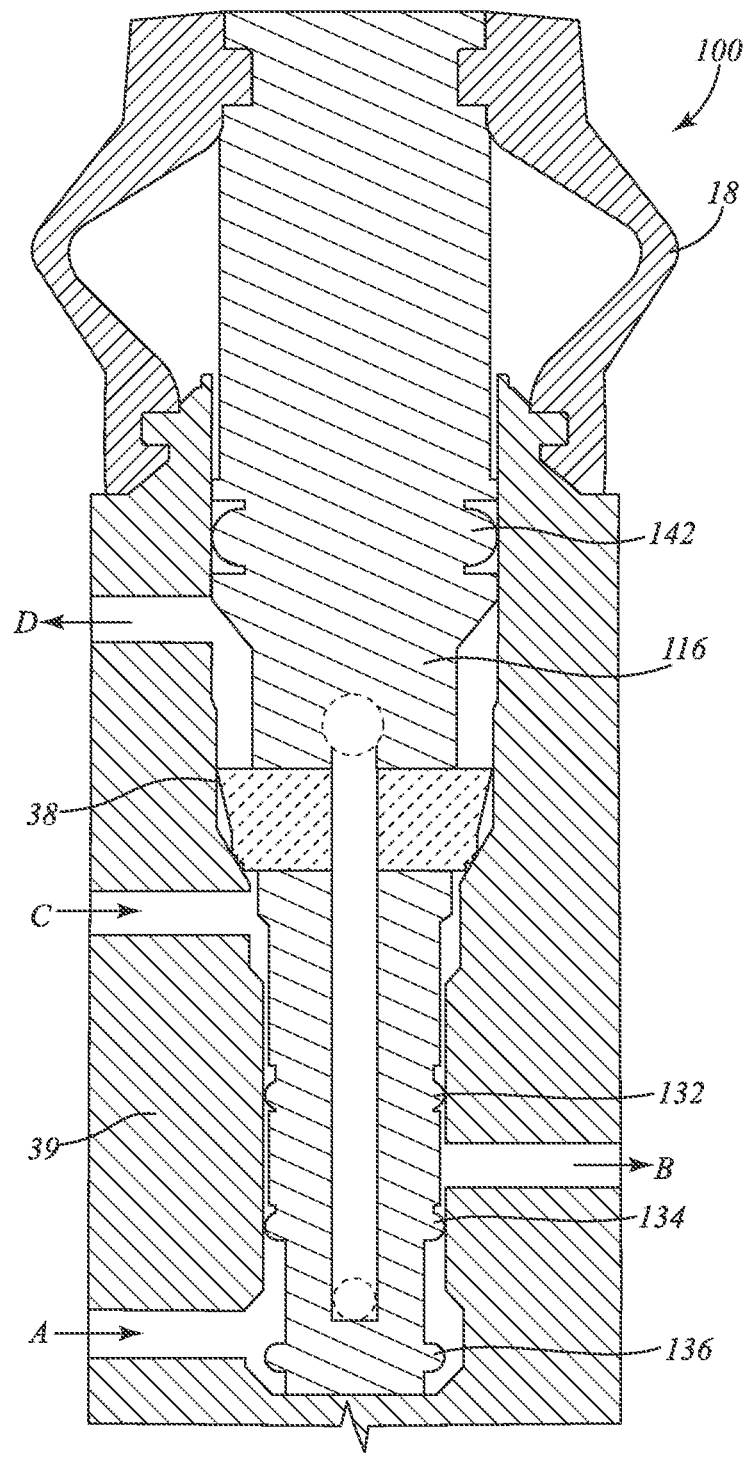

FIGS. 11 and 12 show an alternative exemplary valve 100. Valve 100 may have any of the qualities, features, and/or structure of valve 10, above. In particular, valve 100 may have an identical outer cylindrical member 18 (e.g., spring cap) to valve 10, above. Valve 100 may have an inner cylindrical member 116, which may have any of the qualities of inner cylindrical member 16, except for as outlined herein. Instead of seals 32, 34, 36, 42 inner cylindrical member 16 may be molded so as to achieve the same functionality of one or more of seals 32, 34, 36, 42. For example, inner cylindrical member 116 may have one or more of proximal circumferential ring 142, first distal circumferential ring 132, second distal circumferential ring 134, and third circumferential ring 136 integrally molded with member 116. In some embodiments, first, second, and third distal circumferential rings 132, 134, 136 and proximal circumferential ring 142 may be referred to as seals 132, 134, 136, 142 First, second, and third distal circumferential rings 132, 134, 136 may be located in a position on inner cylindrical member 116 corresponding to placement of distal seals 32, 34, 36 on inner cylindrical member 16. Distal circumferential rings 132, 134, 136 may extend radially from the outer surface of inner cylindrical member 116 and may be raised, annular features. Distal circumferential rings 132, 134, 136 may create a slight interference fit between an outer surface of inner cylindrical member 116 and an inner wall 38 endoscope valve cylinder 39 so that a slidable seal is formed at each ring 132, 134, 136. Distal circumferential rings 132, 134, 136 may replace all of distal seals 32, 34, 36 or a subset of distal seals 32, 34, 36.

In some embodiments, one or more of seals 132, 134, 136, 142 and/or seals 32, 34, 36, 42 may be formed as a single, independent component. See e.g., FIGS. 21A-22B. In various embodiments, one or more of seals 132, 134, 136, 142 and/or one or more of seals 32, 34, 36, 42 may include wiper seals that allow a wider range of diameters with consistent friction for sealing. See e.g., FIG. 19. In many embodiments, one or more of seals 132, 134, 136, 142 and/or one or more of seals 32, 34, 36, 42 may be formed via overmolding. See e.g., FIGS. 19 and 20.

In addition, instead of proximal seal 42 of valve 10, inner cylindrical member 16 may be molded so as to achieve the same functionality of proximal seal 42. For example, inner cylindrical member 116 may have a proximal circumferential ring 142. Proximal circumferential ring 142 may be located in a position on inner cylindrical member 116 corresponding to placement of proximal seal 42 on inner cylindrical member 16. Proximal circumferential ring 142 may extend radially from an outer surface of inner cylindrical member 116 and may be a raised, annular feature. Proximal circumferential ring 142 may create a slight interference fit between an outer surface of inner cylindrical member 116 and an inner wall 38 of endoscope valve cylinder 39 so that a slidable seal is formed.

Valve 100 may use any combination of molded seals and elastomeric seals. For example, inner cylindrical member 116 may have one or more distal circumferential rings 132, 134, 136 and an elastomeric proximal ring. Alternatively, inner cylindrical member 116 may have a molded proximal circumferential ring 142 and elastomeric distal seals. Any combination of molded rings and elastomeric seals may be used. Valve 100 may function in the same way as valve 10, described above, with FIG. 11 showing a relaxed state and FIG. 12 showing a compressed state.

Figure 13:
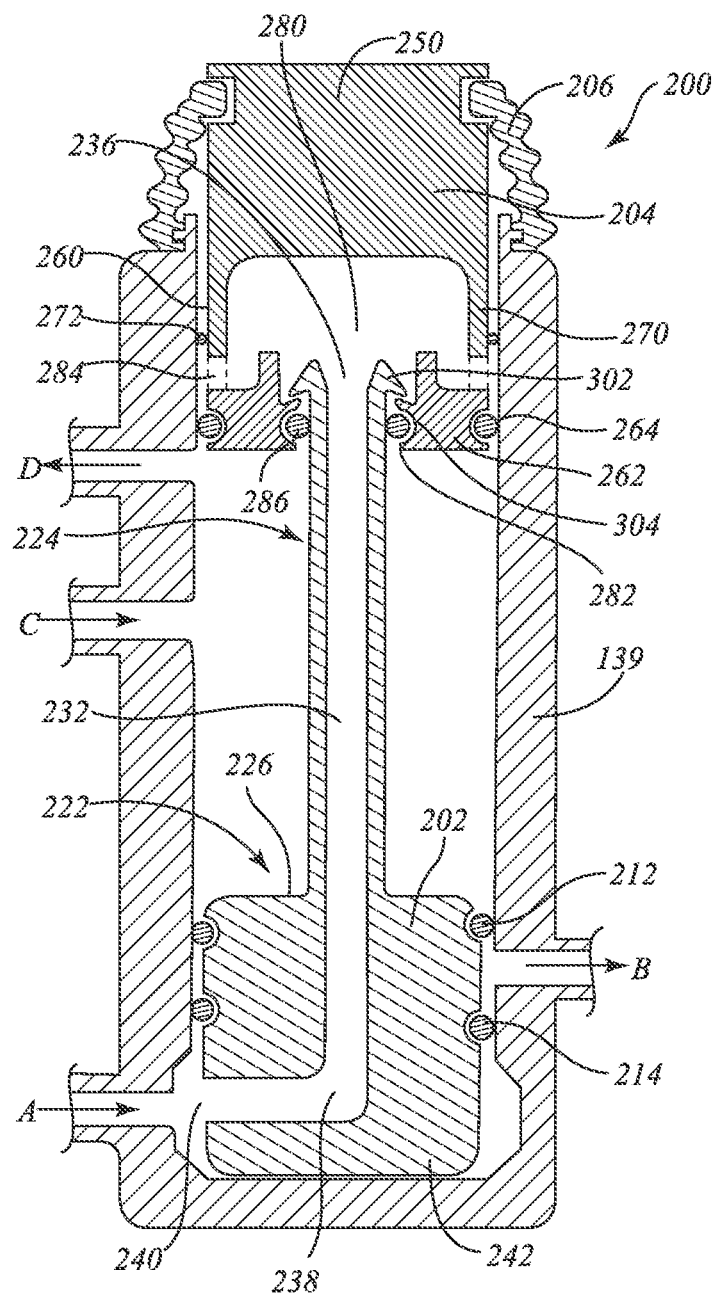
FIGS. 13 and 14 illustrate cross-sectional view of a third exemplary valve according to the present disclosure described herein.
Figure 14:
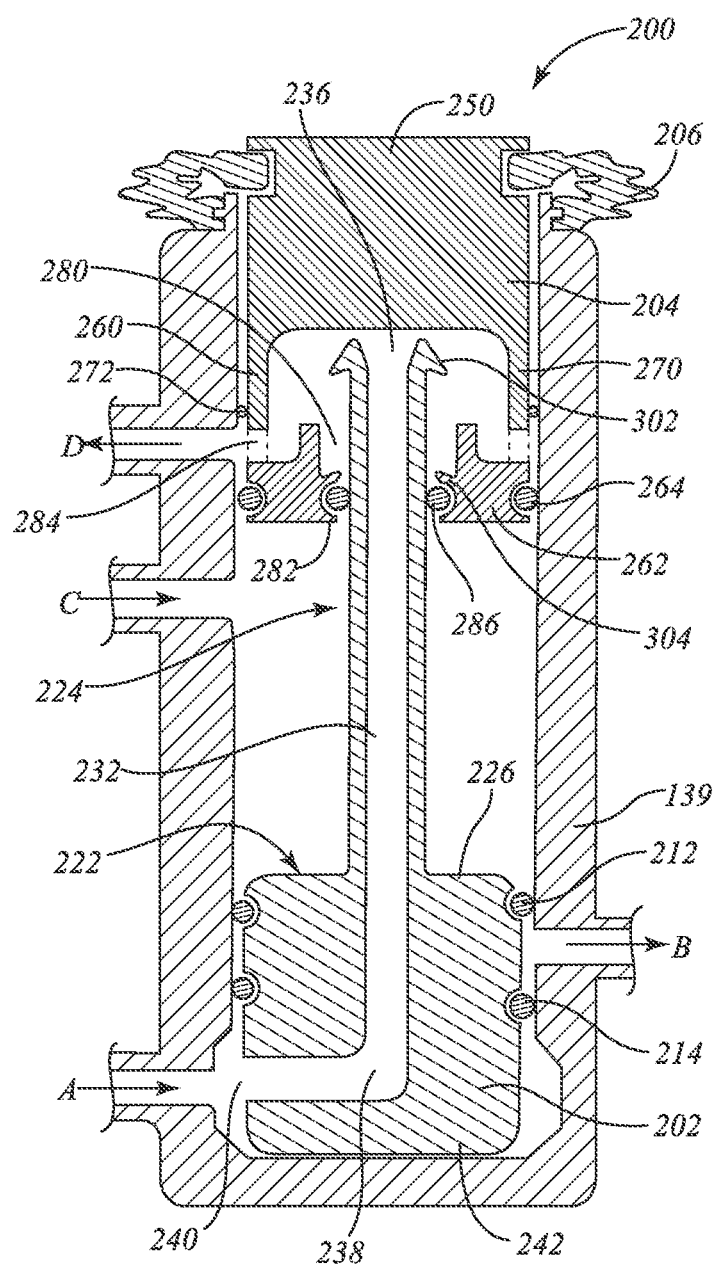

FIGS. 13 and 14 show first (FIG. 13) and second (FIG. 14) configurations of an alternative valve 200. Valve 200 may have a distal member 202, a proximal member 204, and a proximal skirt 206.

Distal member 202 may be formed of any of the materials described above with respect to inner cylindrical member 16. A body of distal member 202 may be a single, unitary structure formed of a single, continuous material. Distal member 202 may be fitted with a first distal seal 212 and a second distal seal 214, each of which may have any of the properties of distal seals 32, 34, 36, or proximal seal 42, described above, or of circumferential rings 132, 134, 136, 142. First and second distal seals 212, 214 may fit in annular grooves or indentations on an outer surface of distal member 202. First and second distal seals 212, 214 may form a slidable interference fit between an outer surface of distal member 202 and an inner surface of a valve cylinder 139 of an endoscope so that fluids (e.g., air and water) cannot move between distal seals 212, 214 and walls of endoscope valve cylinder 139.

Distal member 202 may have a distal portion 222 and a proximal portion 224. Distal portion 222 may have a greater outer diameter than proximal portion 224. A shoulder 226 may form a boundary between distal portion 222 and proximal portion 224. Alternatively, there may be a tapered section between distal portion 222 and proximal portion 224 or another transition between distal portion 222 and proximal portion 224. Distal member 202 may have a first central lumen 232. At least a portion of first central lumen 232 may extend along a central longitudinal axis of distal member 202, through distal portion 222 and proximal portion 224. First central lumen 232 may have a proximal opening 236 on a proximal end of proximal portion 224. A proximal opening 236 of first central lumen 232 may be surrounded by a lip portion 302 of proximal portion 224 that protrudes from an outer surface of proximal portion 224. First central lumen 232 may include a bend 238 near a distal end 242 of distal portion 222. First central lumen 232 may extend from bend 238 to an outer (side) surface of distal member 202. A distal aperture 240 may fluidly connect an area exterior to distal member 202 to a distal end of first central lumen 232.

Distal member 202 may remain fixed during operation of valve 200 when valve 200 is positioned within endoscope valve cylinder 139. For example, a distal end 242 of distal member 202 may rest on a distal surface of endoscope valve cylinder 139. Both first and second distal seals 212, 214 may be proximal of water inlet A. First distal seal 212 may be proximal to water outlet B, and second distal seal 214 may be distal to water outlet B. Thus, water may be prevented from moving proximally between an outer surface of distal member 202 and a wall of endoscope valve cylinder 139. Fluids, such as air and water, may be prevented from entering water outlet B. Distal aperture 240 may be aligned with water inlet A so that water may travel proximally through first central lumen 232.

Proximal member 204 may have a proximal finger button 250 and a distal body 260. Body 260 may extend distally from finger button 250. In some embodiments, finger button 250 may comprise an interface member. Body 260 may include a distal flange 262. Proximal member 204 may be a single, unitary structure formed of a single, continuous material and may be made of any material that distal member 202 may be made from. Distal flange 262 may be fitted with a body seal 264. Body seal 264 may have any of the qualities of first distal seal 212 and second distal seal 214. First body seal may be affixed to body 260. Body seal 264 may be disposed on an outer surface of flange 262. For example, an outer surface of flange 262 may include a groove or indentation in which body seal 264 fits so as to secure body seal 264. Body seal 264 may be configured so that a slidable interference fit is created between body seal 264 and an inner surface of endoscope valve cylinder 139 when valve 200 is disposed in endoscope valve cylinder 139. Fluids (e.g., air or water) may be prevented from traveling between body seal 264 and an inner surface of the endoscope valve cylinder.

A circumferential wall 270 may extend from a distal surface of finger button 250 around distal body 260. An outer surface of wall 270 may be fitted with a wall seal 272. Wall seal 272 may have any of the properties of first distal seal 212, second distal seal 214, or body seal 264. Wall seal 272 may be affixed to an outer surface of wall 270. For example, an outer surface of wall 270 may include a groove or indentation in which wall seal 272 fits so as to secure wall seal 272. Wall seal 272 may be configured so that a slidable interference fit is created between wall seal 272 and an inner surface of endoscope valve cylinder 139 when valve 200 is disposed in endoscope valve cylinder 139. Fluids (e.g., air or water) may be prevented from traveling between wall seal 272 and inner surface of endoscope valve cylinder 139.

Body 260 may have a chamber 280 extending from a distal end of body 260 to a proximal end of body 260. Chamber 280 may be open on a distal end 282 of body 260. Chamber 280 may also be open to an area between an outer surface of body 260 and wall 270 via one or more body apertures 284. Chamber 280 may receive proximal portion 224 of distal member 202. Chamber 280 may be in fluid communication with first central lumen 232. Therefore, first central lumen 232 may be in fluid communication with one or more body apertures 284. Body apertures 284 may not continue around a complete circumference of body 260, so dotted lines are shown on FIGS. 13 and 14 to show where walls may be present along alternate cross-sections of valve 200. A lumen seal 286 may be between an inner surface of body 260 and an outer surface of proximal portion 224. Lumen seal 286 may create a slidable interference fit between the inner surface of body 260 and the outer surface of proximal portion 224 so that fluids (e.g., air and water) cannot pass lumen seal 286. Lumen seal 286 may be fixed to, for example, an inner surface of body 260. For example, body 260 may include a groove or indentation in which lumen seal 286 may be received. Lumen seal 286 may be axially aligned with body seal 284. Lip 302 surrounding proximal opening 236 of proximal portion 224 may interact with a rim 304 of chamber 280 so that lip 302 may not move distally past rim 304. Lip 302 may have features such that lip 302 may move proximally past rim 304 (e.g., to allow manufacture of valve 200) but so that lip 302 cannot move distally past rim 304 so that valve 200 remains one, united piece during handling.

Valve 200 may also include skirt 206. Skirt 206 may extend distally from a proximal end of finger button 250. For example, finger button 250 may include a groove in which a protrusion of skirt 206 may be received. A distal end of skirt 206 may include features for mating skirt 206 to valve cylinder 139 of an endoscope. For example, skirt 206 may include a groove for receiving a protrusion of valve cylinder 139 of the endoscope. It is also understood that skirt 206 may include a protrusion for receiving a groove of valve cylinder 139, or any other complementary releasable attachment mechanism. Accordingly, in some embodiments, the proximal end of skirt 206 may include, or be referred to as, a first connector portion and the distal end of skirt 206 may include, or be referred to as, a second connector portion. Skirt 206 may be formed from any suitable material, including the materials described above with respect to cylindrical member 18. Skirt 206 may have any of the properties or shapes of cylindrical member 18. Skirt 206 may have accordion type folds or may be corrugated. Skirt 206 may be formed of a shape memory material or may otherwise be configured so that skirt 206 is biased in a configuration in which it is expanded along a longitudinal direction of skirt 206. Accordingly, in some embodiments, skirt 206 may include a spring portion (e.g., the accordion type folds).

Referring specifically to FIG. 13, a first configuration of valve 200 is shown. In the first configuration, skirt 206 may be longitudinally expanded, and proximal body 260 may be configured so that body seal 264 and wall seal 272 are both proximal of air inlet C and air outlet D. First and second distal seals 212, 214 are, in both configurations (the FIG. 13 and FIG. 14 configurations), distal of air inlet C and air outlet D. Therefore, air from air inlet C may freely travel out of air outlet D and into an air channel of the endoscope. However, water that travels proximally through first central lumen 232 may not travel distally past body seal 264. Water also cannot travel proximally past wall seal 272. Therefore, water from water inlet A may not exit endoscope valve cylinder 139.

Referring specifically to FIG. 14, a second, compressed configuration of valve 200 is shown. In the second configuration, proximal body 260 is moved in a distal direction, compressing skirt 206. In the second configuration, body seal 264 is distal to air outlet D but proximal to air inlet C, and wall seal 272 remains proximal to air outlet D. Aperture 284 may be aligned with air outlet D. Air from air inlet C may not travel proximally past body seal 264 and therefore cannot exit endoscope valve cylinder 139. Water exiting first central lumen 232 may pass through body aperture(s) 284, and through aperture 284 to air outlet D. Therefore, in the second configuration, water may pass through an air channel of the endoscope.

After a procedure using an endoscope is completed, an operator may remove an air/water valve used during the procedure from the endoscope's valve cylinder 139. The operator may then insert valve 200 into valve cylinder 139. Skirt 206 may be secured to valve cylinder 139 using the mechanisms described above. Valve 200 may be inserted into valve cylinder 139 in the first configuration of valve 200. An operator may press down on a button 250, thereby pressing down on proximal member 204 and transitioning valve 200 to the second configuration of FIG. 14. Pressing button 250 may also cause compression of skirt 206. Valve 200 be maintained in the second configuration for a predetermined amount of time (e.g., thirty seconds) so as to flush water through an air channel of the endoscope, thereby removing debris from the air channel. Following flushing of water through the air channel, valve 200 may be disposed or reprocessed.

One or more of the features for differentiating procedural valves, described above, may be incorporated into or implemented with the valve designs of FIGS. 15-23, described below. For example, the indicator depicted in the top surface of the interface member in FIGS. 15 and 16. In many embodiments, one or more components of the medical cleaning valve assemblies of FIGS. 1A-14 may be the same or similar in construction, function, and/or appearance as described with respect to FIGS. 15-23. In FIGS. 15-17 and 23, unless otherwise specified, the dimensions are in inches; and in FIG. 18, unless otherwise specified, the dimensions are in millimeters. Although dimensions are discussed in terms of inches or millimeters, inches and millimeters can readily be converted between based on 1 inch equaling 25.4 mm. All dimensions are illustrative only, and other dimensions may be more suited to a particular application. Also, dimensions described may be approximations that encompass tolerances, e.g., tolerances allow for plus or minus percentage variations from the described values. Unless otherwise noted, tolerances may be as follows: "X" is ±0.25 mm; "X.X" is +0.1 inches or ±0.1 mm; "X.XX" is ±0.01 inches or +0.05 mm; "X.XXX" is ±0.05 inches or ±0.01 mm; "X.XXXX" is ±0.0005 inches; and angles may be ±2 degrees.

Figure 15:
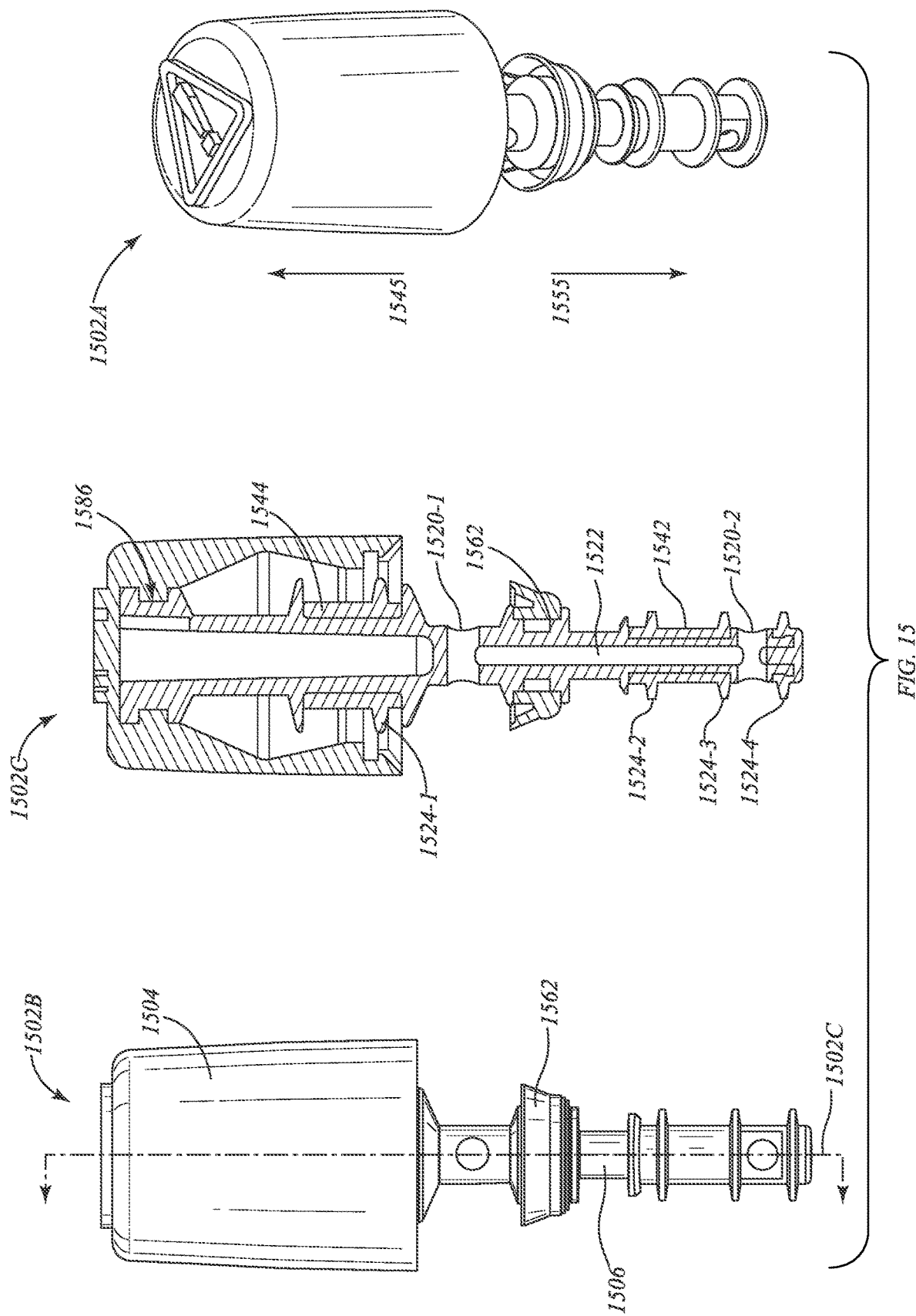
FIG. 15 illustrates various aspects of an exemplary cleaning valve assembly according to the present disclosure described herein.
Figure 16:
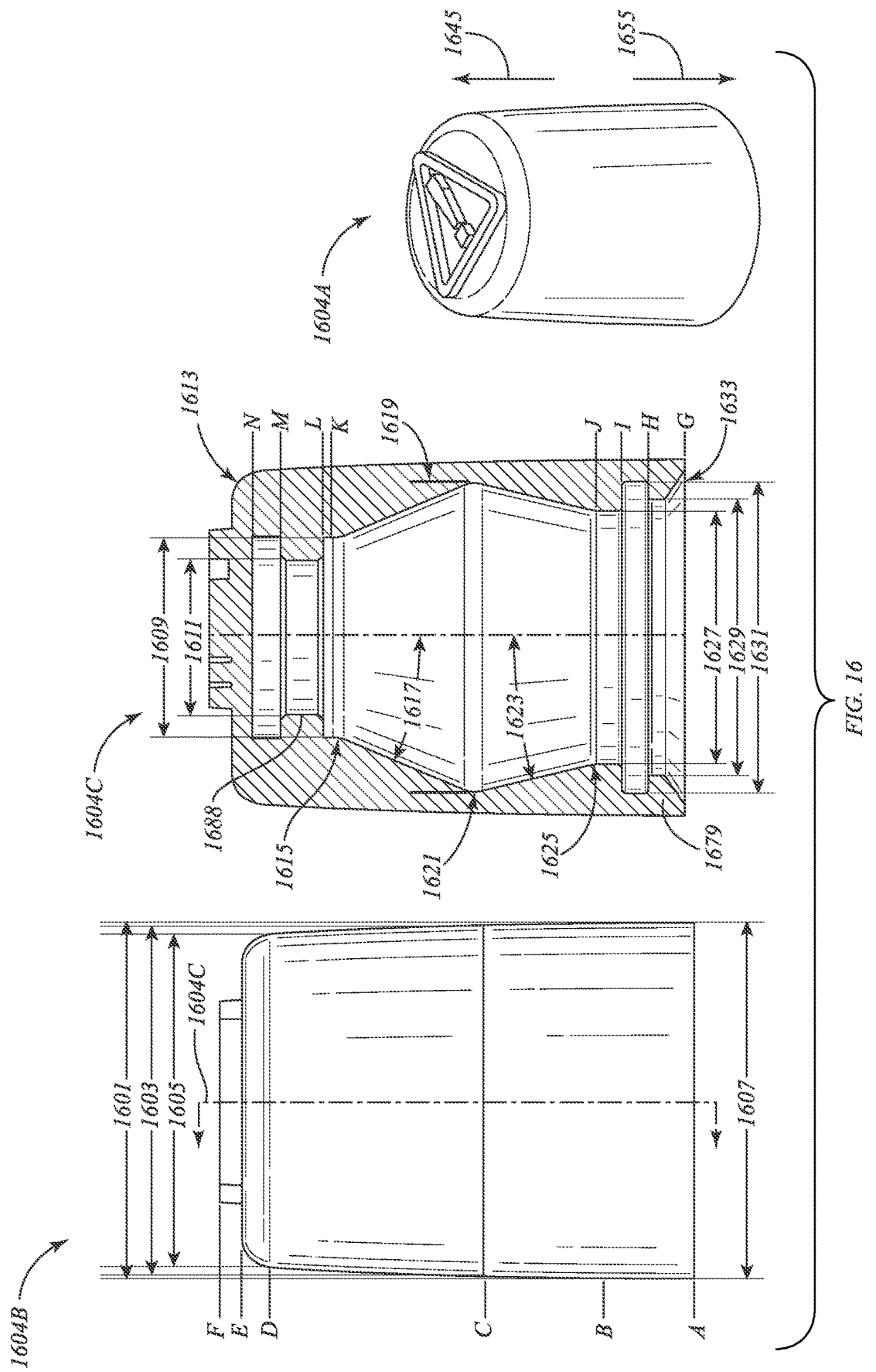
FIG. 16 illustrates various aspects of an exemplary interface member according to the present disclosure described herein.
Figure 17:
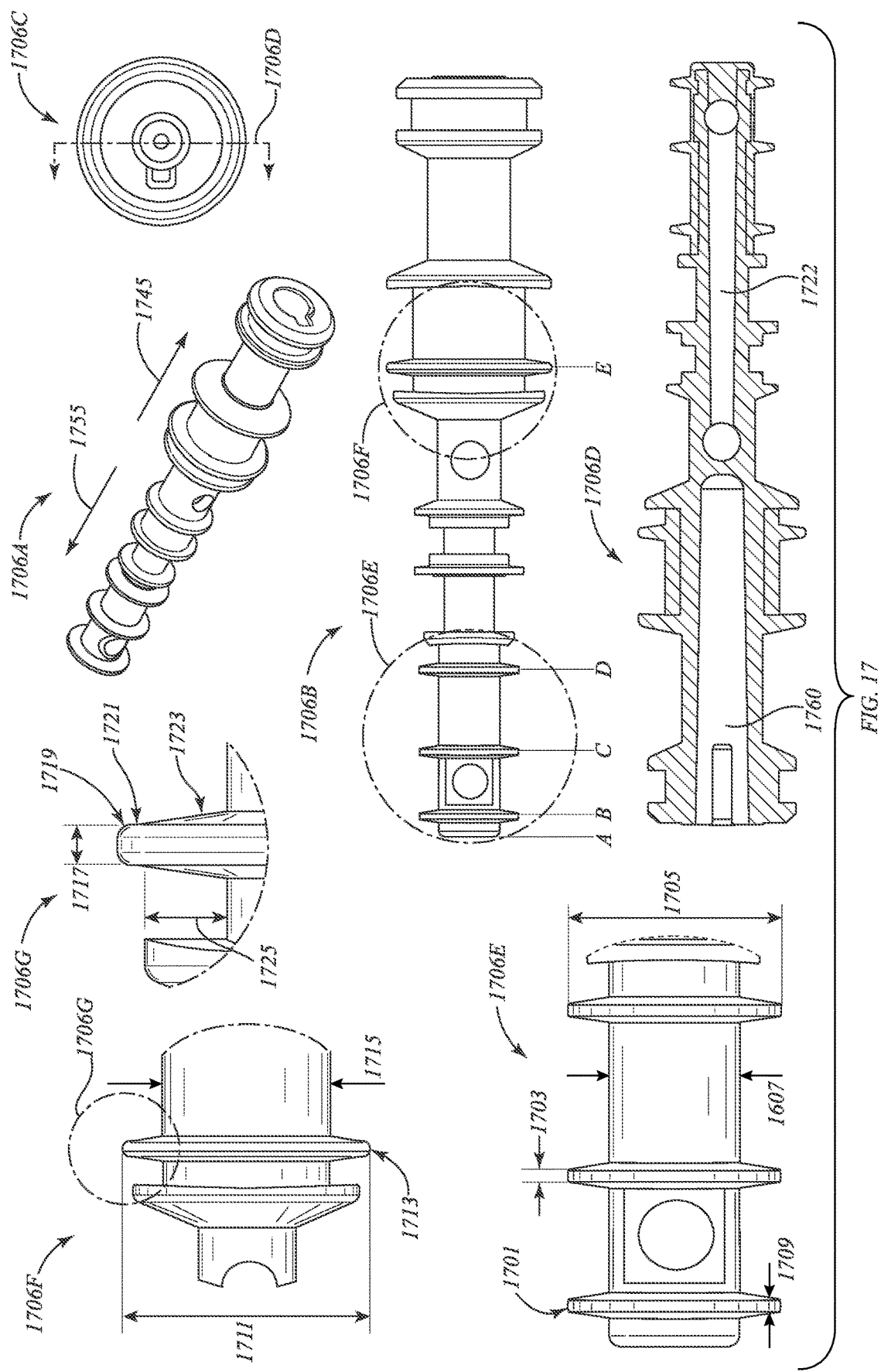
FIG. 17 illustrates various aspects of an exemplary valve stem according to the present disclosure described herein.
Figure 18:
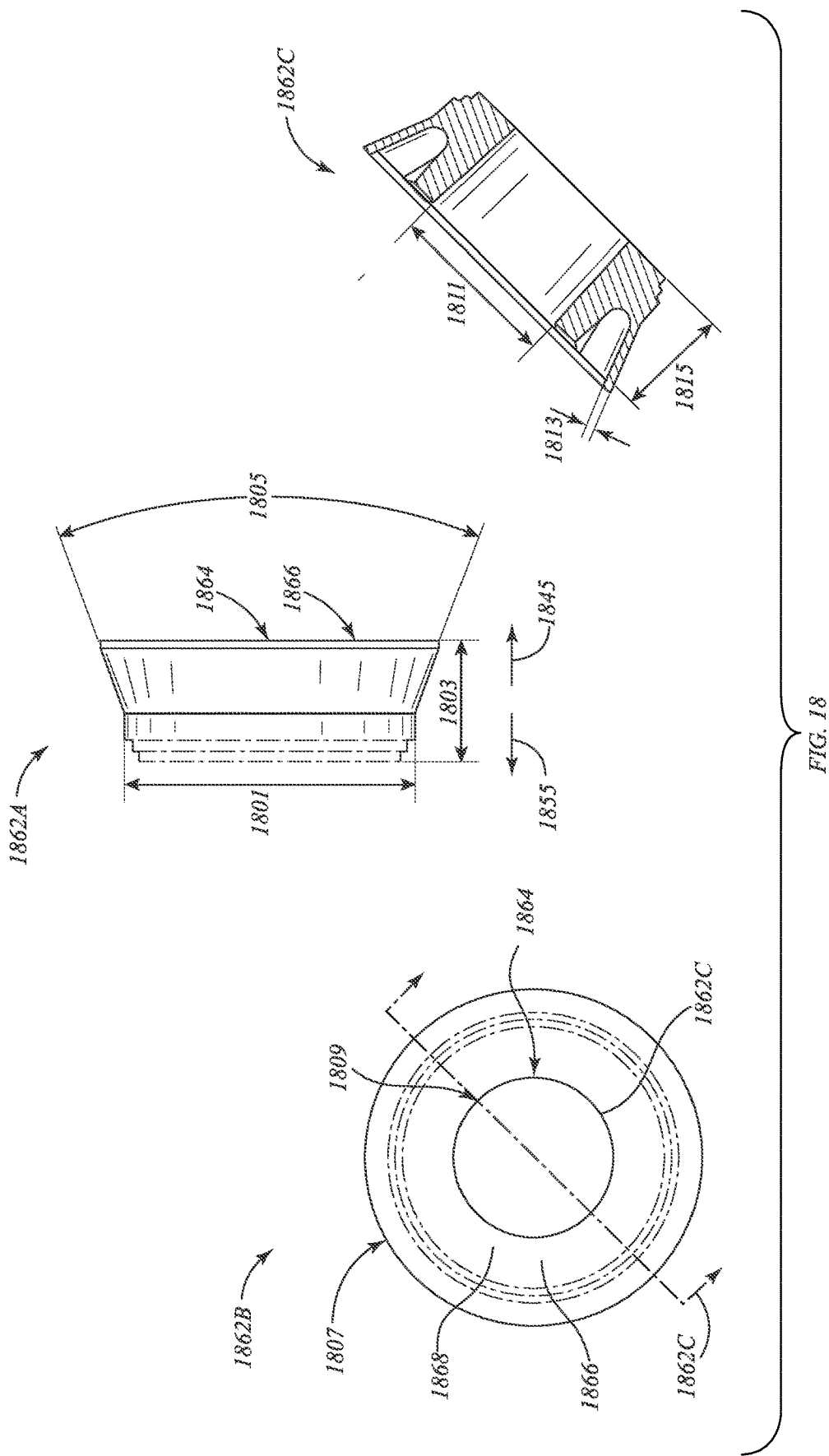
FIG. 18 illustrates various aspects of an exemplary one-way seal according to the present disclosure described herein.

FIGS. 15-18 illustrate various aspects of an exemplary valve assembly 1502 (or cleaning valve 1502) according to the present disclosure described herein. In some embodiments, the valve assembly 1502 and/or components thereof may be the same or similar in form and/or function to one or more other components described herein, such as with respect to FIGS. 8-12. FIG. 15 shows various views of the valve assembly 1502. In many embodiments, the valve assembly 1502 may include, or be referred to, as a cleaning valve assembly, a cleaning valve, a valve, a valve assembly, or similar. FIG. 16 shows various views of an interface member 1604 for the valve assembly 1502. FIG. 17 shows various views of a valve stem 1706 for the valve assembly 1502. FIG. 18 shows various views of a one-way seal 1862 for the valve assembly 1502. Embodiments are not limited in this context.

FIG. 15 may include a perspective view 1502A, a front view 1502B, and a cross-sectional view 1502C of cleaning valve assembly 1502. As shown in the perspective view 1502A, valve assembly 1502 may include a proximal end 1545 and a distal end 1555. As shown in the front view 1502B, the cleaning valve assembly 1502 may include an interface member 1504, a valve stem 1506, and a one-way seal. Additionally, as shown in cross-section 1502C, the cleaning valve assembly 1502 may include seals 1524-1, 1524-2, 1524-3, 1524-4 (or seals 1524), proximal seal assembly 1544 (includes seal 1524-1), distal seal assembly 1542 (includes seals 1524-2, 1524-3, 1524-4), one or more annular indentations or channels 1586 of valve stem 1506, one-way seal 1562, orifices 1520-1, 1520-2 (or orifices 1520), and lumen 1522 that places orifices 1520 in fluid communication. In some embodiments, orifice 1520-1 may be the same or similar to proximal aperture 24 and/or orifice 1520-2 may be the same or similar to distal aperture 26. As will be described in more detail below, in various embodiments, valve stem 1506 may include an additional orifice at the distal end that is plugged by seal assembly 1542.

In various embodiments, the interface member 1504 may include a molded elastomer spring cap. In some embodiments, the valve stem 1506 may include 6-millimeter and/or 10-millimeter overmolded seals. For instance, seal 1524-1 of seal assembly 1544 may be a 10-millimeter overmolded seal and seals 1524-2, 1524-3, 1524-4 may be 6-millimeter overmolded seals. In many embodiments, the one-way seal 1562 may include an air water valve one-way seal. In various embodiments, the one or more annular indentations or channels 1586 of valve stem 1506 may facilitate coupling of the interface member 1504 to the valve stem 1506. In various such embodiments, the one or more annular indentations or channels 1586 may be the same or similar to annular indentations or channels 86. Similarly, the valve stem 1506 may include one or more annular indentations or channels to facilitate coupling of the one-way seal 1562 to the valve stem 1506. It will be appreciated that additional ways may be used for coupling interface member 1504 and/or one-way seal 1562 to the valve stem 1506 without departing from the scope of this disclosure. For instance, valve stem 1506 may include protrusions instead of channels. In several embodiments, valve assembly 1502 may include up to three separate components (e.g., manufactured separately), valve stem 1506, interface member 1504, and one-way seal 1562, thereby reducing manufacturing and assembly time and costs. In several such embodiments, overmolded components (e.g., seal assembly 1542, 1544) are considered to not be manufactured separately. In some embodiments, the one-way seal 1562 and the valve stem 1506 may be integrally formed or the valve stem 1506 may be overmolded onto the valve stem 1506, reducing the cleaning valve 1502 to a two-piece assembly.

In various embodiments, the surface finish of the valve assembly 1502 may be 85 micro inches or smoother, such as 75 micro inches. For example, the surface finish of the valve assembly 1502 may be 85 micro inches or smoother, such as 63 micro inches. In some embodiments, all burrs and sharp edges may be removed. In many embodiments, the internal corner radii may be 0.04 inches or less. For instance, the internal corner radii may be no more than 0.015 inches. In several embodiments, the interface member 1504 may snap fit over the valve stem 1502 (e.g., via channels 1586). In some embodiments, the proximal end of the interface member 1504 may be coupled to the valve stem 1506 by welding, adhesive, glue, or other known attachment mechanisms. In some embodiments, the one-way seal 1562 may interface with the valve stem 1502 with an interference fit between the inner diameter of the one-way seal 1562 and the outside diameter of the valve stem 1502.

In one or more embodiments described herein, various ranges, tolerances, dimensions, and/or ratios thereof may be selected to suit particular applications. For example, tighter tolerances may be required for gas valve applications than liquid valve applications. In some embodiments, these selections may facilitate and/or optimize one or more functionalities described herein. For instance, accurate dimensions may ensure proper fit into a valve well. In another example, tolerances may ensure operational temperature swings can be accommodated. In yet another example, accurate dimensions may ensure proper function of wiper seals. In still another example, accurate ratios may ensure efficient flow through lumens. In still another example, accurate ratios, tolerances, and/or dimensions may ensure proper operation of the spring portion of an interface member (e.g., both valve position and/or tactile feedback). Accordingly, utilizing one or more ranges, dimensions, and tolerances described herein (and/or ratios thereof) may provide components with reliable operation and/or economical manufacture.

FIG. 16 may include a perspective view 1604A, a front view 1604B, and a cross-sectional view 1604C of interface member 1604. In many embodiments, interface member 1604 may be the same or similar to interface member 1504. As shown in the perspective view 1604A, interface member 1604 may include a proximal end 1645 and a distal end 1655. Additionally, as shown in the cross-section 1604C, the interface member 1604 may include a connector portion 1688 (e.g., an annular protrusion) to facilitate coupling with a valve stem and connector portion 1679 to facilitate coupling with a valve well. In some embodiments, connector portion 1688 may be the same or similar to annular protrusion 88 and/or connector portion 1679 may be the same or similar to feature 79.

In various embodiments, feature 1679 may include a lip and/or recess that is configured to connect with a valve well, as shown proximate the distal end in the cross-section view 1604C of interface member 1604. Further, connector portion 1688 may include a lip and/or recess that is configured to connect with the valve stem 1506, as shown proximate the proximal end in the cross-section view 1604C of interface member 1604 (see also cross-section view 1502C of valve assembly 1502 in FIG. 15). In various embodiments, the interface member 1604 may be the same or similar to the outer cylindrical member 18 in FIGS. 8-12.

The dimensions (e.g., distances, widths, radii, diameters, angles, and the like) are described with respect to components herein in the absence of external input (e.g., in the first configuration). Referring back to the front view 1604B of interface member 1604, the outside diameter 1601 of interface member 1604 may be between 0.62 and 0.65 inches, such as 0.634 inches. The outside diameter 1603 of interface member 1604 may be between 0.61 and 0.64 inches, such as 0.625 inches. The outside diameter 1605 of interface member 1604 may be between 0.57 and 0.60 inches, such as 0.584 inches. The outside diameter 1607 at the distal end of interface member 1604 may be between 0.63 and 0.66 inches, such as 0.640 inches.

Additionally, front view 1604B may include reference points A-F. Reference point A may be the distal end 1655 of the interface member 1604. Reference point B may be at the outside diameter 1601 and the distance between reference points A and B may be between 0.14 and 0.18 inches, such as 0.16 inches. Reference point C may be at the outside diameter 1603 and the distance between reference points A and C may be between 0.35 and 0.40 inches, such as 0.371 inches. Reference point D may be at the outside diameter 1605 and the distance between reference points A and D may be between 0.725 and 0.775 inches, such as 0.748 inches. Reference point E may be the proximal surface of interface member 1604 and the distance between reference points A and E may be between 0.775 and 0.825 inches, such as 0.795 inches. Reference point F may be the proximal side of a raised surface comprised in an indicator of interface member 1604 (see e.g., indicator 108 of FIG. 1A) and the distance between reference points A and F may be between 0.6 and 1.0 inches, such as 0.83 inches. Accordingly, in some embodiments, the raised surface comprised in the indicator may extend proximally around 0.035 inches from the proximal surface of interface member 1604.

Referring back to the cross-sectional view 1604C of interface member 1604, the inside diameter 1609 of interface member 1604 immediately proximal and immediately distal of the annular protrusions 1688 may be between 0.34 and 0.36 inches, such as 0.350 inches. The inside diameter 1611 of interface member 1604 at the annular protrusions 1688 may be between 0.26 and 0.28 inches, such as 0.270 inches. The insider diameter 1619 of interface member 1604 may be between 0.54 and 0.57 inches, such as 0.551 inches. The inside diameter 1627 of interface member 1604 may be between 0.45 and 0.47 inches, such as 0.460 inches. The inside diameter 1629 of interface member 1604 may be between 0.49 and 0.52 inches, such as 0.502 inches. The inside diameter 1631 of interface member 1604 may be between 0.55 and 0.58 inches, such as 0.562 inches. The angle 1617 of interface member 1604 may be between 15 and 31 degrees, such as 23 degrees. The angle 1623 of interface member 1604 may be between 5 and 21 degrees, such as 13 degrees. The angle 1633 of interface member 1604 may be between 15 and 55 degrees, such as 35 degrees. The radius 1613 of interface member 1604 may be between 0.04 and 0.06 inches, such as 0.050 inches. The radius 1615 of interface member 1604 may be between 0.04 and 0.06 inches, such as 0.050 inches. The radius 1621 of interface member 1604 may be between 0.04 and 0.06 inches, such as 0.050 inches. The radius 1625 of interface member 1604 may be between 0.04 and 0.06 inches, such as 0.050 inches.

Additionally, the cross-sectional view 1604C may include reference points G-N. Reference point G may be the distal end 1655 of the interface member 1604. Reference point H may be at the inside diameter 1631 and the distance between reference points G and H may be between 0.05 and 0.08 inches, such as 0.063 inches. Reference point I may be at the inside diameter 1627 and the distance between reference points G and I may be between 0.09 and 0.13 inches, such as 0.108 inches. Reference point J may be at the distal end of radius 1625 and the distance between reference points G and J may be between 0.13 and 0.18 inches, such as 0.154 inches. Reference point K may be at the proximal end of radius 1615 and the distance between reference points G and K may be between 0.5 and 0.7 inches, such as 0.614 inches. Reference point L may be the distal side of annular protrusions 1688 and the distance between reference points G and L may be between 0.5 and 0.8 inches, such as 0.635 inches. Reference point M may be the proximal side of annular protrusions 1688 and the distance between reference points G and M may be between 0.6 and 0.9 inches, such as 0.710 inches. Reference point N may be the proximal end of the internal cavity of interface member 1604 and the distance between reference points G and N may be between 0.72 and 0.80 inches, such as 0.760 inches.

FIG. 17 may include a perspective view 1706A, a side view 1706B, a top view 1706C, a cross-sectional view 1706D, and detail views 1706E, 1706F, 1706G of valve stem 1706. In many embodiments, valve stem 1706 may be the same or similar to valve stem 1506. As shown in the perspective view 1604A, interface member 1604 may include a proximal end 1745 and a distal end 1755. Side view 1706B illustrates the location of detail views 1706E, 1706F with respect to the valve stem 1706. As shown in cross-sectional view 1706D, valve stem 1706 may include a cavity 1760 in addition to lumen 1722. In various embodiments, cavity 1760 may result from removing of a core forming pin used for manufacturing of valve stem 1706. Detail view 1706F illustrates the location of detail view 1706G with respect to detail view 1706F. In various embodiments, valve stem 1706 may include a lip and/or recess that is configured to connect with an interface member (see e.g., channels 1586 of FIG. 15).

Front view 1706B may include reference points A-E. Reference point A may be the distal end 1755 of the valve stem 1706. Reference point E may be at a first seal of valve stem 1706 (see e.g., seal 1524-1 of valve stem 1506) and the distance between reference points A and E may be between 1.0 and 1.3 inches, such as 1.144 inches. Reference point D may be at a second seal of valve stem 1706 (see e.g., seal 1524-2 of valve stem 1506) and the distance between reference points A and D may be between 0.35 and 0.46 inches, such as 0.409 inches. Reference point C may be at a third seal of valve stem 1706 (see e.g., seal 1524-3 of valve stem 1506) and the distance between reference points A and C may be between 0.19 and 0.23 inches, such as 0.210 inches. Reference point B may be at a fourth seal of valve stem 1706 (see e.g., seal 1524-4 of valve stem 1506) and the distance between reference points A and B may be between 0.03 and 0.08 inches, such as 0.053 inches.

The detail view 1706E of FIG. 17 may illustrate the portion of valve stem 1706 comprising a distal seal assembly (see e.g., seal assembly 1542 of valve stem 1506). Further, each of the three seals (see e.g., seals 1524-2, 1524-3, 1524-4 of valve stem 1506) may share dimensions 1701, 1703, 1705, 1709. The radius 1701 proximate the radial extent of each of the seals may be between 0.011 and 0.021 inches, such as 0.016 inches. The width 1703 proximate the radial extent of each of the seals may be between 0.011 and 0.021 inches, such as 0.016 inches with a positive tolerance of 0.003 inches and a negative tolerance of 0.001 inches. The outer diameter 1705 of each of the seals may be between 0.24 and 0.27 inches, such as 0.254 inches. The angle 1709 between proximal and distal sides of each of the seals may be between 10 and 26 degrees, such as 18 degrees. Additionally, the outside diameter 1707 of the distal seal assembly valve stem (see e.g., seal assembly 1542 of valve stem 1506) between each of the seals may be between 0.15 and 0.17 inches, such as 0.16 inches.

The detail view 1706F of FIG. 17 may illustrate the portion of valve stem 1706 comprising a proximal seal assembly (see e.g., seal assembly 1544 including seal 1524-1 of valve stem 1506). The radius 1713 on the proximal and distal sides of the outer extent of the seal may be between 0.007 and 0.009 inches, such as 0.008 inches. The outside diameter 1711 of the seal may be between 0.39 and 0.42 inches, such as 0.404 inches. The outside diameter 1715 of the seal assembly on either side of the seal may be between 0.26 and 0.29 inches, such as 0.272 inches. Referring to the detail view 1706G, the radius 1719 on the proximal and distal sides of the outer extent of the seal may be between 0.007 and 0.009 inches, such as 0.008 inches. The width 1717 proximate the radial extent of the seal may be between 0.014 and 0.034 inches, such as 0.024 inches with a positive tolerance of 0.003 inches and a negative tolerance of 0.001 inches. The angle 1723 between proximal and distal sides of an inner portion of the seal may be between 8 and 24 degrees, such as 16 degrees. The height 1725 of the inner portion of the seal may be between 0.04 and 0.06 inches, such as 0.050 inches. The angle 1723 between proximal and distal sides of an outer portion of the seal may be between 3 and 9 degrees, such as 6 degrees. 8 and 24 degrees, such as 16 degrees. Accordingly, the height of the outer portion of the seal may be between 0.01 and 0.02 inches, such as 0.016 inches.

FIG. 18 may include a side view 1862A, a bottom view 1862B, and a cross-sectional view 1862C of one-way seal 1862. In many embodiments, one-way seal 1862 may be the same or similar to one-way seal 62 of FIG. 8. As shown in the side view 1862A, one-way seal 1862 may include a proximal end 1845 and a distal end 1855. In various embodiments, the one-way seal 1862 may be constructed from a TPE, such as Versaflex CL2250®. In some embodiments, the one-way seal 1862 may be clear/translucent. The dimensions of the illustrated embodiment of FIG. 18 may be in millimeters (mm). In embodiments in which the one-way seal 1862 is molded, element 1866 may indicate the parting line location (i.e., dividing line that splits the core and cavity halves). In various embodiments, element 1864 in views 1862A, 1862B may indicate the flash/parting line mismatch may not exceed 0.1 mm on the surfaces. Further, the flash (i.e., a thin layer of excess material that flows outside the mold's cavity and into the parting line) may not exceed 0.2 mm on other parting lines. In one or more embodiments, element 1866 may indicate the gate location for introducing material, such as during an injection molding process to form the one-way valve 1862.

Further, the maximum gate vestige height as a result of introducing the material into a mold may be 0.5 mm. Element 1868 may indicate the cavity identification location is a maximum of 0.15 mm above the surface. For example, the cavity identification location may be a maximum of 0.13 mm above the surface. The cavity identification may be a letter (e.g., A, B, C, etc.) In many embodiments, one or more corners may be sharp rounded, such as with a max of approximately 0.15 mm. For example, all corners may be sharp rounded with 0.13 mm max. In many embodiments, manufacturing techniques to prevent sink marks must be used to create one-way seal 1862. For instance, sufficient compensation must be provided for when the part is cooling to limit or prevent localized shrinkage at thicker sections. In some embodiments, the one-way seal 1862 may be formed separately from the valve stem and then assembled onto the valve stem. In other embodiments, the one-way seal 1862 may be overmolded or integrally formed with the valve stem.

Referring back to the side view 1862A, the width 1801 of the one-way seal 1862 may be between 8.2 and 8.5 mm, such as 8.33 mm with a tolerance of +/−0.15 mm. The height 1803 of the one-way seal 1862 may be between 3.1 and 3.8 mm, such as 3.46 mm with a tolerance of +/−0.2 mm. The angle 1805 between opposite sides of an upper portion of the one-way seal 1862 may be between 30 and 50 degrees, such as 40.6 degrees. Referring to the bottom view 1862B, the inside diameter 1809 at the distal end of the one-way seal 1862 may be between 4.3 and 5.1 mm, such as 4.7 mm with a tolerance of +/−0.15 mm. The outside diameter 1807 of the one-way seal 1862 may be between 9 and 11 mm, such as 9.7 mm with a tolerance of +/−0.2 mm. Referring to the cross-sectional view 1862C, the width 1813 of the flap (see e.g., flap 63 of FIG. 9) may be between 0.18 and 0.26 mm, such as 0.22 mm with a tolerance of +/−0.05 mm. The height 1815 may be between 3.0 and 3.4 mm, such as 3.20 mm with a tolerance of +/−0.15 mm. The angle 1811 between opposite inside walls of the one-way seal 1862 moving towards the proximal end of the one-way seal 1862 may be between 0 and 6 degrees, such as 2 degrees.

In various embodiments, the flap with width 1813 (see e.g., cross-sectional view 1862C) of the one-way seal 1862 may be referred to as an outer rim and the inner wall of the one-way seal 1862 may be referred to as an inner core.

In various embodiments, one-way seal 1862 may include one or more features to prevent the outer rim from inverting during use. For example, one-way seal 1862 may include one or more bridges connecting the outer rim to the inner core. In another example, one or more ribs may be attached to the outer rim. In some examples, the one or more ribs and/or bridges may be attached to an outer rim with a uniform thickness. In yet another example, the thickness of the outer rim may be varied. In various embodiments, the height of the one or more bridges and/or ribs may be a portion of the height of the inner core and/or outer rim. For instance, the one or more bridges and/or ribs may be the same height or half the height of the inner core and/or outer rim. In many embodiments, the ribs and/or bridges may be aligned with the longitudinal (and/or a radial) axis of a valve stem when installed thereon. In one or more embodiments, the ribs and/or bridges may be angled with respect to the longitudinal (and/or a radial) axis of the valve stem when installed thereon. In various embodiments, the one or more ribs and/or bridges may be disposed about the circumference of the inner core. For instance, the one or more ribs and/or bridges may be equally-spaced (or unequally-spaced) about the circumference of the inner core.

Figure 19:
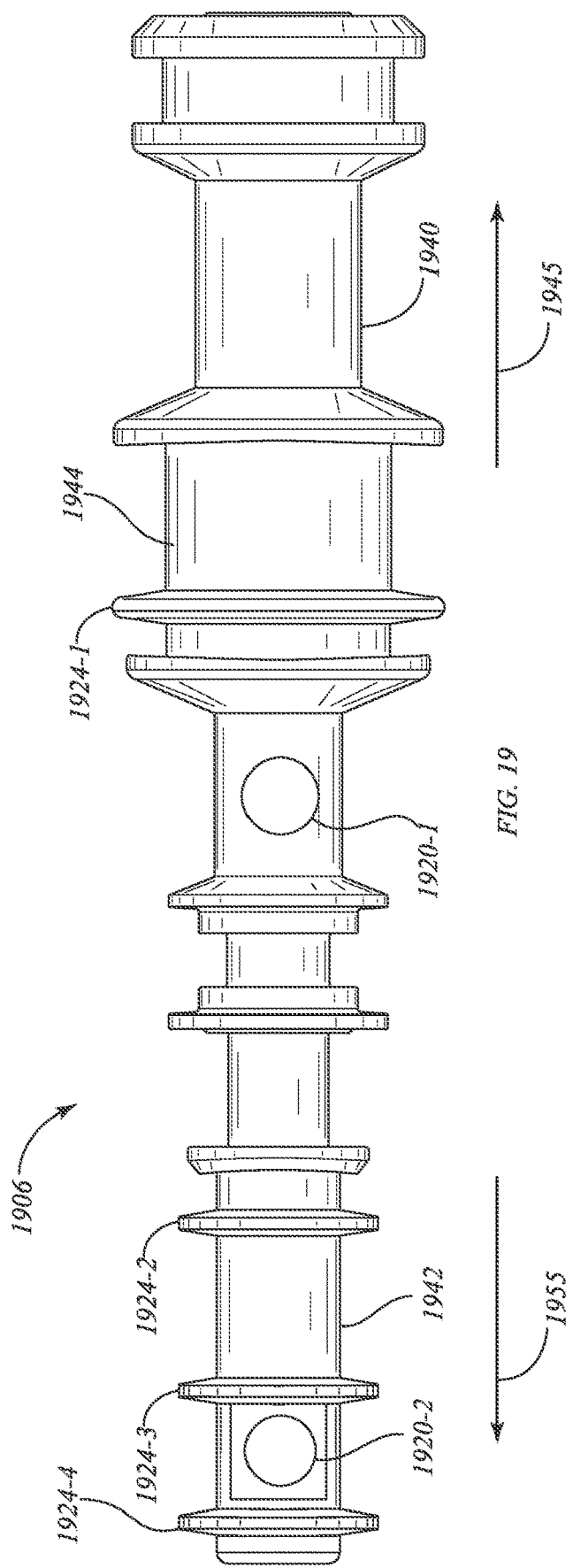
FIG. 19 illustrates various aspects of an exemplary valve stem assembly according to the present disclosure described herein.

FIGS. 19-22B illustrate various aspects of an exemplary valve stem assembly 1906 according to the present disclosure described herein. In some embodiments, the valve stem assembly 1906 and/or components thereof may be the same or similar in form and/or function to one or more other components described herein, such as with respect to FIGS. 8-14. FIG. 19 shows a side view of the valve stem assembly 1906 (or valve stem 1906) with a proximal end 1945 and a distal end 1955. The valve stem 1906 includes a proximal seal assembly 1944, a distal seal assembly 1942, and a bare stem 1940 (or stem 1940). In various embodiments, a stem or bare stem may refer to a valve stem that is missing one or more components, such as overmolded seals, O-rings, and the like. The proximal seal assembly 1944 may include seal 1924-1, the distal seal assembly 1942 may include seals 1924-2, 1924-3, 1924-4, and stem 1940 may include orifices 1920-1, 1920-2 (connected via lumen). In many embodiments, the seal assemblies 1942, 1944 may be overmolded onto the stem 1940.

Figure 20:
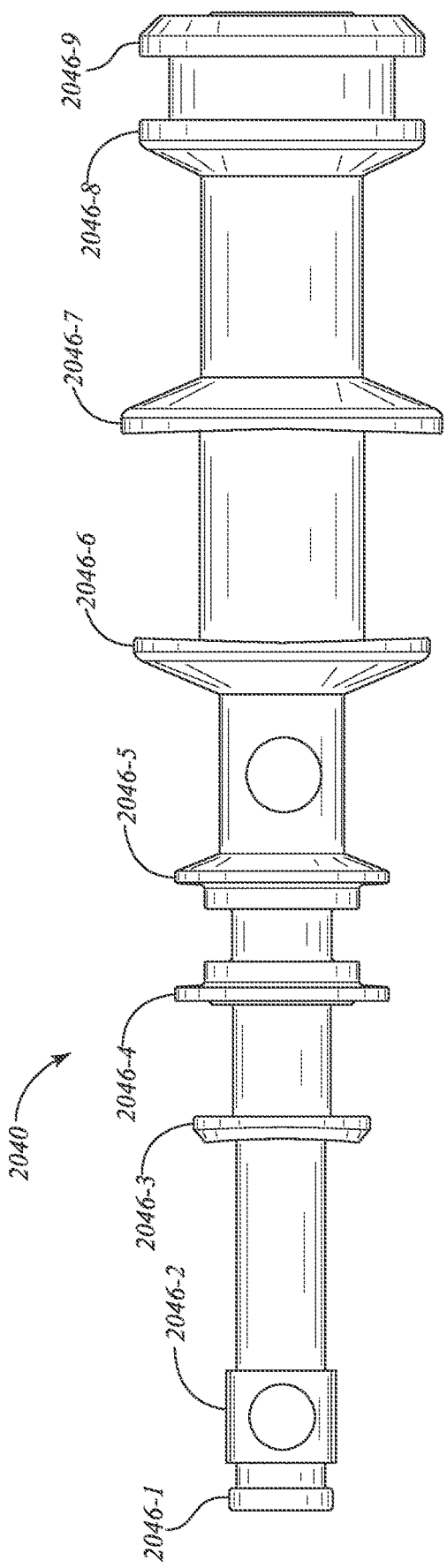
FIG. 20 illustrates various aspects of an exemplary valve stem according to the present disclosure described herein.

FIG. 20 shows a side view of a stem 2040. In various embodiments, stem 2040 may be the same or similar to stem 1940. Stem 2040 may include a plurality of circumferential protrusions 2046-1, 2046-2, 2046-3, 2046-4, 2046-5, 2046-6, 2046-7, 2046-8, 2046-9 (or protrusions 2046). The protrusions 2046 may include one or more features, such as ridges, lips, protrusions, channels, and the like. Additionally, protrusions 2046 may provide one or more functions, such as alignment, coupling, seating, and overmolding support. For example, protrusions 2046-6, 2046-7 may prevent material for forming seal assembly 1944 from flowing proximally or distally during overmolding. Additionally, or alternatively, protrusions 2046-6, 2046-7 may facilitate centering of the stem 2040 within a valve well (e.g., once assembled). In another example, protrusion 2046-3 may prevent material for forming seal assembly 1942 from flowing proximally during overmolding. Further, protrusion 2046-2 may prevent material for forming seal assembly 1942 from flowing into the lumen via the distal orifice during overmolding. In yet another example, the protrusions 2046-8, 2046-9 and the channel defined there between (see e.g., channel 86) may facilitate coupling the stem 2040 to an interface member. In yet another example, the one-way seal may be disposed (or seat) between protrusions 2046-4, 2046-5.

Figure 21A:
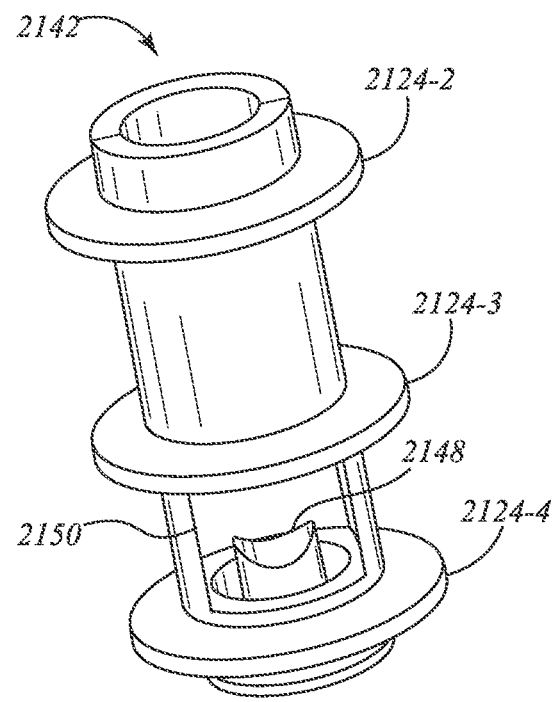
FIGS. 21A and 21B illustrate various aspects of an exemplary seal according to the present disclosure described herein.
Figure 21B:
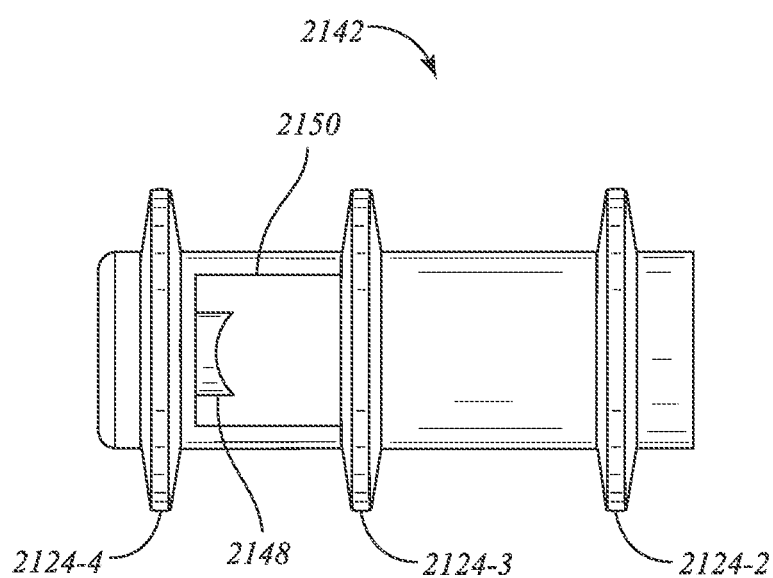

FIG. 21A shows a perspective view of seal assembly 2142. FIG. 21B shows a side view of seal assembly 2142. In various embodiments, the seal assembly 2142 may be the same or similar to seal assembly 1542. The seal assembly 2142 includes seals 2124-2, 2124-3, 2124-4, window 2150, and plug 2148. In some embodiments, window 2150 may be formed by a protrusion during the overmolding process (e.g., protrusion 2046-2). In many embodiments, plug 2148 may seal an orifice in the distal end of a valve stem (see e.g., distal end of valve stem assembly 1502 in cross-sectional view 1502C in FIG. 15).

Figure 22A:
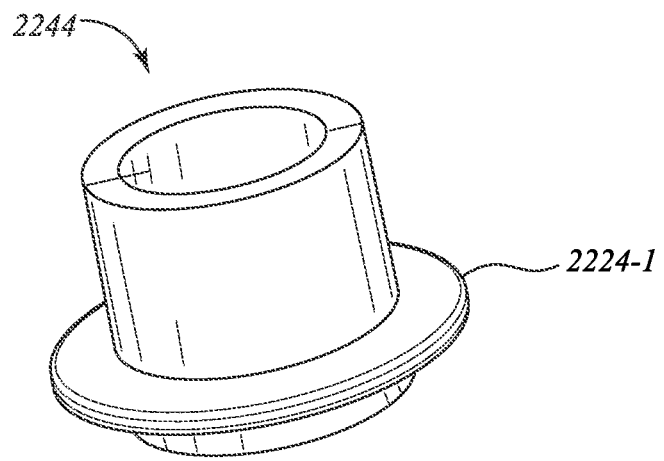
FIGS. 22A and 22B illustrate various aspects of an exemplary seal according to the present disclosure described herein.
Figure 22B:
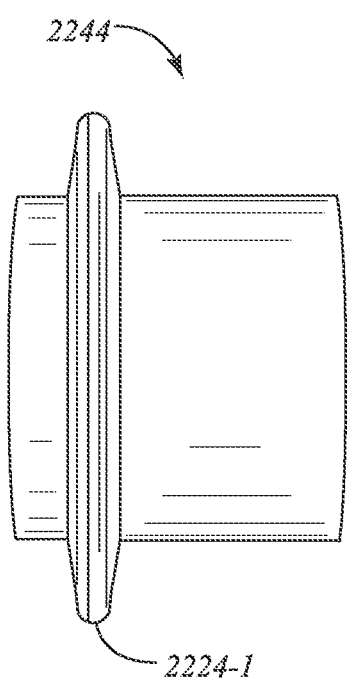

FIG. 22A shows a perspective view of seal assembly 2244. FIG. 22B shows a side view of seal assembly 2244. In various embodiments, the seal assembly 2144 may be the same or similar to seal assembly 1544. In some embodiments, the construction of the seals of seal assemblies being molded plastic, rather than O-rings, may allow them to be molded with a thickness that is less than an O-ring. As such, such molded seals may be designed with a diameter that is greater than an O-ring. Given that the molded seals may thinner and/or of greater diameter than O-ring seals, may provide performance benefits to the valves, compared to valves with O-ring seals. For example, molded seals with greater diameter, but having a flexibility which allows them to slide in a valve well, may provide more surface area contact and sealing against the valve well wall.

In many embodiments, the seal 2242 may fit over (or be formed over) the distal end of the stem 2040. In many such embodiments, the seal assembly 2142 may create a seal with an interior lumen of the valve stem (e.g., via plug 2148. For example, as the valve stem is a single molded component, a lumen is formed during molding that extends through distal tip of the valve stem. The distal end of the lumen may be plugged, e.g., to prevent fluid leakage out of the distal end during use. To plug the lumen, the seal assembly 2142 may include distal tip plug 2148 that extends into the lumen of the valve stem and is integral with at least the overmolded distal disk or "wiper" seal. In one or more embodiments, the seal assembly 2142 may include a plurality of seals. For example, seal assembly 2142 may include or create three seals with a valve well and one seal with a valve stem. In many embodiments, one or more of the seals may include a wiper seal. In the illustrated embodiment, seal assembly 2142 includes a radial opening (e.g., window 2150) that aligns with a radial hole in stem 2040. In some embodiments, the stem 2040 may have one or more features to prevent proximal and/or distal running of material when overmolding one or more of the seal assemblies 2142, 2244.

Figure 23:
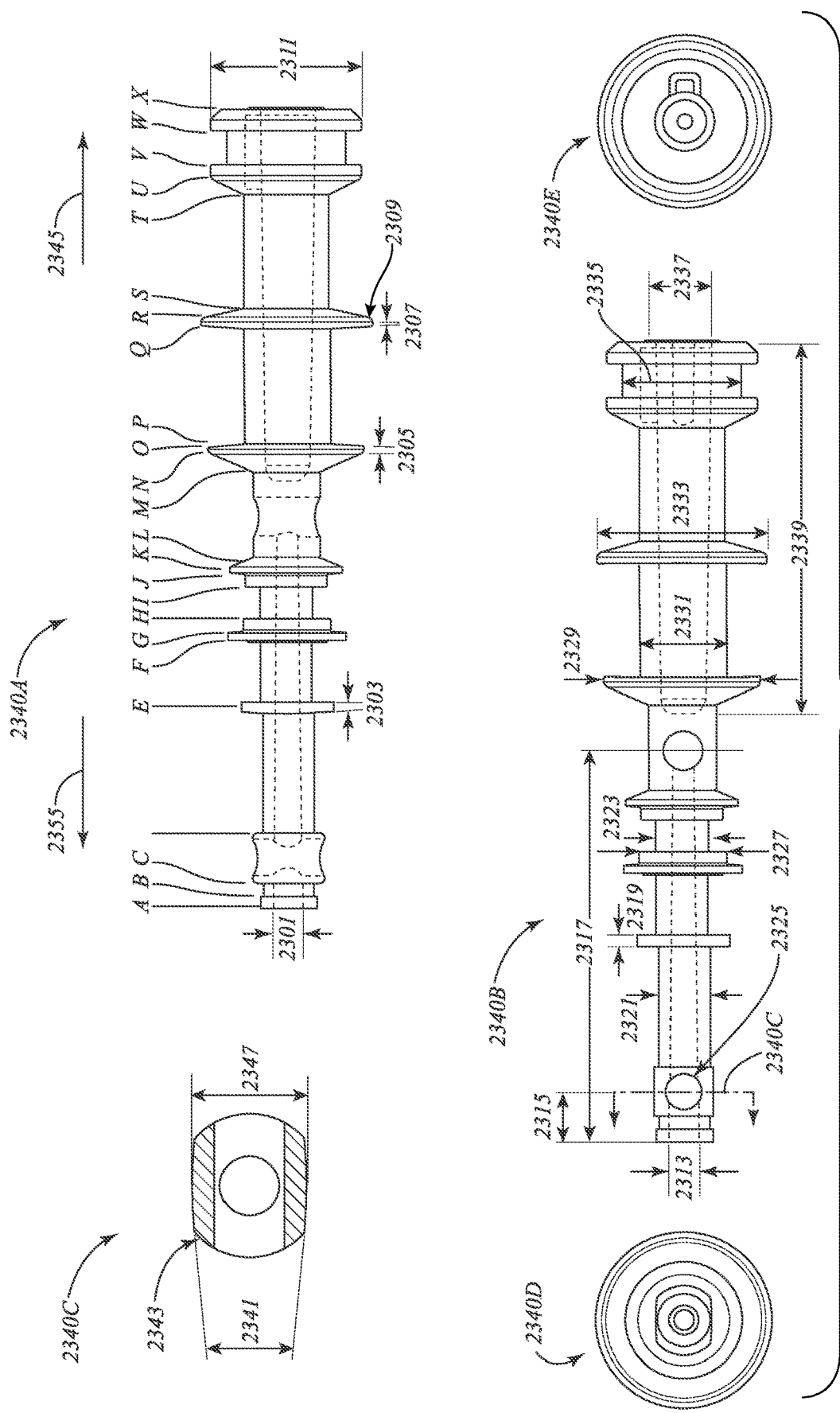
FIG. 23 illustrates various aspects of an exemplary valve stem according to the present disclosure described herein.

FIG. 23 illustrates various aspects of a stem 2340 according to the present disclosure described here. In some embodiments, the stem 2340 and/or components thereof may be the same or similar in form and/or function to one or more other components described herein, such as with respect to FIGS. 8-14. For example, the stem 2340 may be the same or similar to the inner cylindrical member 16 of FIG. 8. The stem 2340 may include a proximal end 2345 and a distal end 2355. In various embodiments, the surface finish of the stem 2340 may be approximately 75 micro inches or smoother. For example, the surface finish of the stem 2340 may be 63 micro inches or smoother. In some embodiments, all burrs and sharp edges may be removed. In many embodiments, the internal corner radii may be approximately 0.02 inches or less. For instance, the internal corner radii may be no more than 0.015 inches. All dimensions are illustrative only, and other dimensions may be more suited to a particular application. Also, dimensions described may be approximations that encompass tolerances, e.g., tolerances allow for plus or minus percentage variations from the described values. Embodiments are not limited in this context.

FIG. 23 may include a first side view 2340A, a second side view 2340B, a cross-sectional view 2340C, a bottom view 2340D, and a top view 2340E of stem 2340. In many embodiments, stem 2340 may be the same or similar to stem 2040. Further, the protrusions 2046 of stem 2040 may be used to describe locations on stem 2340. The first side view 2340A may include reference points A-X. Reference point A may be the distal end 2355 of the stem 2340. Reference point B may be at the proximal side of protrusion 2046-1 and the distance between reference points A and B may be between 0.02 and 0.03 inches, such as 0.026 inches. Reference point C may be at the distal side of protrusion 2046-2 and the distance between reference points A and C may be between 0.05 and 0.07 inches, such as 0.058 inches. Reference point D may be at the proximal side of protrusion 2046-2 and the distance between reference points A and D may be between 0.15 and 0.19 inches, such as 0.171 inches. Reference point E may be at the proximal side of protrusion 2046-3 and the distance between reference points A and E may be between 0.42 and 0.53 inches, such as 0.469 inches. The angle 2303 between a line along the radial direction of the stem 2340 and the distal side of protrusion 2046-3 towards the proximal end 2345 of stem 2340 may be between 0 and 9 degrees, such as 3 degrees.

Reference point F may be at the distal side of protrusion 2046-4 and the distance between reference points A and F may be between 0.58 and 0.65 inches, such as 0.612 inches. Reference point G may be at a step in protrusion 2046-4 and the distance between reference points A and G may be between 0.59 and 0.67 inches, such as 0.630 inches. In many embodiments, the step in protrusion 2046-4 may facilitate positioning and/or coupling the one-way seal. Reference point H may be at the proximal side of protrusion 2046-4 and the distance between reference points A and H may be between 0.63 and 0.69 inches, such as 0.659 inches. Reference point I may be at the distal side of protrusion 2046-5 and the distance between reference points A and I may be between 0.70 and 0.76 inches, such as 0.731 inches. Reference point J may be at a step in protrusion 2046-5 and the distance between reference points A and J may be between 0.735 and 0.795 inches, such as 0.764 inches. In many embodiments, the step in protrusion 2046-4 may facilitate positioning and/or coupling the one-way seal. Reference point K may be at a transition of protrusion 2046-4 and the distance between reference points A and K may be between 0.70 and 0.85 inches, such as 0.775 inches. Reference point L may be at the proximal side of protrusion 2046-5 and the distance between reference points A and L may be between 0.75 and 0.85 inches, such as 0.796 inches.

Reference point M may be at the distal side of protrusion 2046-6 and the distance between points A and M may be between 0.9 and 1.1 inches, such as 0.997 inches. Reference point N may be at a first transition in the protrusion 2046-6 and the distance between points A and N may be between 0.9 and 1.2 inches, such as 1.043 inches. The rounding radius at the first transition may be between 0.009 and 0.015 inches, such as 0.012 inches. Reference point O may be at a second transition in the protrusion 2046-6 and the distance between points A and O may be between 0.9 and 1.2 inches, such as 1.056 inches. Reference point P may be at the proximal side of protrusion 2046-6 and the distance between points A and P may be between 0.92 and 1.22 inches, such as 1.066 inches. The angle 2305 between a line along the radial direction of the valve stem 2340 and the proximal side of protrusion 2046-6 towards the distal end 2355 of stem 2340 may be between 0 and 9 degrees, such as 3 degrees.

Reference point Q may be at the distal side of protrusion 2046-7 and the distance between points A and Q may be between 1.30 and 1.35 inches, such as 1.321 inches. The angle 2307 between a line along the radial direction of the valve stem 2340 and the distal side of protrusion 2046-7 towards the proximal end 2345 of stem 2340 may be between 0 and 9 degrees, such as 3 degrees. Reference point R may be at a transition in the protrusion 2046-7 and the distance between points A and R may be between 1.3 and 1.4 inches, such as 1.349 inches. The rounding radius 2309 at the transition may be between 0.009 and 0.015 inches, such as 0.012 inches. Reference point S may be at the proximal side of protrusion 2046-7 and the distance between points A and S may be between 1.31 and 1.43 inches, such as 1.367 inches.

Reference point T may be at the distal side of protrusion 2046-8 and the distance between points A and T may be between 1.60 and 1.67 inches, such as 1.633 inches. Reference point U may be at a transition in the protrusion 2046-8 and the distal between points A and U may be between 1.61 and 1.72 inches, such as 1.667 inches. The rounding radius at the transition may be between 0.009 and 0.015 inches, such as 0.012 inches. Reference point V may be at the proximal side of protrusion 2046-8 and the distance between points A and V may be between 1.65 and 1.75 inches, such as 1.697 inches. Reference point W may be at the distal side of protrusion 2046-9 and the distance between points A and W may be between 1.73 and 1.85 inches, such as 1.776 inches. Reference point X may be at the distal end of stem 2340 and the distance between points A and X may be between 1.78 and 1.90 inches, such as 1.826 inches. Each of the protrusions 2046-8, 2046-9 may have an outside diameter 2311 of between 0.34 and 0.36 inches, such as 0.348 inches. Additionally, the angle 2301 between opposite walls of the lumen may be between 0 and 5 degrees, such as 1 degree.

Referring to the second side view 2340B, the width 2313 of the lumen at the distal end 2355 of stem 2340 may be between 0.06 and 0.08 inches, such as 0.66 inches. In many embodiments, the plug 2148 may form a slight interference fit with the lumen at the distal end 2355 of stem 2340 to seal the lumen at the distal end 2355 of stem 2340. The distance between the distal end of stem 2340 and the center of the distal orifice may be between 0.10 and 0.13 inches, such as 0.115 inches. The diameter 2328 of the distal orifice may be between 0.07 and 0.09 inches, such as 0.080 inches. The distance between the distal end 2355 of stem 2340 and the center of the proximal orifice may be between 0.8 and 1.0 inches, such as 0.896 inches. The diameter of the proximal orifice may be between 0.07 and 0.09 inches, such as 0.080 inches. The illustrated embodiment includes a distal orifice on both sides of the stem 2340 and a proximal orifice on both sides of the stem 2340.

The outside diameter 2321 of the stem 2340 may be between 0.09 and 0.13 inches, such as 0.110 inches. The width 2319 of protrusion 2046-3 may be between 0.02 and 0.03 inches, such as 0.025 inches. The outside diameter 2327 of the proximal step of protrusion 2046-4 and the outside diameter of the distal step of protrusion 2046-5 of the one-way seal 1862 may be between 0.18 and 0.22 inches, such as 0.200 inches with a tolerance of +/−0.003 inches. The outside diameter 2323 of the stem 2340 between protrusions 2046-4, 2046-5 may be between 0.12 and 0.14 inches, such as 0.13 inches. The length 2339 of the cavity of stem 2340 may be between 0.7 and 1.0 inches, such as 0.849 inches. The width 2337 of the cavity at the proximal end 2345 of stem 2340 may be between 0.12 and 0.14 inches, such as 0.13 inches.

The outside diameter 2329 of protrusion 2046-6 may be between 0.36 and 0.39 inches, such as 0.371 inches with a tolerance of +/−0.003 inches. The outside diameter 2333 of protrusion 2046-7 may be between 0.38 and 0.42 inches, such as 0.400 inches. The outside diameter 2331 of stem 2340 between protrusions 2046-6, 2046-7 may be between 0.18 and 0.22 inches, such as 0.200 inches. The outside diameter 2335 of stem 2340 between protrusions 2046-8, 2046-9 may be between 0.25 and 0.30 inches, such as 0.275 inches.

Referring to the cross-sectional view 2340C, the diameter of protrusion 2046-2 may be between 0.14 and 0.18 inches, such as 0.160 inches. Additionally, the angle 2341 at which protrusion 2046-2 slopes from the center of the lumen at the radial extent of protrusion 2046-2 toward each of the distal orifices may be between 6 and 14 degrees, such as 10 degrees. Other cleaning valve assembly related techniques, features, and/or components that may be used herein are disclosed in U.S. Non-Provisional Patent Application titled "Devices, Systems, and Methods for Medical Cleaning Valves", application Ser. No. 16/868,329, filed on May 6, 2020, now U.S. Pat. No. 11,300,216, the entirety of which is incorporated herein by reference.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit, and scope of the disclosure.

What is claimed is:

1. A cleaning valve, comprising:
   a valve stem;
   an interface member including a proximal end having a proximal surface, a first connector portion, and a second connector portion, the first connector portion coupleable to the valve stem of the cleaning valve; and
   a first indicator comprising one or more raised surfaces on the proximal surface of the interface member and the one or more raised surfaces is a proximal-most surface of the interface member;
   wherein the one or more raised surfaces have a texture that provides tactile differentiation of the cleaning valve from a procedural valve; and
   wherein the one or more raised surfaces comprise an exclamation point surrounded by a geometric shape selected from a triangle, a square, a rhombus or a hexagon.

2. The cleaning valve of claim 1, wherein the one or more raised surfaces comprise the exclamation point surrounded by a triangle.

3. The cleaning valve of claim 1, wherein the interface member comprises a spring portion.

4. The cleaning valve of claim 3, wherein the spring portion of the interface member including an annular wall having a first portion, a second portion distal to the first portion, and a third portion distal to the second portion, and wherein a thickness of the annular wall is smaller at the second portion than at both of the first portion and the third portion.

5. The cleaning valve of claim 4, wherein in response to a force exerted on the proximal surface, the annular wall is expandable radially outward at the second portion.

6. The cleaning valve of claim 1, wherein the second connector portion is disposed at a distal end of the interface member such that the second connector portion is unattached from the valve stem.

7. The cleaning valve of claim 6, wherein the second connector portion is removably attachable to a valve well of an endoscope.

8. The cleaning valve of claim 1, wherein in an attached configuration, the valve stem and the interface member are movable between a first configuration and a second configuration such that the valve stem is movable in a valve well of an endoscope.

9. The cleaning valve of claim 1, wherein the one or more raised surfaces have a pronounced corner that provides tactile differentiation of the cleaning valve from the procedural valve.

10. The cleaning valve of claim 1, wherein the first connector portion of the interface member is configured to couple with the valve stem via an interference fit.

11. The cleaning valve of claim 1, wherein the proximal surface and the one or more raised surfaces comprise different colors, textures, or materials, or combinations thereof.

12. The cleaning valve of claim 1, comprising a second indicator that extends laterally from the interface member.

13. The cleaning valve of claim 12, wherein the second indicator comprises a tag.

14. The cleaning valve of claim 13, wherein the tag is integrally attached to the interface member or wherein the tag is removably attachable to the interface member.

15. A cleaning valve for a medical device, comprising:
   a valve stem including a proximal end, a distal end, one or more orifices, and a lumen in fluid communication with the one or more orifices, where at least one of the one or more orifices is a radial orifice;

a plurality of seals positioned between the proximal end and the distal end of the valve stem, wherein at least one seal of the plurality of seals is overmolded onto the valve stem;

an interface member coupled to the proximal end of the valve stem;

a first indicator to differentiate the cleaning valve from a procedural valve for the medical device, the first indicator including deflectable arms reversibly inserted into the radial orifice in the valve stem, the first indicator preventing insertion of the valve stem into a valve well when the indicator is inserted into the radial orifice in the valve stem; and a second indicator comprising one or more raised surfaces on a proximal surface of the interface member and the one or more raised surfaces is a proximal-most surface of the interface member, wherein the one or more raised surfaces comprise an exclamation point surrounded by a geometric shape selected from a triangle, a square, a rhombus or a hexagon.

16. The cleaning valve of claim 15, wherein the at least one seal surrounds a first orifice of the one or more orifices and the at least one seal plugs a second orifice of the one or more orifices.

17. The cleaning valve of claim 1, wherein the first indicator comprises a retainer clip that is configured to be reversibly inserted into the radial orifice of the valve stem and prevents insertion of the valve stem into the valve well when inserted into the radial orifice of the valve stem.

18. The cleaning valve of claim 15, wherein the radial orifice extends across a diameter of the valve stem.

19. A cleaning valve for an endoscope, comprising:

a valve stem;

an interface member including an elastomer spring cap having an open distal end, a proximal end having a proximal surface, a first connector portion, and a second connector portion, the first connector portion defining a protrusion coupleable to an annular indentation on an outer surface of the valve stem by inserting a proximal end of the valve stem into the open distal end and the second connector portion defining a recess coupleable to a protrusion on an outer surface of a valve cylinder of the endoscope; and a first indicator comprising one or more raised surfaces on the proximal surface of the interface member and the one or more raised surfaces is a proximal-most surface of the interface member;

wherein the one or more raised surfaces provide tactile differentiation of the cleaning valve from a procedural valve and comprise an exclamation point surrounded by a geometric shape selected from a triangle, a square, a rhombus or a hexagon.

20. The cleaning valve of claim 19, wherein the recess defined by the second connector portion is an annular recess, the protrusion on the outer surface the valve cylinder is a radially extending protrusion, and the annular recess is configured to couple to the radially extending protrusion.

* * * * *